US009724322B2

(12) United States Patent
Kuo et al.

(10) Patent No.: US 9,724,322 B2
(45) Date of Patent: *Aug. 8, 2017

(54) 4-(PHENOXYALKYL)THIO)-PHENOXYACETIC ACIDS AND ANALOGS

(71) Applicant: Janssen Pharmaceutica NV, Beerse (BE)

(72) Inventors: Gee-Hong Kuo, Scotch Plains, NJ (US); Rui Zhang, Belle Mead, NJ (US); Aihua Wang, Jamison, PA (US); Alan R. DeAngelis, Pennington, NJ (US)

(73) Assignee: Janssen Pharmaceutica N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,125

(22) Filed: Mar. 18, 2016

(65) Prior Publication Data

US 2016/0199342 A1  Jul. 14, 2016

Related U.S. Application Data

(60) Continuation of application No. 13/966,493, filed on Aug. 14, 2013, now abandoned, which is a continuation of application No. 13/332,453, filed on Dec. 21, 2011, now Pat. No. 8,518,997, which is a division of application No. 12/623,824, filed on Nov. 23, 2009, now Pat. No. 8,106,095, which is a division of application No. 11/872,417, filed on Oct. 15, 2007, now Pat. No. 7,635,718, which is a division of application No. 10/942,478, filed on Sep. 16, 2004, now Pat. No. 7,301,050.

(60) Provisional application No. 60/504,146, filed on Sep. 19, 2003.

(51) Int. Cl.
| | | |
|---|---|---|
| *A61K 31/277* | (2006.01) | |
| *A61K 31/192* | (2006.01) | |
| *C07C 323/20* | (2006.01) | |
| *C07C 59/68* | (2006.01) | |
| *C07C 59/70* | (2006.01) | |
| *C07C 317/22* | (2006.01) | |
| *C07C 323/60* | (2006.01) | |
| *C07C 323/62* | (2006.01) | |
| *C07D 333/16* | (2006.01) | |
| *C07D 333/28* | (2006.01) | |

(52) U.S. Cl.
CPC .......... *A61K 31/277* (2013.01); *A61K 31/192* (2013.01); *C07C 59/68* (2013.01); *C07C 59/70* (2013.01); *C07C 317/22* (2013.01); *C07C 323/20* (2013.01); *C07C 323/60* (2013.01); *C07C 323/62* (2013.01); *C07D 333/16* (2013.01); *C07D 333/28* (2013.01)

(58) Field of Classification Search
None
See application file for complete search history.

(56) References Cited

U.S. PATENT DOCUMENTS

| 4,073,935 A | 2/1978 | Grill et al. |
| 4,125,732 A | 11/1978 | McEnvoy et al. |
| 4,513,006 A | 4/1985 | Maranoff et al. |
| 4,737,495 A | 4/1988 | Bomhard et al. |
| 4,820,867 A | 4/1989 | Belanger et al. |
| 5,360,909 A | 11/1994 | Igarashi et al. |
| 5,487,008 A | 1/1996 | Ribbens et al. |
| 5,726,165 A | 3/1998 | Beeley et al. |
| 7,301,050 B2 | 11/2007 | Kuo et al. |
| 7,425,649 B2 | 9/2008 | Kuo et al. |
| 7,598,292 B2 | 10/2009 | Kuo et al. |
| 7,598,416 B2 | 10/2009 | Kuo et al. |
| 7,635,718 B2 | 12/2009 | Kuo et al. |
| 7,709,682 B2 | 5/2010 | Abdel-Magid et al. |
| 8,106,095 B2 | 1/2012 | Kuo et al. |
| 8,518,997 B2 * | 8/2013 | Kuo .................. C07C 59/68 |
| | | 514/570 |
| 8,669,288 B2 * | 3/2014 | Abdel-Magid ....... C07C 323/20 |
| | | 514/555 |
| 2003/0225158 A1 | 12/2003 | Auerbach et al. |
| 2004/0143006 A1 | 7/2004 | Jeppesen et al. |
| 2005/0107469 A1 | 5/2005 | Kuo et al. |
| 2005/0124698 A1 | 6/2005 | Kuo et al. |
| 2006/0004091 A1 | 1/2006 | Ackermann et al. |
| 2006/0058382 A1 | 3/2006 | Kuo et al. |
| 2006/0058393 A1 | 3/2006 | DeAngelis et al. |
| 2006/0257987 A1 | 11/2006 | Gonzalez Valcarcel |
| 2007/0060649 A1 | 3/2007 | Abdel-Magid et al. |
| 2009/0318332 A1 | 12/2009 | Kuo et al. |

(Continued)

FOREIGN PATENT DOCUMENTS

| DE | 3026924 A1 | 2/1982 |
| DE | 3028776 A1 | 2/1982 |

(Continued)

OTHER PUBLICATIONS

PCT International Search Report relating to International Application No. PCT/US2004/030375 which relates to U.S. Appl. No. 10/942,478. Date of Mailing of International Search Report, Jun. 1, 2005.
Anderson, B.D. and Flora, K. P., "Chapter 34: Preparation of Water-Soluble Organic Compounds Through Salt Formation.", *Latest pharmaceutical chemistry, lower volume.*, Sep. 25, 1999, pp.347-349, Japan, ISBN4-924746-80-0.
Auboeuf et al., "Tissue Distribution and Quantification of the Expression of mRNAs of Peroxisome Proliferator-Activated Receptors and Liver X Receptor-α in Humans.", Diabetes, 1997, vol. 46(8), pp. 1319-1327.
Barak et al., "Effects of peroxisome proliferator-activated receptor ∂ on placentation, adiposity, and colorectal cancer.", PNAS, 2002, vol. 1999(1), pp. 303-308, USA.
Berge et al., "Pharmaceuctical Salts.", Journal of Pharmaceutical Sciences, 1977, vol. 66, pp. 1-64.

(Continued)

*Primary Examiner* — Rosalynd Keys

(57) ABSTRACT

The invention features 4-((phenoxyalkyl)thio)-phenoxyacetic acids and analogs, compositions containing them, and methods of using them as PPAR delta modulators to treat or inhibit the progression of, for example, dyslipidemia.

6 Claims, No Drawings

(56) References Cited

U.S. PATENT DOCUMENTS

| | | |
|---|---|---|
| 2010/0004470 A1 | 1/2010 | Kuo et al. |
| 2010/0069469 A1 | 3/2010 | Young et al. |
| 2010/0069496 A1 | 3/2010 | Kuo et al. |

FOREIGN PATENT DOCUMENTS

| | | |
|---|---|---|
| EP | 0056172 A2 | 7/1982 |
| EP | 0092136 A | 10/1983 |
| EP | 0106565 A | 4/1984 |
| EP | 0204349 A3 | 12/1986 |
| EP | 1424330 A1 | 6/2004 |
| EP | 1445258 A1 | 8/2004 |
| JP | 61-268651 A | 11/1986 |
| JP | 2160758 A | 6/1990 |
| JP | 10195057 A | 7/1998 |
| WO | WO 97/27847 A1 | 8/1997 |
| WO | WO 97/28115 A | 8/1997 |
| WO | WO 99/04815 A1 | 2/1999 |
| WO | WO 00/63153 A1 | 10/2000 |
| WO | WO 01/00603 A1 | 1/2001 |
| WO | WO 02/062774 A | 8/2002 |
| WO | WO 02/100813 A | 12/2002 |
| WO | WO 03/011807 | 2/2003 |
| WO | WO 03/059875 A2 | 7/2003 |
| WO | WO 03/074495 | 9/2003 |
| WO | WO 2004/000315 A1 | 12/2003 |
| WO | WO 2004/037775 A1 | 5/2004 |
| WO | WO 2004/037776 A2 | 5/2004 |
| WO | WO 2004/074439 A | 9/2004 |
| WO | WO 2005/019151 | 3/2005 |
| WO | WO 2005/030694 | 4/2005 |
| WO | WO 2005/041959 A1 | 5/2005 |
| WO | WO 2005/103055 A1 | 11/2005 |
| WO | WO 2006/059234 A2 | 6/2006 |

OTHER PUBLICATIONS

Boden, G., "Free Fatty Acids, Insulin Resistance, and Type 2 Diabetes Mellitus.", Proceedings of the Association of American Physicians, 1991, vol. 111(3), pp. 241-248.

Braissant et al., "Differential Expression of Peroxisome Proliferator-Activated Receptors (PPARs): Tissue Distribution of PPAR-α, β, and -γ in the Adult Rat*.", Endocrinology, 1996, pp. 354-366, vol. 137(1).

Brooks et al., "Design and Synthesis of 2-Methyl-2-{4-[2(5-methyl-2-aryloxazol-4-yl)ethoxy]phenoxy}propionic Acids: A New Class of Dual PPAR α/γ Agonists.", Journal of Medicinal Chemsitry, 2001, pp. 2061-2064, vol. 44(13).

Gould P.L., "Salt Selection for Basic Drugs.", International J. Pharm., 1986, vol. 33, pp. 201-217.

Heald et al., "Dual Action and Pan-PPAr Activators as Potential Anti-diabetic Therapies.", Handbook of Experimental Pharmacology 203, 2011, pp. 35-51.

Kawamatsu et al., "Studies on Antihyperlipidemic Agents. II. Synthesis and biological activities of 2-chloro-3-arylpropionic acids*., " Central Research Division, Takeda Chemical Ltd., Osaka, JP, 1980, pp. 585-589.

Lawn et al., "The Tangier disease gene product ABC1 controls the cellular apolipoprotein-mediated lipid removal pathway.", J. Clin. Investigation, 1999, vol. 104(8), pp. R25-R31.

Leibowitz et al., "Activation of PPARδ alters lipid metabolism in db/db mice.", FEBS Lett., 2000, pp. 333-336, vol. 473(3).

Ohsumi, K. et al. "Pyrazole-O-Glucosides as Novel Na+-Glucose Cotransporter (SGLT) Inhibitors" Bioorganic & Medicinal Chemistry Letters, 2003, vol. 13, pp. 2269-2272.

Oliver et al., "A selective peroxisome proliferator-activated receptor δ agonist promotes reverse cholesterol transport.", PNAS, 2001, vol. 98(9), pp. 5306-5311, USA.

Pomerantz et al., "Formaldehyde Semicarbazone.", J. Org. Chem., 1982, vol. 47 (11), pp. 2217-2218.

Silverman, Richard B., The Organic Chemistry of Drug Design and Drug Action, 1992, pp. 15-20.

Shi et al., "The peroxisome proliferator-activated receptor ,an integrator of transcriptional repression and nuclear receptor signaling.", Proc Natl. Acad. Sci., 2002, vol. 99(5), pp. 2613-2618, USA.

Spinelli et al., "Application of the Hammett relationship to a series of tetrasubstituted thiophens. Kinetics of piperidino-debromination of some 2-bromo-3-nitro-5-X-thiophens and 2-bromo-4-methyl-3-nitro-5-X-thiophens in methanol.", J. Chem. Soc., Perkin Trans. 2, 1972, pp. 1866-1869. DOI: 10.1039/P29720001866.

Still et al., "Rapid Chromatographic Technique for Preparative Separations with Moderate Resolution.", J. Org. Chem., 1978, vol. 43(14), pp. 2923-2925.

Sznaidman et al., "Novel Selective Small Molecule Agonists for Peroxisome Proliferator-Activated Receptor ∂ (PPAR∂)-Synthesis and Biological Activity.", Bioorganic & Medicinal Chemistry Letters, 2003, 13(9), 1517-1521.

Tanaka et al., "Activation of peroxisome proliferator-activated receptor ∂ induces fatty acid B-oxidation in skeletal muscle and attenuates metabolic syndrome.", PNAS, Dec. 23, 2003, vol. 100(26), pp. 15924-15929, U.S.A.

Tanaka, H. et al. "Solid-Phase Synthesis of β-Mono-Substituted Ketones and an Application to the Synthesis of a Library of Phlorizin Derivatives", Letter, 2002, pp. 1427-1430.

Wang et al., "Peroxisome-Proliferator-Cativated Receptor ∂ Activates Fat Metabolism to Prevent Obesity.", Cell, Apr. 18, 2003, vol. 113, pp. 159-170, Cell Press.

* cited by examiner

4-(PHENOXYALKYL)THIO)-PHENOXYACETIC ACIDS AND ANALOGS

CROSS-REFERENCE TO RELATED APPLICATIONS

This Application is a continuation of U.S. patent application Ser. No. 13/966,493, filed Aug. 14, 2013, which is a continuation of U.S. patent application Ser. No. 13/332,453, filed Dec. 21, 2011, now U.S. Pat. No. 8,518,997, which is a divisional of U.S. patent application Ser. No. 12/623,824, filed Nov. 23, 2009, now U.S. Pat. No. 8,106,095, which is a divisional of U.S. patent application Ser. No. 11/872,417, filed Oct. 15, 2007, now U.S. Pat. No. 7,635,718, which is a divisional of U.S. patent application Ser. No. 10/942,478, filed Sep. 16, 2004, now U.S. Pat. No. 7,301,050, which claims priority to U.S. Provisional Patent Application No. 60/504,146, filed Sep. 19, 2003, the disclosures of which are hereby incorporated by reference in their entireties.

STATEMENT REGARDING FEDERALLY SPONSORED RESEARCH OR DEVELOPMENT

The research and development of the invention described below was not federally sponsored.

BACKGROUND OF THE INVENTION

Cardiovascular disease (CVD) is prevalent in the world and is often associated with other disease states such as diabetes and obesity. Many population studies have attempted to identify the risk factors for CVD; of these, high plasma levels of low density lipoprotein cholesterol (LDL-C), high plasma levels of triglycerides (>200 mg/dl), and low levels of high density lipoprotein cholesterol (HDL-C) are considered to be among the most important. Currently, there are few therapies targeting low HDL-C and triglycerides.

The peroxisome proliferator-activated receptors (PPARs) are metabolic sensors regulating the expression of genes involved in glucose and lipid homeostasis. Agonists of the PPARα subtype, such as LOPID® (gemfibrozil) and TRICOR® (fenofibrate), and agonists of the PPARγ subtype, such as AVANDIA® (rosiglitazone maleate), are used for the treatment of dyslipidemia and diabetes, respectively. Another member of this nuclear receptor family, the peroxisome proliferator-activated receptor delta (PPAR delta or PPARδ) is also a necessary transcription factor reported to be involved in regulating genes involved in lipid metabolism and energy expenditure. PPAR delta has been shown to act as a "gateway" receptor modulating the expression of the other PPARs (Shi et al., 2002, Proc Natl. Acad. Sci USA, 99(5): 2613-2618). Each receptor subtype has a distinct tissue distribution: 1) PPARα shows the highest expression in liver, 2) PPARγ appears primarily in adipose tissue, and 3) PPARδ has the widest distribution—ubiquitously in adult rat (Braissant et al., 1996, Endocrinology 137(1): 354-366) and in all the human tissues tested to date, including liver, kidney, abdominal adipose and skeletal muscle (Auboeuf et al., 1997, Diabetes 46(8):1319-1327).

Recently, potent ligands for PPARδ have been published, providing a better understanding of its function in lipid metabolism. The main effect of these compounds in db/db mice (Leibowitz et al., 2000, FEBS Lett. 473(3):333-336) and obese rhesus monkeys (Oliver et al., 2001, Proc. Natl. Acad. Sci. USA 98(9):5306-5311) was an increase in high density lipoprotein cholesterol (HDL-C) and a decrease in triglycerides, with little effect on glucose (although insulin levels were decreased in monkeys). HDL-C removes cholesterol from peripheral cells through a process called reverse cholesterol transport. The first and rate-limiting step, a transfer of cellular cholesterol and phospholipids to the apolipoprotein A-I component of HDL, is mediated by the ATP binding cassette transporter A1 (ABCA1) (Lawn et al., 1999, J. Clin. Investigation 104(8): R25-R31). PPARδ activation has been shown to increase HDL-C level through transcriptional regulation of ABCA1 (Oliver et al., 2001, Proc. Natl. Acad. Sci. USA 98(9): 5306-5311). Through induction of ABCA1 mRNA expression in macrophages, PPARδ agonists may increase HDL-C levels in patients and remove excess cholesterol from lipid-laden macrophages, thereby inhibiting the development of atherosclerotic lesions. Existing therapy for hypercholesterolemia includes the statin drugs, which decrease LDL-C but show little effect on HDL-C, and the fibrates, the PPARα agonists that have low potency and induce only modest HDL-C elevation. In addition, like the fibrates, PPARδ agonists may also reduce triglycerides, an additional risk factor for cardiovascular disease and diabetes. Elevated free fatty acid level has been shown to contribute to insulin resistance and progression of diabetes (Boden, G. PROCEEDINGS OF THE ASSOCIATION OF AMERICAN PHYSICIANS (1999 May-June), 111(3), 241-8).

Examples of known PPAR delta agonists variously useful for hyperlipidemia, diabetes, or atherosclerosis include L-165041 (Leibowitz et al., 2000) and GW501516 (Oliver et al., Proceedings of the National Academy of Sciences of the United States of America (2001), 98(9), 5306-5311). Treatment of differentiated THP-1 monocytes with GW501516 induced ABCA1 mRNA expression and enhanced cholesterol efflux from these cells.

SUMMARY OF THE INVENTION

The invention features compounds of Formula (I) below:

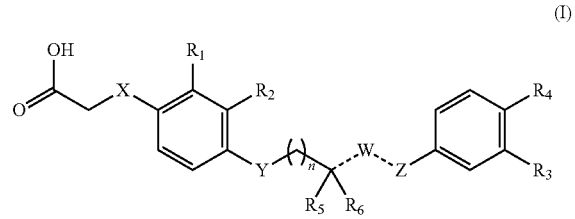

wherein
X is selected from a covalent bond, S, or O;
Y is S or O;
- - - - - W - - - - - represents a group selected from =CH—, —CH=, —CH$_2$—, —CH$_2$—CH$_2$—, =CH—CH$_2$—, —CH$_2$—CH=, =CH—CH=, and —CH=CH—;
Z is selected from O, CH, and CH$_2$, provided when Y is O, Z is O;
R$_1$ and R$_2$ are independently selected from H, C$_{1-3}$ alkyl, C$_{1-3}$ alkoxy, halo, and NR$_a$R$_b$ wherein R$_a$ and R$_b$ are independently H or C$_{1-3}$ alkyl;
R$_3$ and R$_4$ are independently selected from H, halo, cyano, hydroxy, acetyl, C$_{1-5}$ alkyl, C$_{1-4}$ alkoxy, and NR$_c$R$_d$ wherein R$_c$ and R$_d$ are independently H or C$_{1-3}$ alkyl, provided that R$_3$ and R$_4$ are not both H;

$R_5$ is selected from halo, phenyl, phenoxy, (phenyl)$C_{1-5}$alkoxy, (phenyl)$C_{1-5}$alkyl, $C_{2-5}$heteroaryloxy, $C_{2-5}$heteroaryl$C_{1-5}$alkoxy, $C_{2-5}$heterocycyloxy, $C_{1-9}$ alkyl, $C_{1-8}$ alkoxy, $C_{2-9}$ alkenyl, $C_{2-9}$ alkenyloxy, $C_{2-9}$ alkynyl, $C_{2-9}$ alkynyloxy, $C_{3-7}$ cycloalkyl, $C_{3-7}$ cycloalkoxy, $C_{3-7}$cycloalkyl-$C_{1-7}$alkyl, $C_{3-7}$cycloalkyl-$C_{1-7}$alkoxy, $C_{3-7}$cycloalkyloxy-$C_{1-6}$alkyl, $C_{1-6}$alkoxy-$C_{1-7}$alkyl, $C_{1-5}$alkoxy-$C_{1-5}$alkoxy, or $C_{3-7}$cycloalkyloxy-$C_{1-7}$alkoxy;

$R_6$ is H when - - - - - W - - - - - represents a group selected from —CH=, —CH$_2$—, —CH$_2$—CH$_2$—, —CH$_2$—CH=, and —CH=CH—, or $R_6$ is absent when - - - - - W - - - - - represents a group selected from =CH—, =CH—CH$_2$—, and =CH—CH=; and n is 1 or 2;

or a pharmaceutically acceptable salt thereof.

The invention also features compositions that include one or more compounds of Formula (I) and a pharmaceutical carrier or excipient.

These compositions and the methods below may further include additional pharmaceutically active agents, such as lipid-lowering agents or blood-pressure lowering agents, or both.

Another aspect of the invention includes methods of using the disclosed compounds or compositions in various methods for treating, preventing, or inhibiting the progression of, a condition directly or indirectly mediated by PPAR delta. Said condition includes, but is not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

One embodiment of the present invention is a method for treating a PPAR-delta mediated condition, said method comprising administering to a patient in need of treatment a pharmaceutically effective amount of a compound or composition described herein.

Another embodiment of the present invention is a method for inhibiting the onset and/or inhibiting the progression of a PPAR-delta mediated condition, said method comprising administering to a patient in need of treatment a pharmaceutically effective amount of a compound or composition described herein.

Examples of conditions that can be treated with a PPAR delta-agonist include, without limitation, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity. Dyslipidemia includes hypertriglyceridemia, and mixed hyperlipidemia. For example, dyslipidemia (including hyperlipidemia) may be one or more of the following conditions: low HDL (<35 or 40 mg/dl), high triglycerides (>200 mg/dl), and high LDL (>150 mg/dl).

Additional features and advantages of the invention will become apparent from the detailed discussion, examples, and claims below.

DETAILED DESCRIPTION

The invention features compositions containing compounds of Formula (I) in the above Summary section, and methods of using them.

Preferred compounds of the invention are potent PPAR delta agonists that have at least one and preferably two or three of the following characteristics when administered to patients with hypercholesterolemia, hypertriglyceridemia, low-HDL-C, obesity, diabetes and/or Metabolic X Syndrome: 1) increasing HDL-C level, 2) lowering triglycerides, 3) lowering free fatty acids, and 4) decreasing insulin levels. Improvement in HDL-C and triglyceride levels is beneficial for cardiovascular health. In addition, decreased level of triglycerides and free fatty acids contributes to reduce obesity and ameliorate or prevent diabetes.

PPAR delta, being ubiquitously expressed, can act as a gateway receptor that regulates the expression/activity of other nuclear receptors such as other PPARs. For instance, PPAR delta has been shown to block PPARγ-mediated adipogenesis and acyl-CoA oxidase expression; it has also been shown to be associated with the nuclear receptor corepressors SMRT (silencing mediator for retinoid and thyroid hormone receptors), SHARP (SMART and histone deacetylase-associated repressor protein), and HDACs (histone deacetylase). Thus, conditions directly mediated by these nuclear receptors, such as obesity and type II diabetes, can be indirectly mediated by PPAR delta (See, for example, Shi et al., 2002, Proc Natl. Acad. Sci USA, 99(5): 2613-2618).

Some aspects of the invention relate to treating hypertriglyceridemia, raising levels of HDL, lowering levels of LDL, and/or lowering total cholesterol. Preferably, the methods of treatment are associated with improvements in the extent, duration, or degree of side effects, such as edema, normally associated with other existing therapies.

The invention is further described below. The specification is arranged as follows: A) Terms; B) Compounds; C) Synthesis; D) Formulation and Administration; E) Use; F) Biological Examples; G) Other Embodiments; and claims.

A. TERMS

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

Conditions directly or indirectly mediated by PPAR delta include, but are not limited to, diabetes, cardiovascular diseases, Metabolic X Syndrome, hypercholesterolemia, hypo-HDL-cholesterolemia, hyper-LDL-cholesterolemia, dyslipidemia, atherosclerosis, and obesity.

For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term ""jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Unless otherwise noted, as used herein and whether used alone or as part of a substituent group, "alkyl" and "alkoxy" include straight and branched chains having 1 to 8 carbon atoms, such as $C_{1-6}$, $C_{1-4}$, $C_{3-8}$, $C_{2-5}$, or any other range, and unless otherwise noted, include both substituted and unsubstituted moieties. For example, $C_{1-6}$alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are formed from the previously described straight or branched chain alkyl groups. "Alkyl" and "alkoxy" include unsubstituted or substituted moieties with one or more substitutions, such as between 1 and 5, 1 and 3, or 2 and 4 substituents. The substituents may be the same (dihydroxy, dimethyl), similar (chloro, fluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl), aminoalkyl (such as aminomethyl, 2-aminoethyl, 3-aminopropyl, and 2-aminopropyl), alkoxyalkyl, nitroalkyl, alkylalkyl, cyanoalkyl, phenylalkyl, heteroarylalkyl, heterocyclylalkyl, phenoxyalkyl, heteroaryloxyalkyl (such as 2-pyridyloxyalkyl), heterocyclyloxy-alkyl (such as 2-tetrahydropyranoxy-alkyl), thioalkylalkyl (such as MeS-alkyl), thiophenylalkyl (such as phS-alkyl), carboxylalkyl, and so on. A di($C_{1-3}$ alkyl)amino group includes independently selected alkyl groups, to form, for example, methylpropylamino and isopropylmethylamino, in addition dialkylamino groups having two of the same alkyl group such as dimethyl amino or diethylamino.

The term "alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention. "Alkenyl" may be substituted with one or more substitutions including, but not limited to, cyanoalkenyl, and thioalkenyl.

The term "alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

The term "Ac" as used herein, whether used alone or as part of a substituent group, means acetyl ($CH_3CO-$).

The term "halogen" or "halo" shall include iodo, bromo, chloro and fluoro.

The terms "aryl" or "Ar" as used herein refer to an unsubstituted or substituted aromatic hydrocarbon ring system such as phenyl and naphthyl. When the Ar or aryl group is substituted, it may have one to three substituents which are independently selected from $C_1$-$C_8$ alkyl, $C_1$-$C_8$ alkoxy, fluorinated $C_1$-$C_8$ alkyl (e.g., trifluoromethyl), fluorinated $C_1$-$C_8$ alkoxy (e.g., trifluoromethoxy), halogen, cyano, $C_1$-$C_8$ alkylcarbonyl such as acetyl, carboxyl, hydroxy, amino, nitro, $C_1$-$C_4$ alkylamino (i.e., —NH—$C_1$-$C_4$ alkyl), $C_1$-$C_4$ dialkylamino (i.e., —N—[$C_1$-$C_4$ alkyl]$_2$ wherein the alkyl groups can be the same or different), or unsubstituted, mono-, di- or tri-substituted phenyl wherein the substituents on the phenyl are independently selected from $C_1$-$C_8$ alkyl, $C_1$-$C_8$ alkoxy, fluorinated $C_1$-$C_8$ alkyl, fluorinated $C_1$-$C_8$ alkoxy, halogen, cyano, acetyl, carboxyl, hydroxy, amino, nitro, alkylamino, dialkylamino or five or six membered heteroaryl having 1-3 heteroatoms selected from N, O and S.

The term "heteroaryl" as used herein represents a stable, unsubstituted or substituted five or six membered monocyclic or bicyclic aromatic ring system which consists of carbon atoms and from one to three heteroatoms selected from N, O and S. The heteroaryl group may be attached at any heteroatom or carbon atom which results in the creation of a stable structure. Examples of heteroaryl groups include, but are not limited to, benzimidazolyl, benzisoxazolyl, benzofuranyl, benzopyrazolyl, benzothiadiazolyl, benzothiazolyl, benzothienyl, benzotriazolyl, benzoxazolyl, furanyl, furazanyl, furyl, imidazolyl, indazolyl, indolizinyl, indolinyl, indolyl, isobenzofuranyl, isoindolyl, isothiazolyl, isoxazolyl, oxazolyl, purinyl, pyrazinyl, pyrazolyl, pyridazinyl, pyridinyl, pyrimidinyl, pyrrolyl, quinolinyl, quinolyl, thiadiazolyl, thiazolyl, thiophenyl, or triazolyl. When the heteroaryl group is substituted, the heteroaryl group may have one to three substituents including, but not limited to, $C_1$-$C_8$ alkyl, halogen, and aryl.

The term "heterocyclyl" includes optionally substituted nonaromatic rings having carbon atoms and at least one heteroatom (O, S, N) or heteroatom moiety ($SO_2$, CO, CONH, COO) in the ring. A heterocyclyl may be saturated, partially saturated, nonaromatic, or fused. Examples of heterocyclyl include cyclohexylimino, imdazolidinyl, imidazolinyl, morpholinyl, piperazinyl, piperidyl, pyridyl, pyranyl, pyrazolidinyl, pyrazolinyl, pyrrolidinyl, pyrrolinyl, and thienyl.

Unless otherwise indicated, heteroaryl and heterocyclyl may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 5 and 7 ring atoms, or between 5 and 6 ring atoms; there may be between 1 and 5 heteroatoms or heteroatom moieties in the ring, and preferably between 1 and 3, or between 1 and 2 heteroatoms or heteroatom moieties.

Heterocyclyl and heteroaryl also include fused, e.g., bicyclic, rings, such as those optionally fused with an optionally substituted carbocyclic or heterocyclic five- or six-membered aromatic ring. For example, "heteroaryl" includes an optionally substituted six-membered heteroaromatic ring containing 1, 2 or 3 nitrogen atoms fused with an optionally substituted five- or six-membered carbocyclic or heterocyclic aromatic ring. Said heterocyclic five- or six-membered aromatic ring fused with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where chemical moieties are combined, such as in ethoxymethyl or phenylethyl, the term is described in the direction from the periphery to the connection point of the rest of the molecule. For example, ethoxymethyl is $CH_3CH_2OCH_2$— and phenylethyl is a phenyl group linked by —$CH_2CH_2$— to the rest of the molecule (and not a phenyl group linked to the molecule with a $CH_3CH_2$ group as a substituent on the phenyl.) Where parentheses are used, they indicate a peripheral substitution.

As used herein, the term "composition" is intended to encompass a product comprising the specified ingredients in the specified amounts, as well as any product which results, directly or indirectly, from combinations of the specified ingredients in the specified amounts.

Compounds of the invention are further described in the next section.

B. COMPOUNDS

The present invention features compositions containing and methods of using compounds of Formula (I) as described above. Unless otherwise noted, in Formula (I), each hydrocarbyl (alkyl, alkenyl, alkynyl, cycloalkyl, cycloalkenyl, etc) or heterocarbyl (heterocyclyl, heteroaryl, heteroatom moiety such as sulfonyl, amino, amido, etc.) may be substituted or unsubstituted, for example, "alkyl" includes substituted and unsubstituted alkyl and "heterocyclyl" and "aryl" and "alkoxy" and so on, may also be substituted or unsubstituted.

Examples of the present invention include those compounds wherein: (a) X is S or O; (b) X is a covalent bond; (c) X is O; (d) Y is O; (e) Y is S; (f) Z is O; (g) Z is CH or $CH_2$; (h) - - - - - W - - - - - represents —$CH_2$— or —$CH_2$—$CH_2$—; (i) - - - - - W - - - - - represents —$CH_2$—; (j) - - - - - W - - - - - represents =CH—, —CH=, =CH—$CH_2$—, —$CH_2$—CH=, =CH—CH=, or —CH=CH—; (k) $R_1$ and $R_2$ are independently selected from H, $C_{1-3}$ alkyl, $C_{1-3}$ alkoxy, F, Cl, and Br; (l) $R_3$ and $R_4$ are independently selected from H, halo, cyano, $C_{1-4}$ alkyl, and $C_{1-3}$ alkoxy; (m) $R_1$ and $R_2$ are independently selected from H, methyl, methoxy, F and Cl; (n) $R_3$ and $R_4$ are independently selected from H, halo, cyano, hydroxy, $C_{2-4}$ acyl, $C_{1-4}$ alkyl, and $C_{1-3}$ alkoxy; (o) $R_3$ is independently selected from H, F, Cl, methyl, and methoxy; (p) $R_4$ is independently selected from F, Cl, methyl, methoxy, trifluoromethyl, fluoromethyl, difluoromethyl, chlorodifluoromethyl, dichlorofluoromethyl, fluoromethoxy, difluoromethoxy, chlorodifluoromethoxy, dichlorofluoromethoxy and trifluoromethoxy; (q) $R_3$ is selected from methyl, methoxy, H, Cl, Br, I, OH, —$CH(CF_3)_2$, $CF_3$, —$OCF_3$, —$N(CH_3)_2$, —O—$CH_2COOH$, and —$COCH_3$, and $R_4$ is selected from H, Cl, and methyl; (r) $R_5$ is selected from $C_{1-7}$ alkyl, $C_{1-6}$ alkoxy, $C_{2-7}$ alkenyl, $C_{2-7}$ alkenyloxy, $C_{2-7}$ alkynyl, $C_{2-7}$ alkynyloxy, $C_{3-7}$ cycloalkyl, $C_{3-7}$ cycloalkoxy, $C_{1-6}$alkoxy-$C_{1-6}$alkyl, $C_{1-5}$alkoxy-$C_{1-5}$alkoxy, and $C_{3-7}$cycloalkyloxy-$C_{1-7}$alkoxy; (s) $R_5$ is selected from and phenoxy, (phenyl)$C_{1-5}$alkoxy, (phenyl)$C_{1-5}$alkyl, $C_{2-5}$heteroaryloxy, $C_{2-5}$heteroaryl$C_{1-5}$alkoxy, $C_{2-5}$heterocyclyloxy, $C_{3-7}$cycloalkyl-$C_{1-7}$alkyl, $C_{3-7}$cycloalkyl-$C_{1-7}$alkoxy, and $C_{3-7}$cycloalkyloxy-$C_{1-6}$alkyl; (t) $R_6$ is H; (u) $R_3$ is selected from H, F, Cl, methyl and methoxy, and $R_4$ is selected from F, Cl, methyl, fluoromethyl, difluoromethyl, fluoromethoxy, difluoromethoxy, trifluoromethyl, trifluoromethoxy, and methoxy; (v) $R_1$ is selected from H, $CF_3$, methyl, Cl, and methoxy, and $R_2$ is selected from H, Cl, and methyl; (w) $R_1$ is selected from H, $CF_3$, methyl, Cl, and methoxy, and $R_2$ is selected from H, Cl, and methyl, and X is a covalent bond; (x) $R_1$ is selected from H, $CF_3$, methyl, Cl, and methoxy, and $R_2$ is selected from H, Cl, and methyl, X is covalent bond, Y is S, and Z is O; (y) X is O and Y is O; (z) X is O and Y is S; (aa) Y is O and Z is O; (bb) Y is S and Z is O; (cc) $R_6$ is H and $R_5$ is selected from $C_{1-7}$ alkyl, $C_{1-6}$ alkoxy, $C_{2-7}$ alkenyl, $C_{2-7}$ alkenyloxy, $C_{1-6}$alkoxy-$C_{1-6}$alkyl, and $C_{1-5}$alkoxy-$C_{1-5}$alkoxy; (dd) $R_6$ is H and $R_5$ is selected from $C_{1-5}$ alkyl, $C_{1-4}$ alkoxy, $C_{2-5}$ alkenyl, $C_{2-5}$ alkenyloxy, and $C_{1-5}$alkoxy-$C_{1-5}$alkoxy; (ee) $R_6$ is H and $R_5$ is selected from $C_{1-3}$ alkyl, $C_{1-3}$ alkoxy, $C_{2-4}$ alkenyl, $C_{2-4}$ alkenyloxy, and $C_{1-3}$alkoxy-$C_{1-3}$alkoxy; (ff) $R_6$ is H and $R_5$ is selected from methoxy, ethoxy, propoxy, isopropoxy, propenyloxy, isopropenyloxy, ethoxy-methoxy, methoxy-methoxy, methoxymethyl, methoxyethyl, ethoxymethyl, and ethoxy-ethyl; (gg) $R_1$ is selected from H, $CF_3$, methyl, Cl, and methoxy, $R_2$ is selected from H, Cl, and methyl, $R_3$ is selected from H, F, Cl, methyl, and methoxy; and $R_4$ is selected from F, Cl, methyl, trifluoromethyl, trifluoromethoxy, fluoromethyl, fluoromethoxy, difluoromethyl, difluoromethoxy, and methoxy; (hh) X is O, Y is O, $R_3$ is selected from H, F, Cl, methyl, and methoxy; and $R_4$ is selected from F, Cl, methyl, $CF_3$, $OCF_3$ and methoxy; (ii) X is O, Y is S, $R_3$ is selected from H, F, Cl, methyl, and methoxy, and $R_4$ is selected from F, Cl, methyl, $CF_3$, $OCF_3$ and methoxy; (jj) X is covalent bond, Y is S, $R_3$ is selected from H, F, Cl, methyl, and methoxy, and $R_4$ is selected from F, Cl, methyl, $CF_3$, $OCF_3$, and methoxy; (kk) Y is O, Z is O, $R_3$ is selected from H, F, Cl, methyl, and methoxy; and $R_4$ is selected from F, Cl, methyl, $CF_3$, $OCF_3$ and methoxy; (ll) Y is S, Z is O, $R_3$ is selected from H, F, Cl, methyl, and methoxy, and $R_4$ is selected from F, Cl, methyl, $CF_3$, $OCF_3$ and methoxy; (mm) $R_3$ is selected from H, F, Cl, methyl, and methoxy, $R_4$ is selected from F, Cl, methyl, $CF_3$, $OCF_3$, and methoxy, $R_5$ is selected from $C_{1-7}$ alkyl, $C_{1-6}$ alkoxy, $C_{2-7}$ alkenyl, $C_{2-7}$ alkenyloxy, $C_{1-6}$alkoxy-$C_{1-6}$alkyl, and $C_{1-5}$alkoxy-$C_{1-5}$alkoxy and $R_6$ is H; (nn) X is O, Y is O, $R_5$ is selected from $C_{1-3}$ alkyl, $C_{1-3}$ alkoxy, $C_{2-4}$ alkenyl, $C_{2-4}$ alkenyloxy, and $C_{1-3}$alkoxy-$C_{1-3}$alkoxy, and $R_6$ is H; (oo) X is O, Y is S, $R_5$ is selected from $C_{1-3}$ alkyl, $C_{1-3}$ alkoxy, $C_{2-4}$ alkenyl, $C_{2-4}$ alkenyloxy, and $C_{1-3}$alkoxy-$C_{1-3}$alkoxy, and $R_6$ is H; (pp) X is O, Y is O, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, $CF_3$, $OCF_3$ and methoxy, and n is 1; (qq) X is O, Y is S, $R_1$ is selected from H, $CF_3$, methyl, Cl, and methoxy, $R_2$ is selected from H, Cl, and methyl, $R_3$ is selected from H, F, Cl, methyl, and methoxy, and $R_4$ is selected from F, Cl, methyl, $CF_3$, $OCF_3$ and methoxy; (rr) X is O, Y is S, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, $CF_3$, $OCF_3$ and methoxy, and n=1; or (ss) X is O, Y is S, $R_1$ is selected from H, $CF_3$, methyl, Cl, and methoxy, $R_2$ is selected from H, Cl, and methyl, $R_3$ is selected from H, F, Cl, methyl, and methoxy, $R_4$ is selected from F, Cl, methyl, $CF_3$, $OCF_3$ and methoxy, $R_5$ is selected from $C_{1-3}$ alkyl, $C_{1-3}$ alkoxy, $C_{2-4}$ alkenyl, $C_{2-4}$ alkenyloxy, and $C_{1-3}$alkoxy-$C_{1-3}$alkoxy, $R_6$ is H, and n=1; or combinations of the above.

According to another aspect of the invention, Formula (I) is modified such that - - - - - W - - - - - can also be a covalent bond, and $R_6$ is H when - - - - - W - - - - - represents a group selected from a covalent bond, —CH=, —$CH_2$—, —$CH_2$—$CH_2$—, —$CH_2$—CH=, and —CH=CH—, or $R_6$ is absent when - - - - - W - - - - - represents a group selected from =CH—, =CH—CH$_2$—, and =CH—CH=.

Particularly, examples of Formula (I) include those compounds wherein: (a) X is O and Y is O; (b) X is a covalent bond and R$_1$ is selected from H, CF$_3$, methyl, Cl, and methoxy, and R$_2$ is selected from H, Cl, and methyl; (c) X is O and Y is S; (d) X is covalent bond, Y is S and Z is O; (e) Y is S and Z is O; (f) Y is O and Z is O; (g) R$_1$ is selected from H, CF$_3$, methyl, Cl, and methoxy, and R$_2$ is selected from H, Cl, and methyl; (h) R$_1$ and R$_2$ are independently selected from H, methyl, methoxy, F and Cl; (i) R$_3$ is independently selected from H, F, Cl, methyl, and methoxy; (j) R$_4$ is independently selected from F, Cl, methyl, methoxy, trifluoromethyl, fluoromethyl, difluoromethyl, chlorodifluoromethyl, dichlorofluoromethyl, fluoromethoxy, difluoromethoxy, chlorodifluoromethoxy, dichlorofluoromethoxy and trifluoromethoxy; (k) R$_3$ is selected from methyl, methoxy, H, Cl, Br, I, OH, —CH(CF$_3$)$_2$, CF$_3$, —OCF$_3$, —N(CH$_3$)$_2$, —O—CH$_2$COOH, and —COCH$_3$, and R$_4$ is selected from H, Cl, and methyl; (l) R$_3$ is selected from H, F, Cl, methyl, and methoxy, and R$_4$ is selected from F, Cl, methyl, fluoromethyl, difluoromethyl, fluoromethoxy, difluoromethoxy, trifluoromethyl, trifluoromethoxy, and methoxy; (m) R$_5$ is selected from C$_{1-7}$ alkyl, C$_{1-6}$ alkoxy, C$_{2-7}$ alkenyl, C$_{2-7}$ alkenyloxy, C$_{2-7}$ alkynyl, C$_{2-7}$ alkynyloxy, C$_{3-7}$ cycloalkyl, C$_{3-7}$ cycloalkoxy, C$_{1-6}$alkoxy-C$_{1-6}$alkyl, C$_{1-5}$alkoxy-C$_{1-5}$alkoxy, and C$_{3-7}$cycloalkyloxy-C$_{1-7}$alkoxy; (n) R$_6$ is H and R$_5$ is selected from C$_{1-7}$ alkyl, C$_{1-6}$ alkoxy, C$_{2-7}$ alkenyl, C$_{2-7}$ alkenyloxy, C$_{1-6}$alkoxy-C$_{1-6}$alkyl, and C$_{1-5}$alkoxy-C$_{1-5}$alkoxy; (o) R$_6$ is H and R$_5$ is selected from C$_{1-5}$ alkyl, C$_{1-4}$ alkoxy, C$_{2-5}$ alkenyl, C$_{2-5}$ alkenyloxy, and C$_{1-5}$alkoxy-C$_{1-5}$alkoxy; (p) R$_6$ is H and R$_5$ is selected from C$_{1-3}$ alkyl, C$_{1-3}$ alkoxy, C$_{2-4}$ alkenyl, C$_{2-4}$ alkenyloxy, and C$_{1-3}$alkoxy-C$_{1-3}$alkoxy; (q) R$_6$ is H and R$_5$ is selected from methoxy, ethoxy, propoxy, isopropoxy, propenyloxy, isopropenyloxy, ethoxy-methoxy, methoxy-methoxy, methoxymethyl, methoxyethyl, ethoxymethyl, and ethoxy-ethyl; or - - - - - W - - - - - represents a covalent bond; or combinations of the above.

In another example, compounds of the present invention can be those of Formula (II):

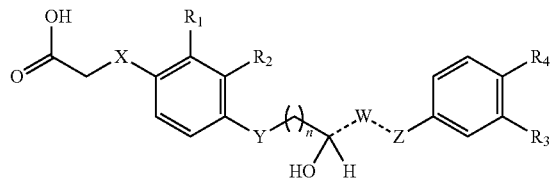

II wherein
X is selected from a covalent bond, S, or O;
Y is S or O;
- - - - - W - - - - - represents a group selected from —CH=, —CH$_2$—, —CH$_2$—CH$_2$—, —CH$_2$—CH=, and —CH=CH—;
Z is selected from O, CH, and CH$_2$, provided when Y is O, Z is O;
R$_1$ and R$_2$ are independently selected from H, C$_{1-3}$ alkyl, C$_{1-3}$ alkoxy, halo, and NR$_a$R$_b$ wherein R$_a$ and R$_b$ are independently H or C$_{1-3}$ alkyl;
R$_3$ and R$_4$ are independently selected from H, halo, cyano, hydroxy, acetyl, C$_{1-5}$ alkyl, C$_{1-4}$ alkoxy, and NR$_c$R$_d$ wherein R$_c$ and R$_d$ are independently H or C$_{1-3}$ alkyl, provided that R$_3$ and R$_4$ are not both H; and
n is 1 or 2;
or a pharmaceutically acceptable salt thereof.

Compounds of the present invention can also be selected from:
Acetic acid, [4-[[2-ethoxy-3-[4-(trifluoromethyl)phenoxy]propyl]thio]-2-methylphenoxy]-,
Acetic acid, [4-[[(2R)-2-ethoxy-3-[4-(trifluoromethyl)phenoxy]propyl]thio]-2-methylphenoxy]-, and
Acetic acid, [4-[[(2S)-2-ethoxy-3-[4-(trifluoromethyl)phenoxy]propyl]thio]-2-methylphenoxy]-.

Specifically, compounds of the present invention further include:
{2-Methyl-4-[2-(4-trifluoromethyl-phenoxymethyl)-butylsulfanyl]-phenoxy}-acetic acid;
{2-Methyl-4-[2-(4-trifluoromethyl-phenoxymethyl)-pentylsulfanyl]-phenoxy}-acetic acid;
{4-[4-Cyano-2-(4-trifluoromethyl-phenoxymethyl)-butylsulfanyl]-2-methyl-phenoxy}-acetic acid;
(R)-{4-[2-Allyloxy-3-(4-trifluoromethyl-phenoxy)-propylsulfanyl]-2-methyl-phenoxy}-acetic acid;
(R)-{4-[2-Methoxymethoxy-3-(4-trifluoromethyl-phenoxy)-propylsulfanyl]-2-methyl-phenoxy}-acetic acid;
{4-[2-Ethoxy-4-(4-trifluoromethyl-phenyl)-butylsulfanyl]-2-methyl-phenoxy}-acetic acid;
{3-Chloro-4-[2-ethoxy-3-(4-trifluoromethyl-phenoxy)-propylsulfanyl]-phenyl}-acetic acid;
{4-[2-Ethoxymethyl-3-(4-trifluoromethyl-phenoxy)-propylsulfanyl]-2-methyl-phenoxy}-acetic acid;
{4-[4-Ethoxy-2-(4-trifluoromethyl-phenoxymethyl)-butylsulfanyl]-2-methyl-phenoxy}-acetic acid;
{4-[2-(5-Chloro-thiophen-2-ylmethoxy)-3-(4-trifluoromethyl-phenoxy)-propylsulfanyl]-2-methyl-phenoxy}-acetic acid;
{4-[3-Cyano-2-(4-trifluoromethyl-phenoxymethyl)-propylsulfanyl]-2-methyl-phenoxy}-acetic acid;
{4-[5-Cyano-2-(4-trifluoromethyl-phenoxymethyl)-pent-4-enylsulfanyl]-2-methyl-phenoxy}-acetic acid;
{3-Chloro-4-[2-(4-trifluoromethyl-phenoxymethyl)-butylsulfanyl]-phenyl}-acetic acid;
{2-Methyl-4-[3-(4-trifluoromethyl-phenoxy)-2-(4-trifluoromethyl-phenoxymethyl)-propylsulfanyl]-phenoxy}-acetic acid;
{4-[2-Benzyloxy-3-(4-trifluoromethyl-phenoxy)-propylsulfanyl]-2-methyl-phenoxy}-acetic acid;
{4-[2-(4-Butyryl-phenoxy)-3-(4-trifluoromethyl-phenoxy)-propylsulfanyl]-2-methyl-phenoxy}-acetic acid;
{2-Methyl-4-[3-(4-trifluoromethyl-phenoxy)-propenylsulfanyl]-phenoxy}-acetic acid;
{2-Methyl-4-[2-methylsulfanylmethoxy-4-(4-trifluoromethyl-phenyl)-butylsulfanyl]-phenoxy}-acetic acid;
{4-[2,4-Diethoxy-4-(4-trifluoromethyl-phenyl)-butylsulfanyl]-2-methyl-phenoxy}-acetic acid;
{4-[2-Ethoxy-4-(4-trifluoromethyl-phenyl)-but-3-enylsulfanyl]-2-methyl-phenoxy}-acetic acid;
{4-[2-(4-Trifluoromethyl-phenoxymethyl)-butylsulfanyl]-phenoxy}-acetic acid;
{2-Methyl-4-[2-(4-trifluoromethyl-phenoxymethyl)-heptylsulfanyl]-phenoxy}-acetic acid;
{4-[4-Methoxy-2-(4-trifluoromethyl-phenoxymethyl)-butylsulfanyl]-2-methyl-phenoxy}-acetic acid;
{2-Methyl-4-[3-(4-trifluoromethyl-phenoxy)-propylsulfanyl]-phenoxy}-acetic acid;
{2-Methyl-4-[4-(4-trifluoromethyl-phenyl)-3,6-dihydro-2H-pyran-2-ylmethylsulfanyl]-phenoxy}-acetic acid;

{2-Methyl-4-[4-(4-trifluoromethyl-phenyl)-but-3-enyl-sulfanyl]-phenoxy}-acetic acid;
(R)-{4-[2-Ethoxy-3-(4-trifluoromethoxy-phenoxy)-propylsulfanyl]-2-methyl-phenoxy}-acetic acid;
(R)-{4-[3-(4-Chloro-phenoxy)-2-ethoxy-propylsulfanyl]-2-methyl-phenoxy}-acetic acid;
(R)-{4-[3-(4-tert-Butyl-phenoxy)-2-ethoxy-propylsulfanyl]-2-methyl-phenoxy}-acetic acid;
(R)-{2-Methyl-4-[2-(4-trifluoromethoxy-phenoxymethyl)-butylsulfanyl]-phenoxy}-acetic acid;
(R)-{4-[2-(4-Chloro-phenoxymethyl)-butylsulfanyl]-2-methyl-phenoxy}-acetic acid;
(R)-{4-[2-(4-tert-Butyl-phenoxymethyl)-butylsulfanyl]-2-methyl-phenoxy}-acetic acid;
(R)-{3-Chloro-4-[2-ethoxy-3-(4-trifluoromethoxy-phenoxy)-propylsulfanyl]-phenyl}-acetic acid;
(R)-{3-Chloro-4-[3-(4-chloro-phenoxy)-2-ethoxy-propylsulfanyl]-phenyl}-acetic acid;
(R)-{4-[2-Ethoxy-3-(4-trifluoromethyl-phenoxy)-propylsulfanyl]-2-methyl-phenylsulfanyl}-acetic acid;
(R)-{4-[2-Ethoxy-3-(4-trifluoromethoxy-phenoxy)-propylsulfanyl]-2-methyl-phenylsulfanyl}-acetic acid;
(R)-{2-Methyl-4-[2-(4-trifluoromethyl-phenoxymethyl)-butylsulfanyl]-phenylsulfanyl}-acetic acid;
(R)-{2-Methyl-4-[2-(4-trifluoromethoxy-phenoxymethyl)-butylsulfanyl]-phenylsulfanyl}-acetic acid;
Acetic acid, {4-[(2R)-2-hydroxy-3-(4-trifluoromethyl-phenoxy)-propylsulfanyl]-2-methyl-phenoxy}-;
Acetic acid, {4-[(2S)-2-hydroxy-3-(4-trifluoromethyl-phenoxy)-propylsulfanyl]-2-methyl-phenoxy}-; and
{4-[2-Ethoxy-3-(4-trifluoromethyl-phenoxy)-propoxy]-2-methyl-phenoxy}-acetic acid.

The present invention also provides compositions containing and methods of using compounds of Formula (I). In particular, the present invention provides compositions containing and methods of using compounds of Formula (I) as exemplified above.

Examples of preferred compounds include those described in Table 1 below.

TABLE 1

| Compound Number | Structure |
|---|---|
| 1 | ![structure] |
| 2 | ![structure] |
| 3 | ![structure] |
| 4 | ![structure] |
| 5 | ![structure] |
| 6 | ![structure] |
| 7 | ![structure] |
| 8 | ![structure] |
| 9 | ![structure] |
| 10 | ![structure] |

TABLE 1-continued

| Compound Number | Structure |
|---|---|
| 11 | 4-[(2-{[(4-(trifluoromethyl)phenoxy)methyl]-4-cyanobutyl}sulfanyl)]-2-methylphenoxyacetic acid (HO₂C-CH₂-O-Ar(Me)-S-CH₂-CH(CH₂-O-C₆H₄-CF₃)-CH₂-CH₂-CN) |
| 12 | HO₂C-CH₂-O-Ar(Me)-S-CH₂-CH(CH₂-O-C₆H₄-CF₃)-CH₂-CH=CH-CN |
| 13 | HO₂C-CH₂-O-Ar(Me)-S-CH₂-CH(OH)-CH₂-O-C₆H₄-CF₃ |
| 14 | HO₂C-CH₂-O-Ar(Me)-S-CH₂-CH(OMe)-CH₂-O-C₆H₄-CF₃ |
| 15 | HO₂C-CH₂-O-Ar(Me)-S-CH₂-CH(OEt)-CH₂-O-C₆H₄-CF₃ (S) |
| 16 | HO₂C-CH₂-O-Ar(Me)-S-CH₂-CH(OEt)-CH₂-O-C₆H₄-CF₃ (R) |
| 17 | HO₂C-CH₂-O-Ar(Me)-S-CH₂-CH(OEt)-CH₂-O-C₆H₄-CF₃ |
| 18 | HO₂C-CH₂-O-Ar(Me)-S-CH₂-CH(O-propyl)-CH₂-O-C₆H₄-CF₃ |
| 19 | HO₂C-CH₂-O-Ar(Me)-S-CH₂-CH(O-butyl)-CH₂-O-C₆H₄-CF₃ |
| 20 | HO₂C-CH₂-O-Ar(Me)-S-CH₂-CH(O-allyl)-CH₂-O-C₆H₄-CF₃ (stereo) |
| 21 | HO₂C-CH₂-O-Ar(Me)-S-CH₂-CH(O-allyl)-CH₂-O-C₆H₄-CF₃ |
| 22 | HO₂C-CH₂-O-Ar(Me)-S-CH₂-CH(OCH₂OMe)-CH₂-O-C₆H₄-CF₃ (stereo) |
| 23 | HO₂C-CH₂-O-Ar(Me)-S-CH₂-CH(OCH₂OMe)-CH₂-O-C₆H₄-CF₃ (stereo) |

TABLE 1-continued

| Compound Number | Structure |
|---|---|
| 24 | HO₂C-O-(2-methylphenyl)-S-CH₂-CH(OCH₂OCH₃)-CH₂-O-(4-CF₃-phenyl) |
| 25 | HO₂C-O-(2-methylphenyl)-S-CH₂-CH(OCH₂SCH₃)-CH₂-O-(4-CF₃-phenyl) |
| 26 | HO₂C-O-(2-methylphenyl)-S-CH₂-CH(OCH₂CO₂H)-CH₂-O-(4-CF₃-phenyl) |
| 27 | HO₂C-O-(2-methylphenyl)-S-CH₂-CH(OCH₂-(5-chlorothiophen-2-yl))-CH₂-O-(4-CF₃-phenyl) |
| 28 | HO₂C-O-(2-methylphenyl)-S-CH₂-CH(OBn)-CH₂-O-(4-CF₃-phenyl) |
| 29 | HO₂C-O-(2-methylphenyl)-S-CH₂-CH(O-(4-OMe-phenyl))-CH₂-O-(4-CF₃-phenyl) |
| 30 | HO₂C-O-(2-methylphenyl)-S-CH₂-CH(O-(4-butyryl-phenyl))-CH₂-O-(4-CF₃-phenyl) |
| 31 | HO-C(O)-CH₂-O-(2-methylphenyl)-S-CH₂-CH(OH)-CH₂-O-(4-methylphenyl) |
| 32 | HO₂C-CH₂-(3-chlorophenyl)-S-CH₂-CH(OEt)-CH₂-O-(4-CF₃-phenyl) |
| 33 | HO₂C-O-(2-methylphenyl)-S-CH₂-CH(CH₂OEt)-CH₂-O-(4-CF₃-phenyl) |
| 34 | HO₂C-O-(2-methylphenyl)-S-CH₂-CH(CH₂O-(4-CF₃-phenyl))-CH₂-O-(4-CF₃-phenyl) |
| 35 | HO₂C-O-(2-methylphenyl)-S-CH₂-CH(CH₂CH₂OMe)-CH₂-O-(4-CF₃-phenyl) |

TABLE 1-continued

| Compound Number | Structure |
|---|---|
| 36 | HO₂C-O-[aryl(Me)]-S-CH₂-CH(CH₂OAr-CF₃)-CH₂-CH(OEt)₂ |
| 37 | HO₂C-O-[aryl(Me)]-S-CH₂-CH(CH₂OAr-CF₃)-CH₂-CH₂-OEt |
| 38 | HO₂C-O-[aryl(Me)]-S-CH₂-CH(OEt)-CH₂-O-Ar-CF₃ |
| 39 | HO₂C-O-[aryl(Me)]-S-CH₂-CH(OCH₂SMe)-CH₂-O-Ar-CF₃ |
| 40 | HO₂C-O-[aryl(Me)]-S-CH₂-CH=CH-Ar-CF₃ |
| 41 | HO₂C-O-[aryl(Me)]-S-CH₂-CH(OH)-CH=CH-Ar-CF₃ |
| 42 | HO₂C-O-[aryl(Me)]-S-CH₂-CH(OEt)-CH=CH-Ar-CF₃ |
| 43 | HO₂C-O-[aryl(Me)]-S-CH₂-CH(OH)-CH₂-O-Ar-CF₃ (S config) |
| 44 | HO₂C-O-[aryl(Me)]-O-CH₂-CH(OEt)-CH₂-O-Ar-CF₃ |
| 45 | HO₂C-O-[aryl(Me)]-O-CH₂-CH(OH)-CH₂-O-Ar-CF₃ |

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1-19, which is incorporated herein by reference. Representative pharmaceutically acceptable amides of the invention include those derived from ammonia, primary $C_{1-6}$ alkyl amines and secondary di ($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(Imidazol-1-ylmethyl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl) methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridy)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N—(N',N'-dimethylaminomethylene).

Protection for the Carboxyl Group

Esters

Examples of esters include formate, benzoylformate, acetate, trichloroacetate, trifluoroacetate, methoxyacetate, phenoxyacetate, p-chlorophenoxyacetate, benzoate.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl) ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

C. SYNTHESIS

The invention provides methods of making the disclosed compounds according to traditional organic synthetic methods as well as matrix or combinatorial synthetic methods. Schemes 1 through 3 describe suggested synthetic routes. Using these Schemes, the guidelines below, and the examples, a person of skill in the art may develop analogous or similar methods for a given compound that are within the invention. These methods are representative of the preferred synthetic schemes, but are not to be construed as limiting the scope of the invention.

One skilled in the art will recognize that synthesis of the compounds of the present invention may be effected by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a chiral HPLC column.

Examples of the described synthetic routes include Examples 1 through 9. Compounds analogous to the target compounds of these examples can be made according to similar routes. The disclosed compounds are useful in basic research and as pharmaceutical agents as described in the next section.

General Guidance

A preferred synthesis of Formula (I) is demonstrated in Schemes 1-9.

Abbreviations or acronyms useful herein include: AcOH (glacial acetic acid); DCC (1,3-dicyclohexylcarbodiimide); DCE (1,2-dichloroethane); DIC (2-dimethylaminoisopropyl chloride hydrochloride); DIEA (diisopropylethylamine); DMAP (4-(dimethylamino)pyridine); DMF (dimethylformamide); EDC (1-(3-dimethylaminopropyl)-3-ethylcarbodiimide); EtOAc (ethyl acetate); LAH (lithium aluminum hydride); mCPBA (3-chloroperoxybenzoic acid); NMI (1-methylimidazole); TEA (triethylamine); TFA (trifluoroacetic acid); THF (tetrahydrofuran); TMEDA (N,N,N',N'-tetramethyl-ethylenediamine).

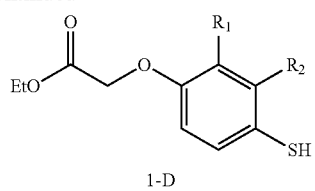

1-D

In accordance with Scheme 1, phenol 1-A, a variety of which are commercially available (such as 3-methylphenol, 2-ethylphenol, 2-propylphenol, 2,3-dimethylphenol, 2-chlorophenol, 2,3-dichlorophenol, 2-bromophenol, and 2-aminophenol), is alkylated to form phenoxyacetic acid ethyl ester 1-B with a suitable haloacetic acid ester such as bromoacetic acid ethyl ester, in the presence of an appropriate base such as $Cs_2CO_3$, $K_2CO_3$, or NaH, in a suitable solvent such as $CH_3CN$ or THF. Sulfonation of the phenoxyacetic acid ethyl ester 1-B with an appropriate sulfonating agent, such as chlorosulfonic acid, occurs selectively at the para position to provide 4-chlorosulfonylphenoxyacetic acid ethyl ester 1-C. Transformation of the sulfonylchloride 1-C to benzenethiol 1-D is accomplished using a metal as a reducing agent, such as tin or zinc, in an acidic medium such as ethanol or dioxane.

Scheme 1. Synthesis of Intermediate 1-D

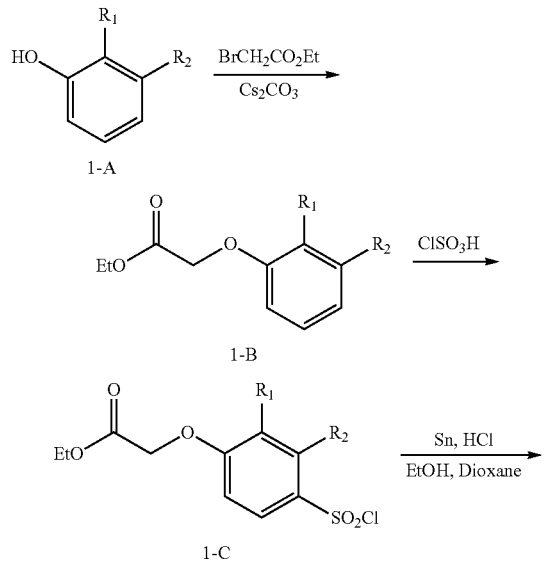

Scheme 2. Synthesis of Compound Ia

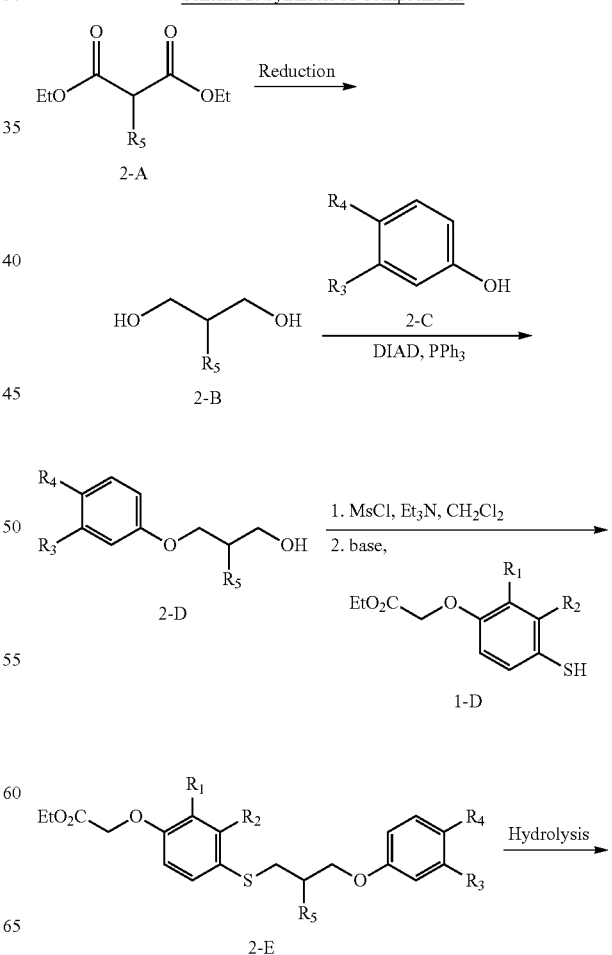

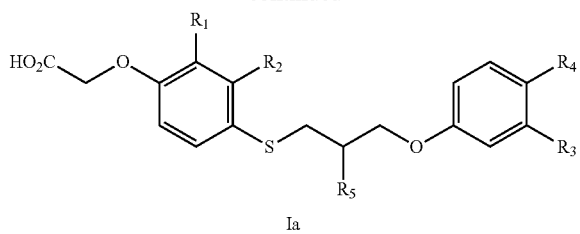

Ia

In Scheme 2, $R_5$ substituted diethyl malonate 2-A is reduced to propane-1,3-diol 2-B by using a suitable reducing agent such as lithium aluminum hydride or diisobutylaluminum hydride. Mitsunobu reaction of 2-B with phenol 2-C provides compound 2-D by employing a triarylphosphine such as triphenylphosphine, and an azodicarbonyl reagent such as diisopropyl azodicarboxylate, in a suitable solvent such as THF. Phenoxyacetic acid ethyl ester 2-E is obtained in two steps: (1) conversion of the alcohol 2-D to mesylate under standard conditions by employing methanesulfonyl chloride and triethylamine in an appropriate solvent such as $CH_2Cl_2$, and (2) alkylation of benzenethiol 1-D, prepared according to Scheme 1 above, with the mesylate intermediate using a suitable base such as $Cs_2CO_3$, $K_2CO_3$, or NaH, in an appropriate solvent such as $CH_3CN$ or THF, under nitrogen. Under standard saponification conditions phenoxyacetic acid ethyl ester 2-E is converted to acid Ia under nitrogen. The preferred hydrolysis conditions include using NaOH as a base in an aqueous alcoholic solvent system such as water-methanol, or using LiOH as a base in a milder water-THF system.

Scheme 3. Synthesis of Compound Ia1

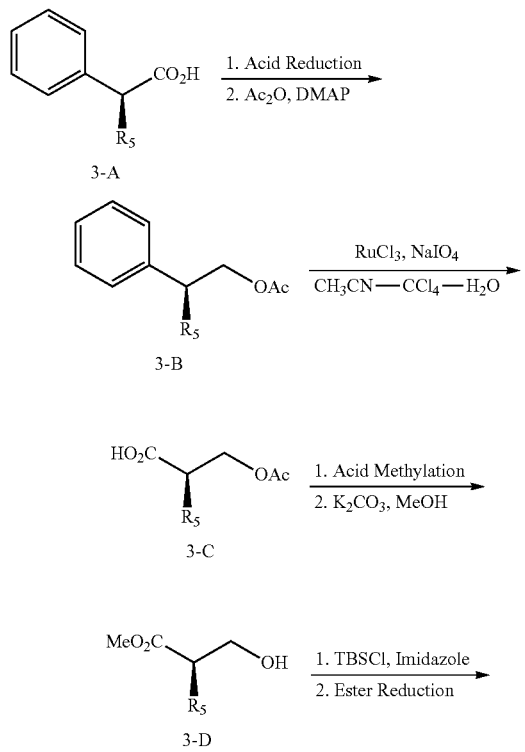

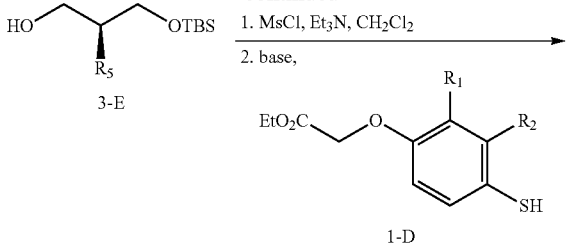

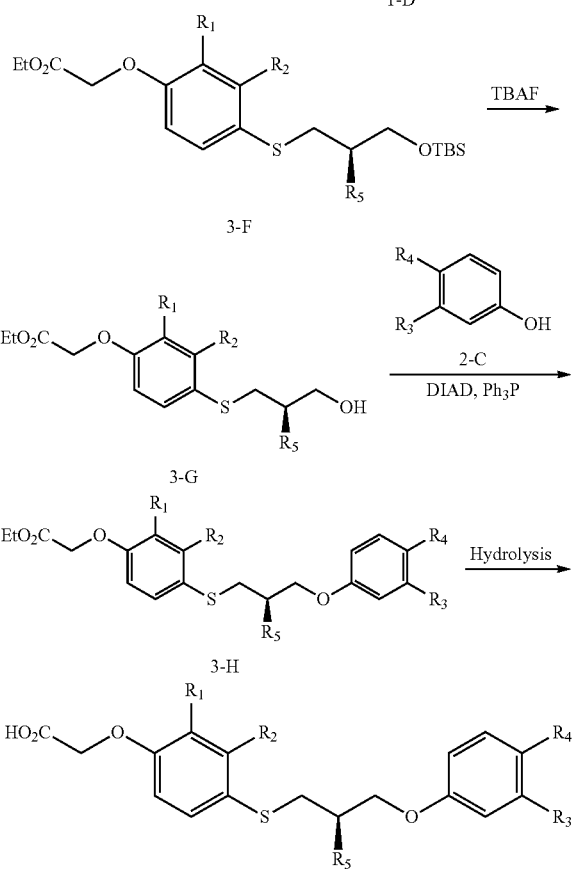

In Scheme 3, enantiomerically pure phenylacetic acid 3-A, a variety of which are commercially available (such as (S)-(+)-2-phenylpropionic acid, (R)-(−)-2-phenylpropionic acid, (S)-(+)-2-phenylbutyric acid, (R)-(−)-2-phenylbutyric acid, (+)-3-methyl-2-phenylbutyric acid, (S)-(+)-2-phenylsuccinic acid, and (R)-(−)-2-phenylsuccinic acid), is reduced to alcohol by using borane and the alcohol is subsequently protected as an acetate 3-B under standard conditions known in arts. Oxydation of the phenyl group in 3-B to acid 3-C is accomplished by employing catalytic amount of ruthenium chloride and a large excess of sodium periodate in a mixed solvent system such as $CH_3CN$—$CCl_4$—$H_2O$. Acid 3-C is converted to alcohol 3-E in four steps: (1) methylation of acid 3-C using (trimethysilyl)diazomethane as a methylating agent, (2) and (3) exchanging of the hydroxyl protecting group from acetate in 3-C to tert-butyldimethyl silyloxy in 3-E under conventional conditions well known in arts, and (4) reduction of methyl ester by using an appropriate reducing agent such as diisobutylaluminum hydride.

Phenoxyacetic acid ethyl ester 3-F is obtained in two steps: (1) conversion of the alcohol 3-E to mesylate under standard conditions by employing methanesulfonyl chloride and triethylamine in an appropriate solvent such as CH$_2$Cl$_2$, and (2) alkylation of benzenethiol 1-D, prepared according to Scheme 1 above, with the mesylate intermediate using a suitable base such as Cs$_2$CO$_3$, K$_2$CO$_3$, or NaH, in an appropriate solvent such as CH$_3$CN or THF, under nitrogen. After revealing of the hydroxyl group by removal of the tert-butyldimethyl silyloxy group in 3-F, alcohol 3-G is transformed to 3-H by reacting with phenol 2-C under Mitsunobu conditions. The preferred conditions include using a triarylphosphine such as triphenylphosphine, and an azodicarbonyl reagent such as diisopropyl azodicarboxylate, in a suitable solvent such as THF. Under standard saponification conditions phenoxyacetic acid ethyl ester 3-H is converted to acid Ia1 under nitrogen. The preferred hydrolysis conditions include using NaOH as a base in an aqueous alcoholic solvent system such as water-methanol, or using LiOH as a base in a milder water-THF system.

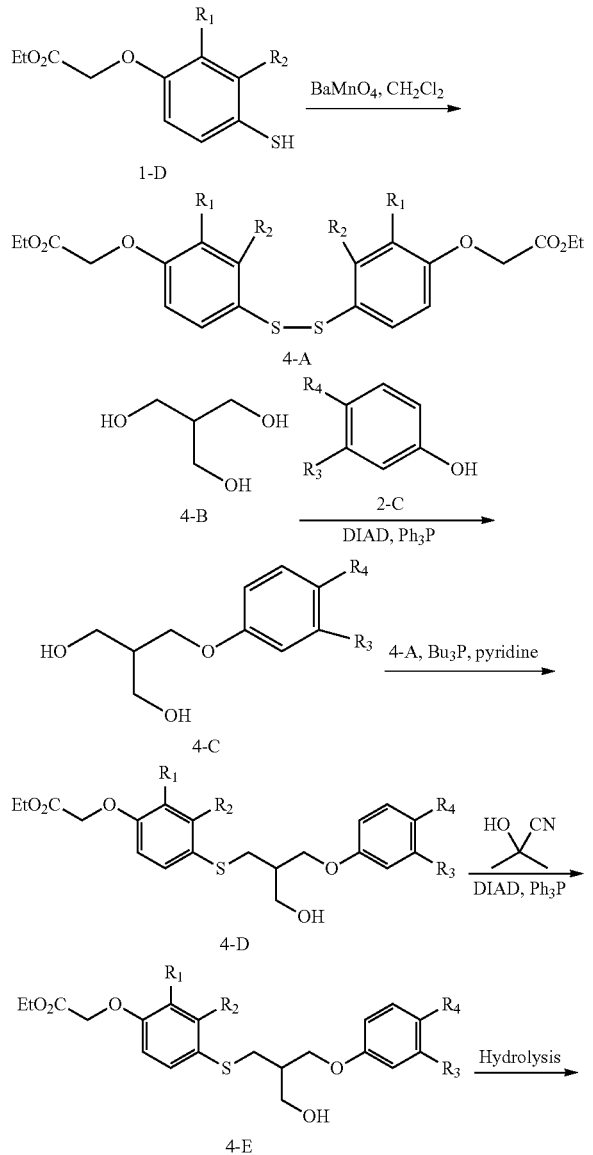

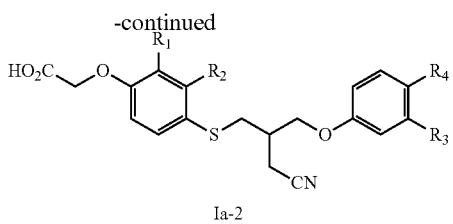

In Scheme 4, benzenethiol 1-D is dimerized to phenyl disulfide 4-A in the presence of an appropriate oxidizing agent such as barium manganate.

Mitsunobu reaction of 2-hydroxymethylpropane-1,3-diol 4-B with phenol 2-C provides compound 4-C by employing a triarylphosphine such as triphenylphosphine, and an azodicarbonyl reagent such as diisopropyl azodicarboxylate, in a suitable solvent such as THF. The formation of carbon-sulfur bond in compound 4-D is carried out by Mitsunobu reaction of diol 4-C with phenyl disulfide 4-A by using tri-n-butylphosphine and pyridine. The third Mitsunobu reaction of 4-D with acetone cyanohydrin converted the alcohol 4-D to the cyano compound 4-E under standard Mitsunobu reaction conditions. As usual, basic hydrolysis of phenoxyacetic acid ethyl ester 4-E affords acid Ia2.

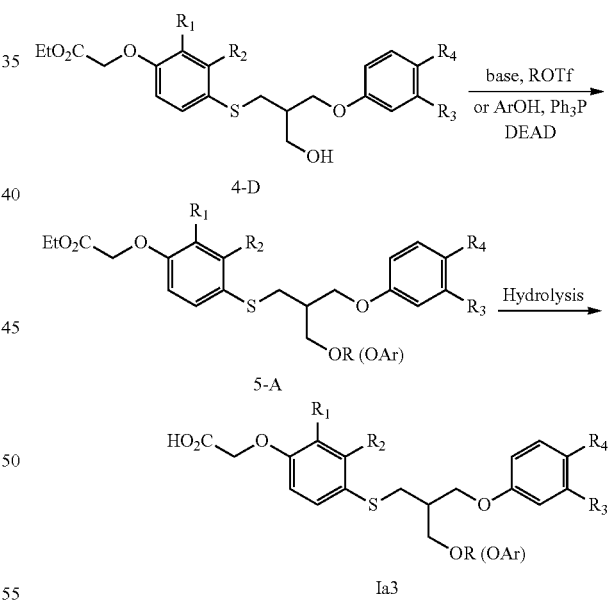

As shown in Scheme 5, wherein R is alkyl or aryl, alkyl ether compound 5-A could be prepared by alkylation of alcohol 4-D, an intermediate prepared in Scheme 4 above, with a variety of alkylating agents such as alkyl trifluoromethanesulfonates or alkyl halides in the presence of a suitable base such as sodium hydride or sodium bis(trimethylsilyl)amide. Similarly, aryl ether could be synthesized by Mitsunobu reaction of 4-D with many different substituted phenols available. Finally, saponification of ethyl ester 5-A under standard conditions gives acid Ia3.

Scheme 6. Synthesis of Compound Ia4

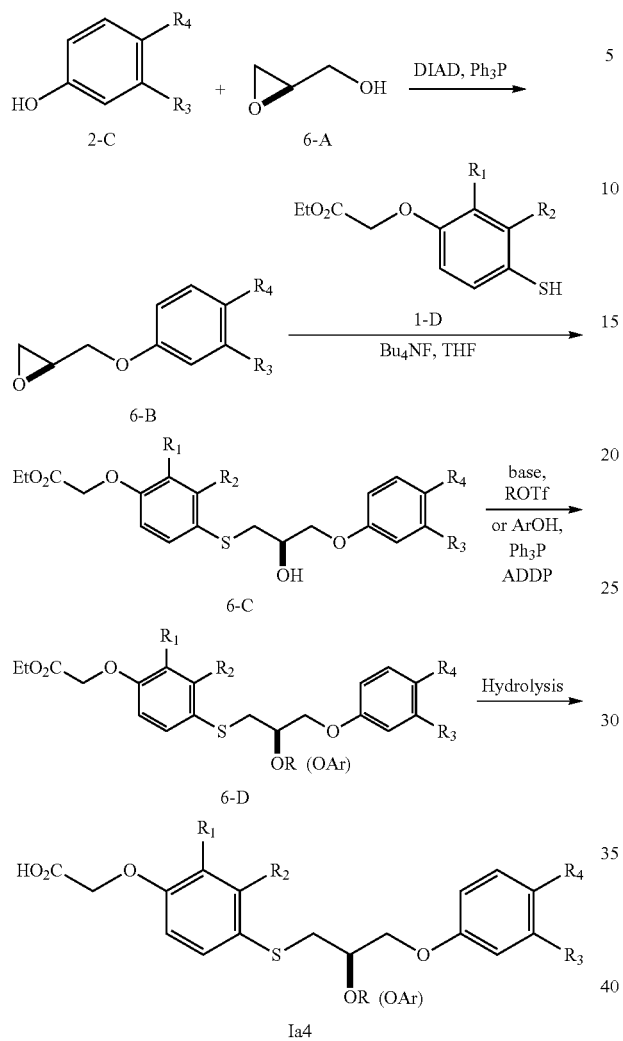

Scheme 7. Synthesis of Intermediate 7-E

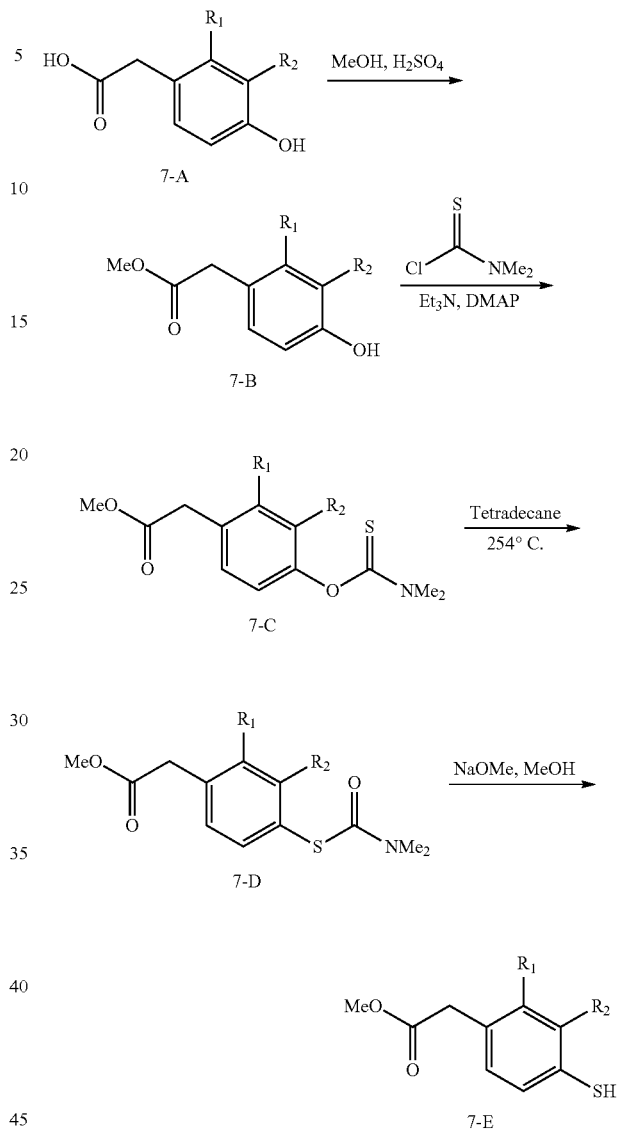

In accordance with Scheme 6, Mitsunobu reaction of (R)-(+)-glycidol, or (S)-(−)-glycidol, or racemic glycidol 6-A with phenol 2-C provides epoxide 6-B by employing a triarylphosphine such as triphenylphosphine, and an azodicarbonyl reagent such as diisopropyl azodicarboxylate, in a suitable solvent such as THF. Epoxide ring opening of 6-B with benzenethiol 1-D in the presence of a catalytic amount of tetrabutylammonium fluoride furnishes alcohol 6-C. Alkyl ether compound 6-D could be prepared by alkylation of alcohol 6-C with a variety of alkylating agents such as alkyl trifluoromethanesulfonates or alkyl halides in the presence of a suitable base such as sodium hydride or sodium bis(trimethylsilyl)amide in a suitable solvent such as THF or DMF. Similarly, aryl ether 6-D could be synthesized by Mitsunobu reaction of 6-C with many different substituted phenols available by using triphenylphosphine and an appropriate azodicarbonyl reagent such as 1,1'-(azodicarbonyl) dipiperidine or diethyl azodicarboxylate. Finally, saponification of ethyl ester 6-D under standard conditions gives acid Ia4.

In accordance with Scheme 7, (4-hydroxyphenyl) acetic acid 7-A, a variety of which are commercially available (such as 3-bromo-4-hydroxyphenyl acetic acid, 3-chloro-4-hydroxyphenyl acetic acid, 3-fluoro-4-hydroxyphenyl acetic acid, 4-hydroxy-3-methoxyphenyl acetic acid, and 4-hydroxy-3-nitrophenyl acetic acid), is methylated to form (4-hydroxyphenyl) acetic acid methyl ester 7-B in methanol in the presence of a catalytic amount of a suitable acid such as sulfuric acid or hydrochloric acid. The phenol 7-B is converted to (4-dimethylthiocarbamoyloxyphenyl) acetic acid methyl ester 7-C by reacting with dimethylthiocarbamoyl chloride in the presence of some appropriate bases such as triethylamine and 4-(dimethylamino)pyridine. At high temperature, in the preferred range of 250 to 300° C., 7-C is rearranged to (4-dimethylcarbamoylsulfanylphenyl) acetic acid methyl ester 7-D in a high boiling point solvent such as tetradecane. By treatment with a suitable base such as sodium methoxide 7-D is transformed to (4-mercaptophenyl) acetic acid methyl ester 7-E.

Scheme 8. Synthesis of Compound Ib1

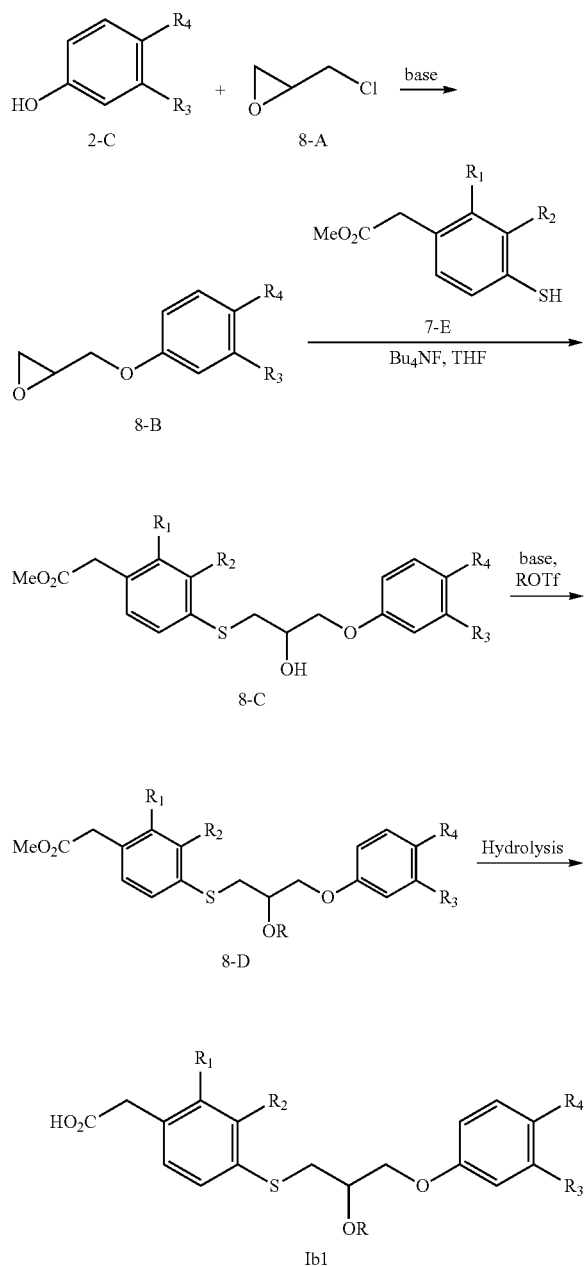

Scheme 8. Synthesis of Compound Ic1

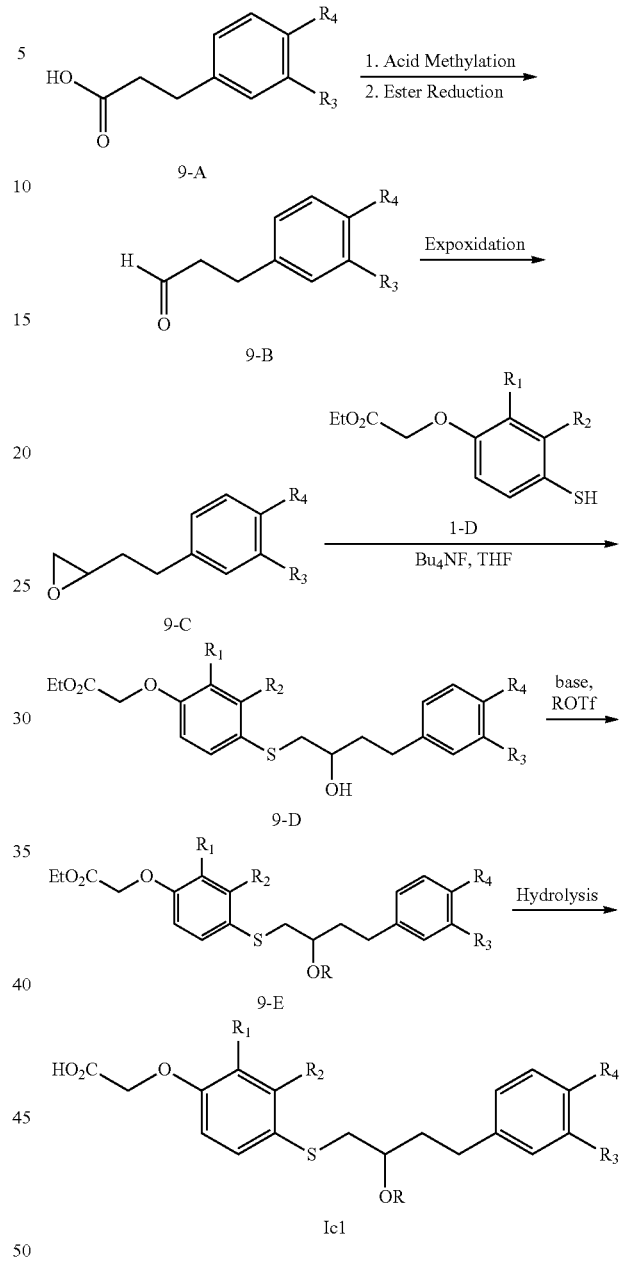

In accordance with Scheme 8, wherein R is alkyl, epoxide 8-B is obtained by treatment of phenol 2-C with an appropriate base such as cesium carbonate followed by alkylation with 2-chloromethyl-oxirane 8-A. Epoxide ring opening of 8-B with benzenethiol 7-E, prepared in Scheme 7 above, in the presence of a catalytic amount of tetrabutylammonium fluoride furnishes alcohol 8-C. Alkyl ether compound 8-D could be prepared by alkylation of alcohol 8-C with a variety of alkylating agents such as alkyl trifluoromethanesulfonates or alkyl halides in the presence of a suitable base such as sodium hydride or sodium bis(trimethylsilyl)amide in a suitable solvent such as THF or DMF. Finally, saponification of methyl ester 8-D under standard conditions gives acid Ib1.

In Scheme 9, wherein R is as shown above, aldehyde 9-B could be prepared in two steps by methylation of acid 9-A using (trimethysilyl)diazomethane as a methylating agent followed by reduction of the methyl ester intermediate with a suitable reducing agent such as diisobutylaluminum hydride. Aldehyde 9-B is transformed to epoxide 9-C by reacting with dimethylsulfonium methylide, which is generated in-situ from treatment of trimethylsulfonium iodide with a strong base such as DMSO anion. Epoxide ring opening of 9-C with benzenethiol 1-D in the presence of a catalytic amount of tetrabutylammonium fluoride furnishes alcohol 9-D. Alkyl ether compound 9-E could be prepared by alkylation of alcohol 9-D with a variety of alkylating agents such as alkyl trifluoromethanesulfonates or alkyl halides in the presence of a suitable base such as sodium hydride or sodium bis(trimethylsilyl)amide in a suitable solvent such as THF or DMF. Finally, saponification of ethyl ester 9-E under standard conditions gives acid Ic1.

EXAMPLES

Example A

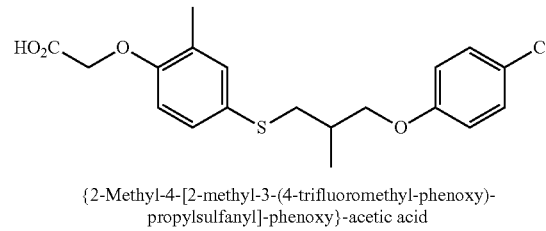

Compound 1

{2-Methyl-4-[2-methyl-3-(4-trifluoromethyl-phenoxy)-propylsulfanyl]-phenoxy}-acetic acid

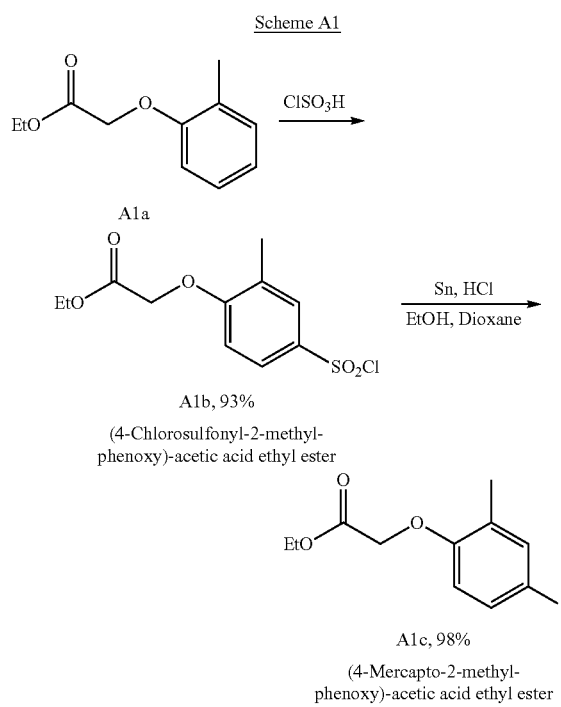

Scheme A1

A1a

A1b, 93%
(4-Chlorosulfonyl-2-methyl-phenoxy)-acetic acid ethyl ester

A1c, 98%
(4-Mercapto-2-methyl-phenoxy)-acetic acid ethyl ester

According to Scheme A1, to a flask containing chlorosulfonic acid (15.0 mL, 226 mmol) at 4° C. was added ethyl (2-methylphenoxy)acetate A1a (10.0 g, 51.6 mmol) slowly. The mixture was stirred at 4° C. for 30 min and room temperature for 2 h, and then poured into ice water. The precipitated white solid was filtered, washed with water, and dried under vacuum overnight to provide 14.0 g (93%) of A1b as a white solid; 1H NMR (300 MHz, CDCl$_3$) δ 7.87-7.84 (m, 2H), 6.80 (d, J=9.5 Hz, 1H), 4.76 (s, 2H), 4.29 (q, J=7.1 Hz, 2H), 2.37 (s, 3H), 1.31 (t, J=7.1 Hz, 3H); MS (ES) m/z: 315 (M+Na+).

To a solution of A1b (4.70 g, 16.1 mmol) in EtOH (20 mL) was added a solution of 4.0 M HCl in dioxane (20 mL) followed by 100 mesh tin powder (9.80 g, 82.6 mmol) portionwise. The mixture was refluxed for 2 h, poured into CH$_2$Cl$_2$/ice (100 mL), and filtered. The filtrate was separated, and the aqueous layer was extracted with CH$_2$Cl$_2$. The combined organic phases were washed with water, dried, and concentrated to give 3.56 g (98%) of A1c as a yellow oil; 1H NMR (300 MHz, CDCl$_3$) δ 7.14-7.03 (m, 2H), 6.59 (d, J=8.4 Hz, 1H), 4.60 (s, 2H), 4.25 (q, J=7.1 Hz, 2H), 2.24 (s, 3H), 1.29 (t, J=7.1 Hz, 3H).

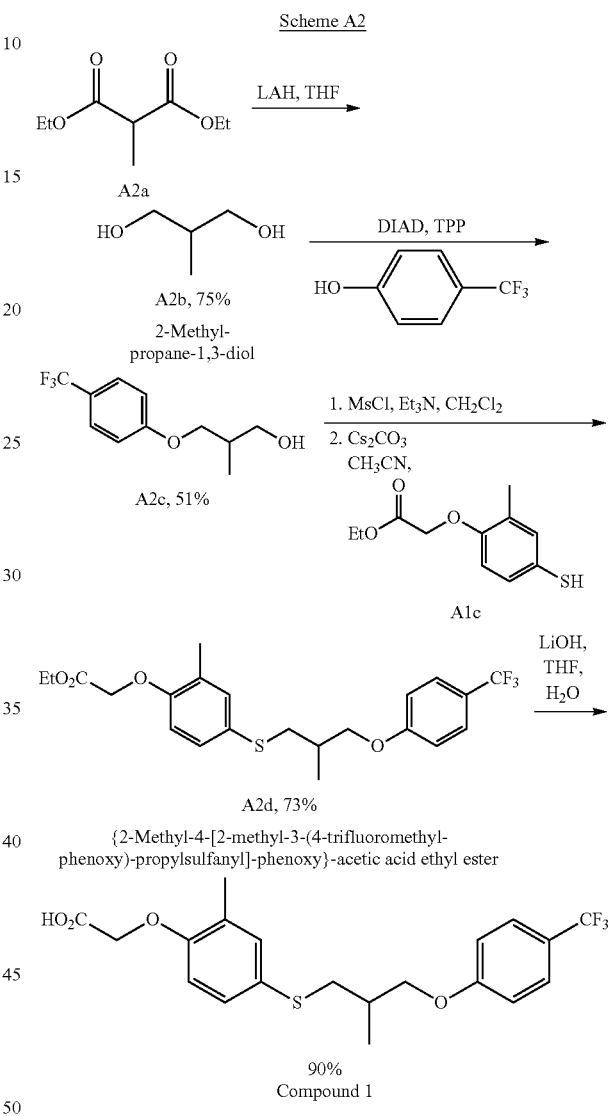

Scheme A2

A2a

A2b, 75%
2-Methyl-propane-1,3-diol

A2c, 51%

A1c

A2d, 73%
{2-Methyl-4-[2-methyl-3-(4-trifluoromethyl-phenoxy)-propylsulfanyl]-phenoxy}-acetic acid ethyl ester 90%
Compound 1

According to Scheme A2, to a suspension of lithium aluminum hydride (152 mg, 4.00 mmol) in THF (3 mL) at 0° C. was added diethyl methylmalonate A2a (348 mg, 2.00 mmol) dropwise. The reaction mixture was stirred at room temperature for 1.5 h, quenched with water (0.2 mL) and 5 N NaOH (0.2 mL), and further diluted with water (0.6 mL). After stirring for 20 min, the precipitated solid was filtered through Celite and washed with MeOH/CH$_2$Cl$_2$. The filtrate was dried, concentrated, and purified by column chromatography to give 135 mg (75%) of A2b; 1H NMR (300 MHz, CDCl$_3$) δ 3.68 (dd, J=10.7, 4.5 Hz, 2H), 3.58 (dd, J=10.7, 7.6 Hz, 2H), 3.50 (s, 2H), 1.96-1.89 (m, 1H), 0.86 (d, J=7.0 Hz, 3H); MS (ES) m/z: 113 (M+Na+).

To a mixture of A2b (113 mg, 1.26 mmol), trifluoromethylphenol (156 mg, 0.963 mmol), and triphenylphosphine (252 mg, 0.962 mmol) in THF (3 mL) at 0° C. was added diisopropyl azodicarboxylate (195 mg, 0.965 mmol). The mixture was stirred at room temperature overnight and concentrated. The residue was purified by column chromatography to provide 149 mg (51%) of A2c; 1H NMR (400 MHz, CDCl$_3$) δ 7.53 (d, J=8.8 Hz, 2H), 6.96 (d, J=8.7 Hz, 2H), 3.98 (m, 2H), 3.71 (m, 2H), 2.24-2.16 (m, 1H), 1.80 (s, 1H), 1.05 (d, J=7.0 Hz, 3H); MS (ES) m/z: 235 (M+H+).

General Procedure 1 for the Formation of Thioether:

To a solution of A2c (135 mg, 0.577 mmol) in CH$_2$Cl$_2$ (3 mL) at 0° C. were added Et$_3$N (0.162 mL, 1.16 mmol) and methanesulfonyl chloride (93 mg, 0.81 mmol). The mixture was stirred at 0° C. for 30 min and room temperature for 1 h and diluted with saturated NaHCO$_3$. The organic layer was separated and the aqueous layer was extracted with CH$_2$Cl$_2$ (×3). The combined organic phases were dried and concentrated to provide the mesylate.

A mixture of the above mesylate, (4-mercapto-2-methyl-phenoxy)acetic acid ethyl ester A1c (197 mg, 0.872 mmol), and Cs$_2$CO$_3$ (472 mg, 1.45 mmol) in CH$_3$CN (5 mL) was stirred at room temperature for 3 h. Water was added and the mixture was extracted with Et$_2$O. The combined organic layers were dried, concentrated, and column chromatographed (EtOAc/hexane: 1/10) to provide 187 mg (73%, two steps) of A2d; 1H NMR (300 MHz, CDCl$_3$) δ 7.51 (d, J=8.6 Hz, 2H), 7.20 (d, J=1.7 Hz, 1H), 7.15 (dd, J=8.4, 2.2 Hz, 1H), 6.89 (d, J=8.6 Hz, 2H), 6.57 (d, J=8.4 Hz, 1H), 4.57 (s, 2H), 4.25 (q, J=7.1 Hz, 2H), 3.94 (dd, J=5.7, 2.7 Hz, 2H), 3.04 (dd, J=13.6, 6.6 Hz, 1H), 2.86 (dd, J=13.3, 6.5 Hz, 1H), 2.24-2.16 (m, 1H), 2.23 (s, 3H), 1.29 (t, J=7.1 Hz, 3H), 1.14 (d, J=6.8 Hz, 3H); MS (ES) m/z: 465 (M+Na+).

General Procedure 2 for the Hydrolysis of the Ethyl and Methyl Esters:

To a solution of A2d (130 mg, 0.294 mmol) in THF (2 mL) under N$_2$ was added 1.0 M LiOH (0.58 mL, 0.58 mmol). The mixture was stirred for 2 h, acidified with 1 M HCl, and extracted with EtOAc (×3). The extracts were dried, concentrated, and purified by column chromatography (CH$_2$Cl$_2$/MeOH: 10/1) to give 109 mg (90%) of Compound 1; 1H NMR (400 MHz, CDCl$_3$) δ 7.50 (d, J=8.7 Hz, 2H), 7.18 (s, 1H), 7.14 (d, J=8.4 Hz, 1H), 6.88 (d, J=8.7 Hz, 2H), 6.57 (d, J=8.4 Hz, 1H), 4.57 (s, 2H), 3.92 (d, J=5.6 Hz, 2H), 3.04 (dd, J=13.3, 6.5 Hz, 1H), 2.85 (dd, J=13.2, 6.5 Hz, 1H), 2.24-2.15 (m, 1H), 2.19 (s, 3H), 1.13 (d, J=6.8 Hz, 3H); MS (ES) m/z: 415 (M+H+).

Example B

Compound 2

{2-Methyl-4-[2-(4-trifluoromethyl-phenoxymethyl)-butylsulfanyl]-phenoxy}-acetic acid

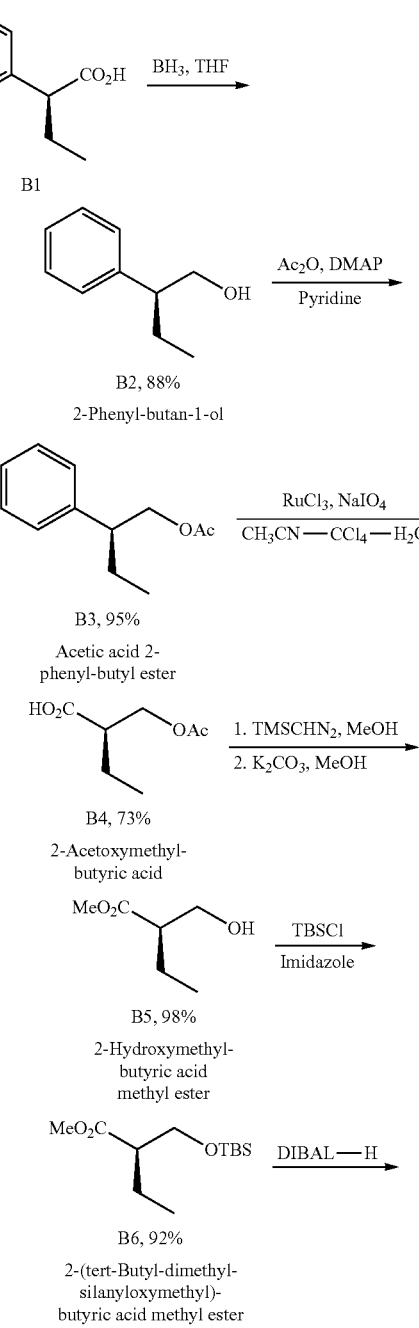

Scheme B

B1

B2, 88%
2-Phenyl-butan-1-ol

B3, 95%
Acetic acid 2-phenyl-butyl ester

B4, 73%
2-Acetoxymethyl-butyric acid

B5, 98%
2-Hydroxymethyl-butyric acid methyl ester

B6, 92%
2-(tert-Butyl-dimethyl-silanyloxymethyl)-butyric acid methyl ester

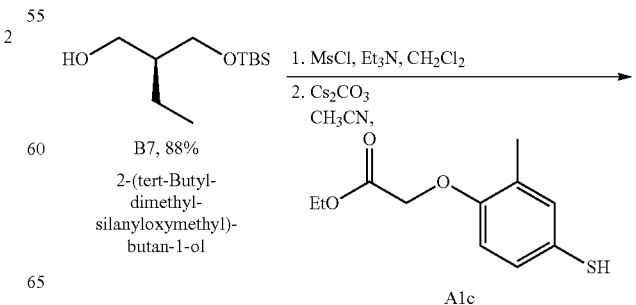

B7, 88%
2-(tert-Butyl-dimethyl-silanyloxymethyl)-butan-1-ol

A1c

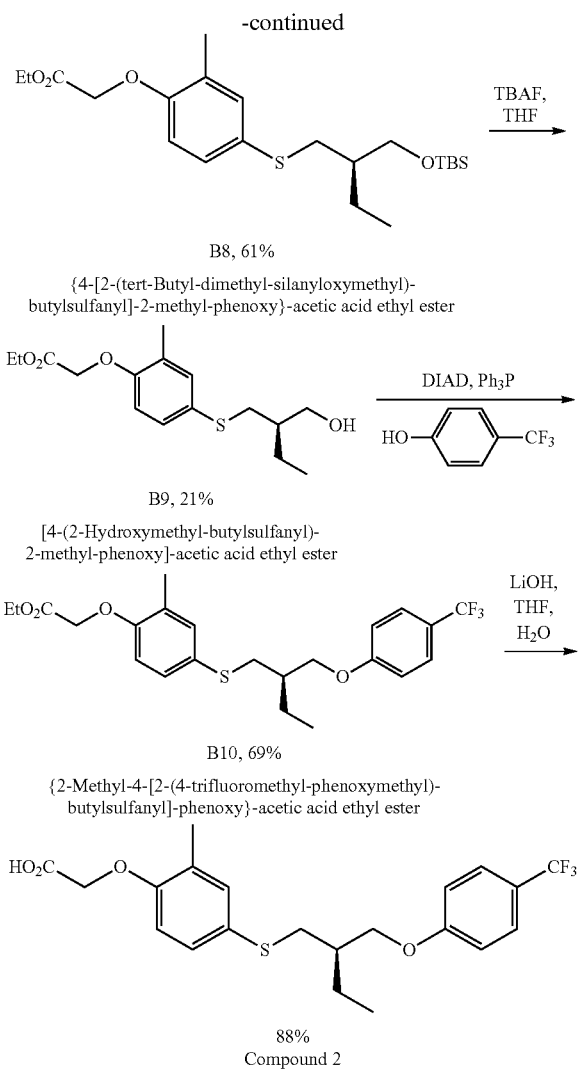

B8, 61%
{4-[2-(tert-Butyl-dimethyl-silanyloxymethyl)-butylsulfanyl]-2-methyl-phenoxy}-acetic acid ethyl ester B9, 21%
[4-(2-Hydroxymethyl-butylsulfanyl)-2-methyl-phenoxy]-acetic acid ethyl ester B10, 69%
{2-Methyl-4-[2-(4-trifluoromethyl-phenoxymethyl)-butylsulfanyl]-phenoxy}-acetic acid ethyl ester 88%
Compound 2

To a solution of (S)-(+)-2-phenylbutyric acid B1 (352 mg, 2.14 mmol) in THF (3 mL) at 0° C. was slowly added a solution of 1.0 M BH$_3$·THF complex in THF (2.14 mL, 2.14 mmol). The mixture was allowed to warm up to room temperature, stirred at room temperature overnight, quenched with water and followed by 1.0 N HCl, and extracted with Et$_2$O (×3). The extracts were dried, concentrated, and column chromatographed to give 283 mg (88%) of B2; 1H NMR (300 MHz, CDCl$_3$) δ 7.34-7.29 (m, 2H), 7.24-7.16 (m, 3H), 3.70 (m, 2H), 2.65 (m, 1H), 1.79-1.67 (m, 1H), 1.63-1.48 (m, 2H), 0.82 (t, J=7.4 Hz, 3H); MS (ES) m/z: 173 (M+Na+).

To a mixture of B2 (283 mg, 1.88 mmol), pyridine (0.76 mL, 9.4 mmol), and DMAP (23 mg, 0.19 mmol) in CH$_2$Cl$_2$ (3 mL) at 0° C. was added acetyl chloride (369 mg, 4.70 mmol). The mixture was stirred at room temperature for 2 h, diluted with 1.0 N HCl, and extracted with CH$_2$Cl$_2$. The combined organic phases were washed with 1.0 N HCl (×3) and brine, dried, concentrated, and column chromatographed to provide 343 mg (95%) of B3; 1H NMR (300 MHz, CDCl$_3$) δ 7.33-7.28 (m, 2H), 7.25-7.17 (m, 3H), 4.21 (m, 2H), 2.86-2.77 (m, 1H), 1.98 (s, 3H), 1.86-1.73 (m, 1H), 1.68-1.53 (m, 2H), 0.82 (t, J=7.4 Hz, 3H); MS (ES) m/z: 215 (M+Na+).

To a solution of B3 (160 mg, 0.833 mmol) in a mixture solvents of CCl$_4$ (2 mL), CH$_3$CN (2 mL), and water (3 mL) were added NaIO$_4$ (3.55 g, 16.6 mmol) and RuCl$_3$ (12 mg, 0.058 mmol). After stirring at room temperature overnight, the mixture was partitioned between water and CH$_2$Cl$_2$. The combined organic layers were dried, filtered, and concentrated. The residue was redissolved in Et$_2$O and filtered through Celite. The filtrate was dried and column chromatographed (CH$_2$Cl$_2$/MeOH: 9/1) to give 97 mg (73%) of B4; 1H NMR (300 MHz, CDCl$_3$) δ 4.24 (d, J=6.7 Hz, 2H), 2.67 (m, 1H), 2.06 (s, 3H), 1.77-1.56 (m, 2H), 1.00 (t, J=7.5 Hz, 3H); MS (ES) m/z: 183 (M+Na+).

To a solution of B4 (218 mg, 1.36 mmol) in Et$_2$O (4 mL) and MeOH (2 mL) was added 2.0 M TMSCHN$_2$ (2.08 mL, 4.16 mmol) in Et$_2$O slowly. After stirring at room temperature for 3 h, the solvents were removed under reduced pressure to give the methyl ester. To the dissolved residue in MeOH (2 mL) was added K$_2$CO$_3$ (188 mg, 1.36 mmol) and the resulted mixture was stirred for 20 min. After removal of solvent at low temperature, the residue was partitioned between Et$_2$O and water. The organic layer was dried, concentrated, and column chromatographed (EtOAc/hexane: ½) to afford 176 mg (98%) of B5; 1H NMR (300 MHz, CDCl$_3$) δ 3.82-3.73 (m, 2H), 3.73 (s, 3H), 2.53 (m, 1H), 2.41 (brs, 1H), 1.73-1.55 (m, 2H), 0.95 (t, J=7.5 Hz, 3H); MS (ES) m/z: 155 (M+Na+).

A mixture of B5 (225 mg, 1.70 mmol), tert-butyldimethylsilyl chloride (334 mg, 2.22 mmol), and imidazole (290 mg, 4.26 mmol) in DMF (1.7 mL) was stirred for 14 h and partitioned between water and Et$_2$O. The organic layer was dried, concentrated, and column chromatographed to provide 385 mg (92%) of B6; 1H NMR (400 MHz, CDCl$_3$) δ 3.77 (dd, J=9.7, 7.8 Hz, 1H), 3.70-3.66 (m, 1H), 3.68 (s, 3H), 2.52 (m, 1H), 1.64-1.51 (m, 2H), 0.91 (t, J=7.5 Hz, 3H), 0.87 (s, 9H), 0.03 (s, 6H); MS (ES) m/z: 269 (M+Na+).

To a solution of B6 (350 mg, 1.42 mmol) in CH$_2$Cl$_2$ (5 mL) at −78° C. was added 1.0 M DIBAL-H (3.55 mL, 3.55 mmol) dropwise. After stirring at −78° C. for 15 min, the mixture was allowed to gradually warm up to 0° C., stirred at the same temperature for 10 min, quenched with MeOH. After stirring at room temperature for 1 h, the precipitated solid was filtered through Celite and washed with CH$_2$Cl$_2$/MeOH. The filtrate was dried, concentrated, and column chromatographed to give 273 mg (88%) of B7; 1H NMR (300 MHz, CDCl$_3$) δ 3.82 (dd, J=9.9, 4.0 Hz, 1H), 3.75 (dd, J=11.0, 3.3 Hz, 1H), 3.67-3.58 (m, 2H), 2.78 (brs, 1H), 1.68-1.61 (m, 1H), 1.33-1.23 (m, 2H), 0.93 (t, J=7.4 Hz, 3H), 0.90 (s, 9H), 0.08 (s, 6H); MS (ES) m/z: 219 (M+H+).

B8 (61%) was prepared following general procedure 1 in Example A; 1H NMR (300 MHz, CDCl$_3$) δ 7.19 (d, J=1.8 Hz, 1H), 7.15 (dd, J=8.4, 2.2 Hz, 1H), 6.62 (d, J=8.4 Hz, 1H), 4.60 (s, 2H), 4.26 (q, J=7.1 Hz, 2H), 3.67 (dd, J=10.0, 4.7 Hz, 1H), 3.57 (dd, J=10.0, 5.5 Hz, 1H), 2.97 (dd, J=12.9, 6.8 Hz, 1H), 2.79 (dd, J=12.9, 6.0 Hz, 1H), 2.26 (s, 3H), 1.62-1.56 (m, 1H), 1.44 (m, 2H), 1.29 (t, J=7.1 Hz, 3H), 0.88 (t, J=7.4 Hz, 3H), 0.88 (s, 9H), 0.03 (s, 6H); MS (ES) m/z: 449 (M+Na+).

A solution of B8 (213 mg, 0.500 mmol) in CH$_2$Cl$_2$ (2 mL) was treated with a solution of 1.0 M tetrabutyl ammonium fluoride (1.50 mL, 1.50 mmol) in THF for 3 h and partitioned between water and CH$_2$Cl$_2$. The organic layer was dried, concentrated, and column chromatographed to provide 33 mg (21%) of B9; 1H NMR (300 MHz, CDCl$_3$) δ 7.22 (d, J=1.7 Hz, 1H), 7.17 (dd, J=8.4, 2.2 Hz, 1H), 6.63 (d, J=8.4 Hz, 1H), 4.61 (s, 2H), 4.25 (q, J=7.1 Hz, 2H), 3.72 (dd, J=10.9, 4.7 Hz, 1H), 3.64 (dd, J=11.0, 5.8 Hz, 1H), 2.92 (d, J=6.4 Hz, 2H), 2.26 (s, 3H), 1.73-1.63 (m, 2H), 1.45 (m, 2H), 1.29 (t, J=7.1 Hz, 3H), 0.91 (t, J=7.4 Hz, 3H); MS (ES) m/z: 335 (M+Na+).

To a mixture of B9 (120 mg, 0.385 mmol), trifluoromethylphenol (93 mg, 0.57 mmol), and triphenylphosphine (150 mg, 0.573 mmol) in THF (3 mL) at 0° C. was added diisopropyl azodicarboxylate (115 mg, 0.569 mmol). The mixture was stirred at room temperature overnight and concentrated. The residue was purified by column chromatography twice (EtOAc/hexane: 1/10; CH$_2$Cl$_2$/hexane: 2/1) to provide 121 mg (69%) of B10; 1H NMR (300 MHz, CDCl$_3$) δ 7.51 (d, J=8.7 Hz, 2H), 7.19 (d, J=1.8 Hz, 1H), 7.15 (dd, J=8.4, 2.3 Hz, 1H), 6.89 (d, J=8.6 Hz, 2H), 6.56 (d, J=8.4 Hz, 1H), 4.56 (s, 2H), 4.25 (q, J=7.1 Hz, 2H), 4.01 (m, 2H), 3.00 (d, J=6.4 Hz, 2H), 2.21 (s, 3H), 1.96 (m, 1H), 1.59 (m, 2H), 1.28 (t, J=7.1 Hz, 3H), 0.94 (t, J=7.4 Hz, 3H); MS (ES) m/z: 479 (M+Na+).

Compound 2 (88%) was prepared following general procedure 2 in Example A; 1H NMR (400 MHz, CDCl$_3$) δ 7.49 (d, J=8.6 Hz, 2H), 7.15 (s, 1H), 7.11 (d, J=8.3 Hz, 1H), 6.88 (d, J=8.6 Hz, 2H), 6.53 (d, J=8.2 Hz, 1H), 4.50 (s, 2H), 4.03-3.95 (m, 2H), 3.00-2.98 (m, 2H), 2.16 (s, 3H), 1.95 (m, 1H), 1.57 (m, 2H), 0.93 (t, J=7.4 Hz, 3H); MS (ES) m/z: 429 (M+H+).

Example C

Compound 3

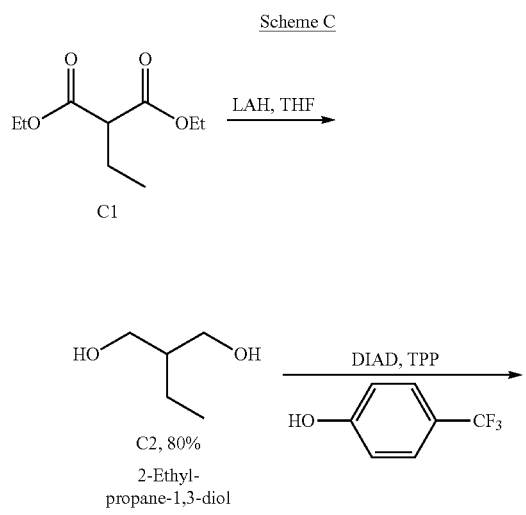

{2-Methyl-4-[2-(4-trifluoromethyl-phenoxymethyl)-butylsulfanyl]-phenoxy}-acetic acid Scheme C

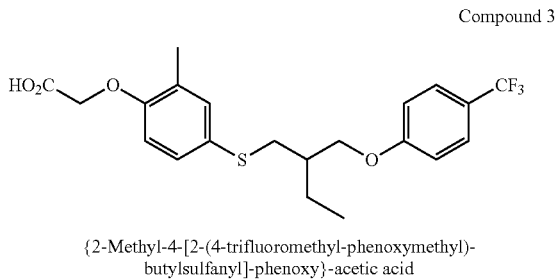

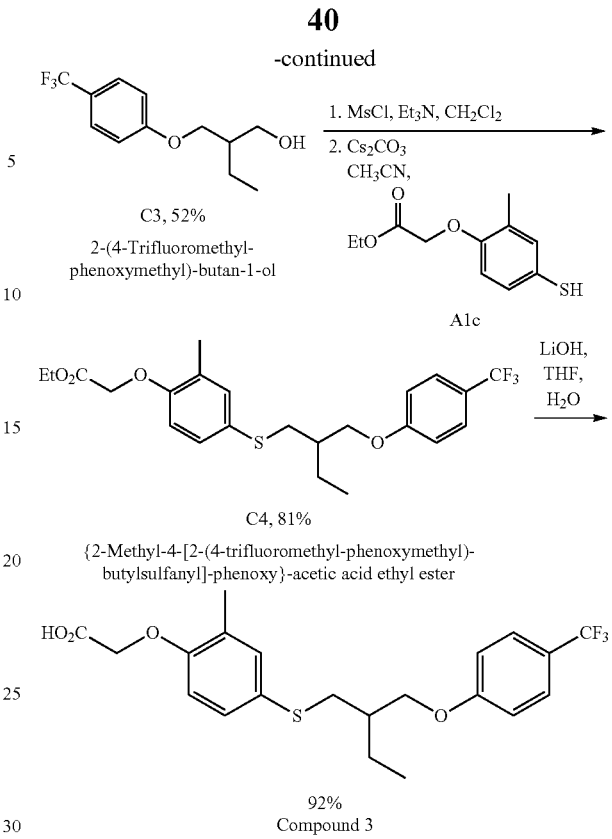

C3, 52%
2-(4-Trifluoromethyl-phenoxymethyl)-butan-1-ol

C4, 81%
{2-Methyl-4-[2-(4-trifluoromethyl-phenoxymethyl)-butylsulfanyl]-phenoxy}-acetic acid ethyl ester 92%
Compound 3

To a suspension of lithium aluminum hydride (101 mg, 2.66 mmol) in THF (3 mL) at 0° C. was added diethyl ethylmalonate C1 (250 mg, 1.33 mmol) dropwise. The reaction mixture was stirred at room temperature for 2 h, quenched with water (0.1 mL) and 5 N NaOH (0.2 mL), diluted with water (0.6 mL), filtered through Celite, and washed the solid with MeOH/CH$_2$Cl$_2$. The filtrate was dried, concentrated, and purified by column chromatography to give 110 mg (80%) of C2; 1H NMR (300 MHz, CDCl$_3$) δ 3.79 (dd, J=10.7, 3.9 Hz, 2H), 3.64 (dd, J=10.7, 7.5 Hz, 2H), 3.27 (s, 2H), 1.67 (m, 1H), 1.29 (m, 2H), 0.94 (t, J=7.5 Hz, 3H); MS (ES) m/z: 127 (M+Na+).

To a mixture of C2 (108 mg, 1.04 mmol), trifluoromethylphenol (130 mg, 0.802 mmol), and triphenylphosphine (210 mg, 0.802 mmol) in THF (3 mL) at 0° C. was added diisopropyl azodicarboxylate (162 mg, 0.802 mmol). The mixture was stirred at room temperature overnight, diluted with water, and extracted with Et$_2$O (x3). The extracts were dried, concentrated, and column chromatographed to provide 134 mg (52%) of C3; 1H NMR (400 MHz, CDCl$_3$) δ 7.54 (d, J=8.8 Hz, 2H), 6.97 (d, J=8.8 Hz, 2H), 4.05 (m, 2H), 3.80 (dd, J=10.8, 4.4 Hz, 1H), 3.74 (dd, J=10.8, 6.5 Hz, 1H), 1.94 (m, 1H), 1.50 (m, 2H), 1.00 (t, J=7.5 Hz, 3H); MS (ES) m/z: 249 (M+Na+).

C4 (81%) was prepared following general procedure 1 in Example A; 1H NMR (300 MHz, CDCl$_3$) δ 7.50 (d, J=8.6 Hz, 2H), 7.19 (d, J=1.8 Hz, 1H), 7.15 (dd, J=8.4, 2.2 Hz, 1H), 6.89 (d, J=8.6 Hz, 2H), 6.56 (d, J=8.4 Hz, 1H), 4.56 (s, 2H), 4.25 (q, J=7.1 Hz, 2H), 4.01 (m, 2H), 3.00 (d, J=6.4 Hz, 2H), 2.21 (s, 3H), 1.96 (m, 1H), 1.59 (m, 2H), 1.28 (t, J=7.1 Hz, 3H), 0.94 (t, J=7.5 Hz, 3H); MS (ES) m/z: 479 (M+Na+). Anal. Calcd for C$_{23}$H$_{27}$F$_3$O$_4$S: C, 60.51; H, 5.96. Found: C, 60.69; H, 5.56.

Compound 3 (92%) was prepared following general procedure 2 in Example A; 1H NMR (300 MHz, MeOH-d4) δ

7.53 (d, J=8.6 Hz, 2H), 7.18 (s, 1H), 7.15 (m, 1H), 6.96 (d, J=8.6 Hz, 2H), 6.66 (d, J=8.1 Hz, 1H), 4.55 (s, 2H), 4.04 (m, 2H), 3.00 (d, J=6.3 Hz, 2H), 2.16 (s, 3H), 1.92 (m, 1H), 1.58 (m, 2H), 0.94 (t, J=7.5 Hz, 3H); MS (ES) m/z: 451 (M+Na+).

Example D

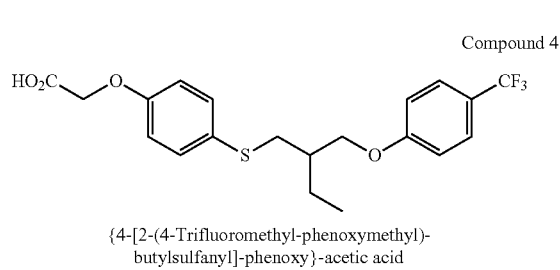

Compound 4

{4-[2-(4-Trifluoromethyl-phenoxymethyl)-butylsulfanyl]-phenoxy}-acetic acid

Scheme D

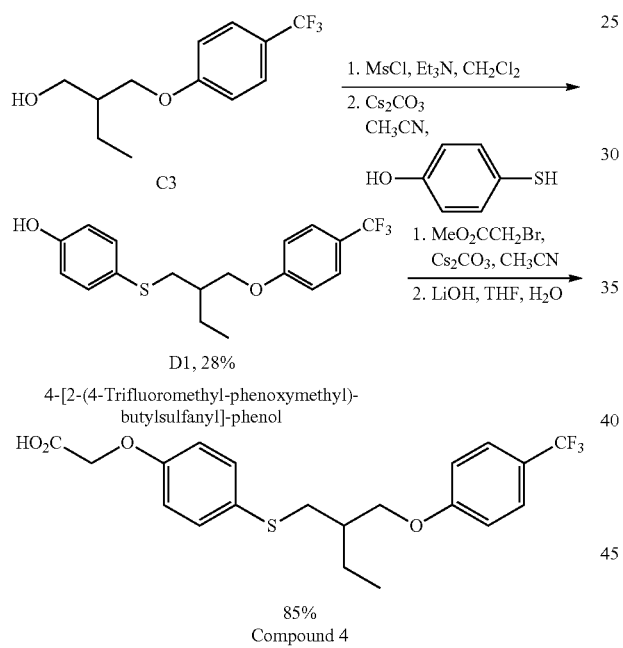

Replacing (4-mercapto-2-methyl-phenoxy)acetic acid ethyl ester A1c with 4-mercapto-phenol and following general procedure 1 in Example A gave D1 (28%); 1H NMR (300 MHz, CDCl₃) δ 7.51 (d, J=8.6 Hz, 2H), 7.28 (d, J=8.7 Hz, 2H), 6.91 (d, J=8.6 Hz, 2H), 6.72 (d, J=8.7 Hz, 2H), 4.84 (s, 1H), 4.02 (dd, J=5.2, 3.8 Hz, 2H), 2.99 (d, J=6.0 Hz, 2H), 1.95 (m, 1H), 1.59 (m, 2H), 0.94 (t, J=7.5 Hz, 3H); MS (ES) m/z: 357 (M+H+).

A mixture of D1 (86 mg, 0.24 mmol), bromoacetic acid methyl ester (55 mg, 0.36 mmol), and Cs₂CO₃ (157 mg, 0.482 mmol) in CH₃CN (2 mL) was stirred for 2 h and partitioned between Et₂O and water. The organic layer was dried, concentrated, and column chromatographed (EtOAc/hexane: ⅙) to give 99 mg (96%) of the methyl ester. Following general procedure 2, the above methyl ester was converted to acid Compound 4 (89%); 1H NMR (300 MHz, CDCl₃) δ 8.91 (brs, 1H), 7.49 (d, J=8.7 Hz, 2H), 7.26 (d, J=8.3 Hz, 2H), 6.88 (d, J=8.6 Hz, 2H), 6.74 (d, J=8.5 Hz, 2H), 4.46 (s, 2H), 3.98 (m, 2H), 3.01-2.92 (m, 2H), 1.93 (m, 1H), 1.56 (m, 2H), 0.92 (t, J=7.4 Hz, 3H); MS (ES) m/z: 437 (M+Na+).

Example E

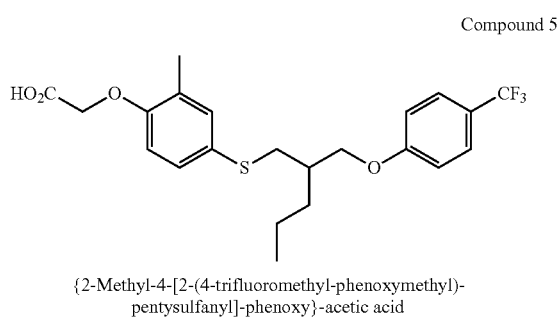

Compound 5

{2-Methyl-4-[2-(4-trifluoromethyl-phenoxymethyl)-pentysulfanyl]-phenoxy}-acetic acid Scheme E

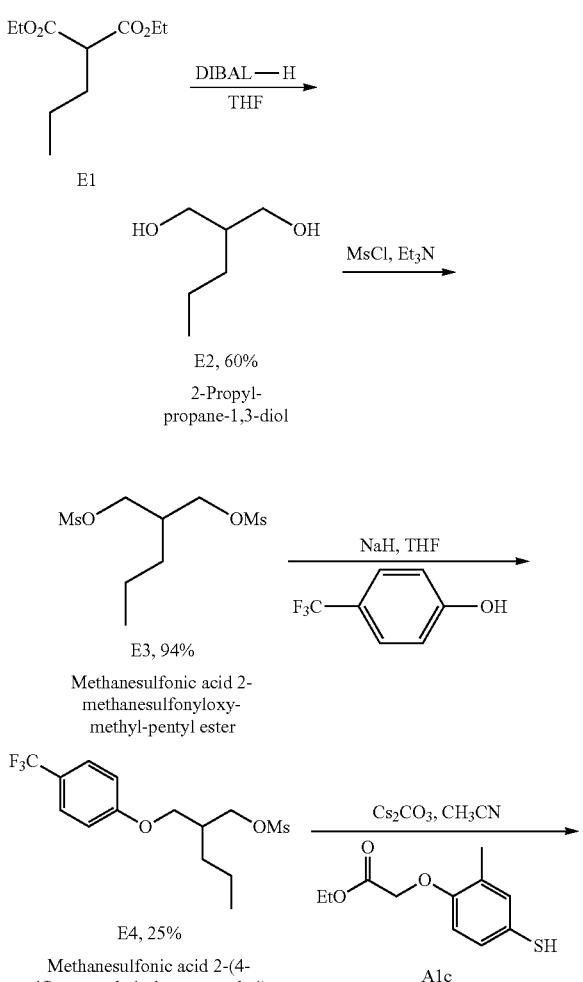

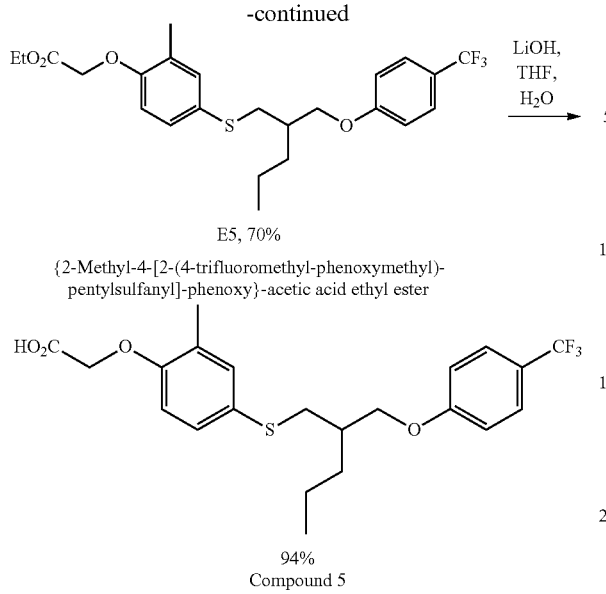

E5, 70%
{2-Methyl-4-[2-(4-trifluoromethyl-phenoxymethyl)-pentylsulfanyl]-phenoxy}-acetic acid ethyl ester 94%
Compound 5 ethyl ester A1c (163 mg, 0.721 mmol) in $CH_3CN$ (3 mL). After stirring for 5 h at room temperature, water was added and the mixture was extracted with $Et_2O$. The combined organic layers were dried, concentrated, and column chromatographed (EtOAc/hexane: 1/10) to provide 158 mg (70%) of E5; 1H NMR (300 MHz, $CDCl_3$) δ 7.51 (d, J=8.6 Hz, 2H), 7.19 (d, J=1.5 Hz, 1H), 7.14 (dd, J=8.4, 2.3 Hz, 1H), 6.89 (d, J=8.6 Hz, 2H), 6.55 (d, J=8.4 Hz, 1H), 4.56 (s, 2H), 4.25 (q, J=7.1 Hz, 2H), 4.03 (dd, J=9.3, 4.9 Hz, 1H), 3.97 (dd, J=9.2, 5.6 Hz, 1H), 3.00 (d, J=6.5 Hz, 2H), 2.21 (s, 3H), 2.05 (m, 1H), 1.57-1.48 (m, 2H), 1.40-1.32 (m, 2H), 1.29 (t, J=7.1 Hz, 3H), 0.91 (t, J=7.2 Hz, 3H); MS (ES) m/z: 493 (M+Na+). Anal. Calcd for $C_{24}H_{29}F_3O_4S$: C, 61.26; H, 6.21. Found: C, 61.49; H, 6.35.

Following general procedure 2 in Example A gave Compound 5 (94%); 1H NMR (400 MHz, $CDCl_3$) δ 7.50 (d, J=8.7 Hz, 2H), 7.18 (d, J=1.7 Hz, 1H), 7.15 (dd, J=8.5, 2.0 Hz, 1H), 6.88 (d, J=8.7 Hz, 2H), 6.57 (d, J=8.4 Hz, 1H), 4.60 (s, 2H), 4.02 (dd, J=9.2, 4.7 Hz, 1H), 3.97 (dd, J=9.2, 5.7 Hz, 1H), 3.01 (m, 2H), 2.19 (s, 3H), 2.05 (m, 1H), 1.54-1.49 (m, 2H), 1.37 (m, 2H), 0.91 (t, J=7.2 Hz, 3H); MS (ES) m/z: 465 (M+Na+). Anal. Calcd for $C_{22}H_{25}F_3O_4S$: C, 59.72; H, 5.69. Found: C, 59.63; H, 5.75.

Example F

Compound 6

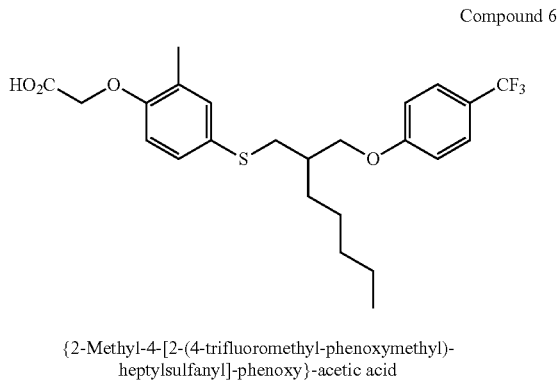

{2-Methyl-4-[2-(4-trifluoromethyl-phenoxymethyl)-heptylsulfanyl]-phenoxy}-acetic acid To a solution of 1.0 M diisobutylaluminum hydride (50 mL, 50 mmol) in $CH_2Cl_2$ at −78° C. was added diethyl propylmalonate E1 (2.02 g, 10.0 mmol). The reaction mixture was allowed to gradually warm to 0° C., stirred at 0° C. for 30 min, and quenched with MeOH. The precipitated solid was filtered through Celite and washed with MeOH/$CH_2Cl_2$. The filtrate was concentrated and purified by column chromatography (EtOAc) to give 709 mg (60%) of E2; 1H NMR (300 MHz, $CDCl_3$) δ 3.80 (dd, J=10.7, 3.8 Hz, 2H), 3.63 (dd, J=10.7, 7.7 Hz, 2H), 2.82 (s, 2H), 1.84-1.71 (m, 1H), 1.42-1.28 (m, 2H), 1.24-1.17 (m, 2H), 0.91 (t, J=7.2 Hz, 3H); MS (ES) m/z: 141 (M+Na+).

To a solution of E2 (300 mg, 2.54 mmol) in $CH_2Cl_2$ (5 mL) at 0° C. were added $Et_3N$ (1.06 mL, 7.62 mmol) and methanesulfonyl chloride (729 mg, 6.36 mmol). The mixture was stirred at 0° C. for 2 h and diluted with saturated $NaHCO_3$. The organic layer was separated and the aqueous layer was extracted with $CH_2Cl_2$ (×3). The combined organic phases were dried, concentrated, and column chromatographed (EtOAc/hexane: 1/1) to provide 655 mg (94%) of E3; 1H NMR (300 MHz, $CDCl_3$) δ 4.29 (dd, J=10.0, 4.3 Hz, 2H), 4.20 (dd, J=10.0, 6.4 Hz, 2H), 3.05 (s, 6H), 2.22-2.15 (m, 1H), 1.42 (m, 4H), 0.97-0.93 (m, 3H); MS (ES) m/z: 297 (M+Na+).

To a suspension of NaH (80 mg, 2.0 mmol; 60% in mineral oil) in THF (2 mL) was added a solution of 4-trifluoromethylphenol (324 mg, 2.0 mmol) in THF (2 mL). After stirring at room temperature for 30 min, a solution of E3 (659 mg, 2.40 mmol) in THF (3 mL) was added and the resulting mixture was refluxed for 6 h. Water was added and the mixture was extracted with $Et_2O$. The extracts were dried, concentrated, and column chromatographed (EtOAc/hexane: 1/4) to afford 170 mg (25%) of E4; 1H NMR (300 MHz, $CDCl_3$) δ 7.54 (d, J=8.6 Hz, 2H), 6.96 (d, J=8.6 Hz, 2H), 4.37 (dd, J=9.9, 4.9 Hz, 1H), 4.32 (dd, J=9.9, 6.0 Hz, 1H), 4.04 (dd, J=9.4, 4.6 Hz, 1H), 3.98 (dd, J=9.3, 6.4 Hz, 1H), 2.97 (s, 3H), 2.25 (m, 1H), 1.53-1.39 (m, 4H), 0.96 (t, J=7.0 Hz, 3H); MS (ES) m/z: 363 (M+Na+).

General Procedure 3 for the Formation of Thioether:

To a solution of E4 (165 mg, 0.485 mmol) in $CH_3CN$ (5 mL) was added $Cs_2CO_3$ (391 mg, 1.20 mmol) followed by a solution of (4-mercapto-2-methyl-phenoxy)acetic acid Scheme F

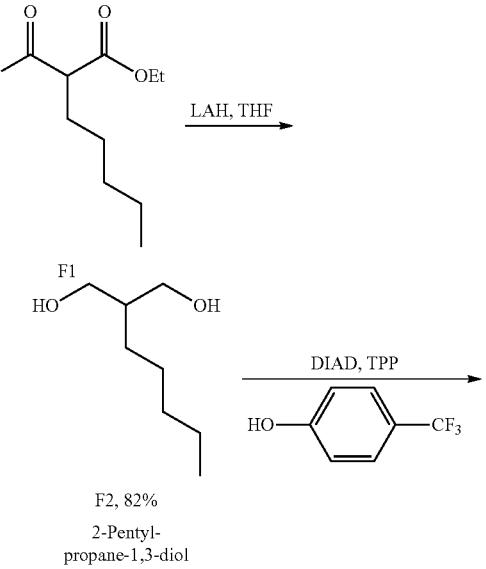

F2, 82%
2-Pentyl-propane-1,3-diol

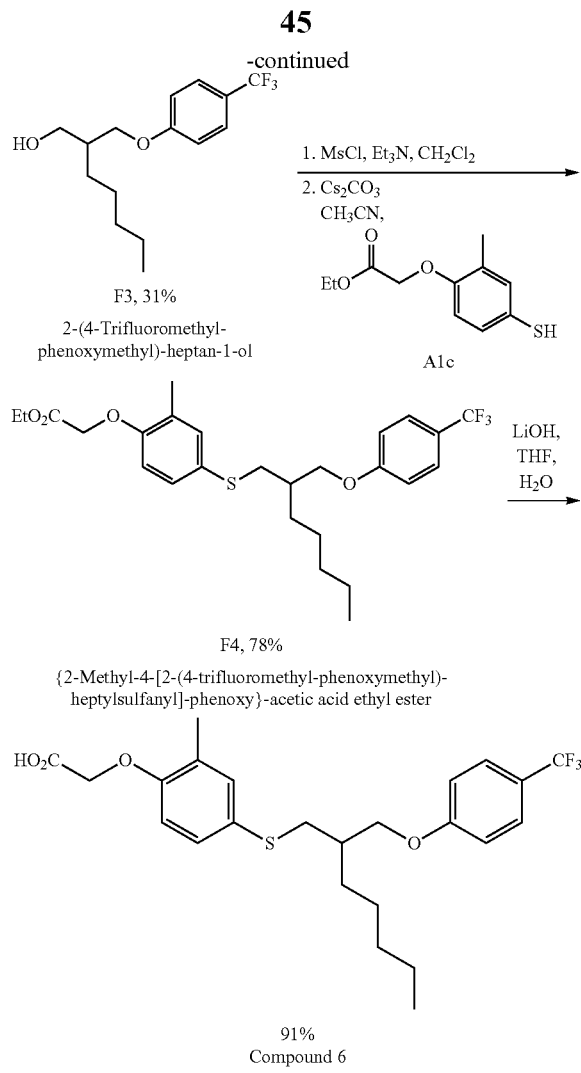

F3, 31%
2-(4-Trifluoromethyl-phenoxymethyl)-heptan-1-ol

F4, 78%
{2-Methyl-4-[2-(4-trifluoromethyl-phenoxymethyl)-heptylsulfanyl]-phenoxy}-acetic acid ethyl ester 91%
Compound 6

To a suspension of lithium aluminum hydride (114 mg, 3.00 mmol) in THF (3 mL) at 0° C. was added 2-pentyl-malonic acid diethyl ester F1 (346 mg, 1.50 mmol) dropwise. The reaction mixture was stirred at room temperature for 2 h, quenched with water (0.1 mL) and 5 N NaOH (0.2 mL) at 0° C., and diluted with water (0.6 mL). The precipitated solid was filtered through Celite and washed with MeOH/CH$_2$Cl$_2$. The filtrate was dried, concentrated, and purified by column chromatography (EtOAc/hexane: 1/1) to give 181 mg (82%) of F2; 1H NMR (300 MHz, CDCl$_3$) δ 3.79 (dd, J=10.7, 3.8 Hz, 2H), 3.62 (dd, J=10.7, 7.7 Hz, 2H), 3.16 (s, 2H), 1.75 (m, 1H), 1.34-1.18 (m, 8H), 0.88 (t, J=6.8 Hz, 3H); MS (ES) m/z: 169 (M+Na+).

To a mixture of F2 (176 mg, 1.21 mmol), trifluoromethylphenol (292 mg, 1.80 mmol), and triphenylphosphine (472 mg, 1.80 mmol) in THF (3 mL) at 0° C. was added diisopropyl azodicarboxylate (195 mg, 1.80 mmol). The mixture was stirred at 0° C. for 30 min and then room temperature for 6 h, diluted with water, and extracted with Et$_2$O. The extracts were dried, concentrated, and purified by column chromatography to provide 108 mg (31%) of F3; 1H NMR (300 MHz, CDCl$_3$) δ 7.53 (d, J=8.6 Hz, 2H), 6.96 (d, J=8.6 Hz, 2H), 4.03 (m, 2H), 3.75 (m, 2H), 2.04-1.95 (m, 1H), 1.44-1.36 (m, 4H), 1.31-1.25 (m, 4H), 0.89 (t, J=6.8 Hz, 3H); MS (ES) m/z: 313 (M+Na+).

Following general procedure 1 in Example A gave F4 (78%); 1H NMR (300 MHz, CDCl$_3$) δ 7.50 (d, J=8.6 Hz, 2H), 7.19 (d, J=1.7 Hz, 1H), 7.14 (dd, J=8.4, 2.2 Hz, 1H), 6.89 (d, J=8.6 Hz, 2H), 6.55 (d, J=8.4 Hz, 1H), 4.56 (s, 2H), 4.25 (q, J=7.1 Hz, 2H), 4.00 (m, 2H), 3.01 (d, J=6.8 Hz, 2H), 2.21 (s, 3H), 2.03 (m, 1H), 1.56-1.49 (m, 2H), 1.37-1.22 (m, 6H), 1.28 (t, J=7.1 Hz, 3H), 0.87 (t, J=6.8 Hz, 3H); MS (ES) m/z: 521 (M+Na+).

Following general procedure 2 in Example A gave Compound 6 (91%); 1H NMR (300 MHz, CDCl$_3$) δ 9.23 (brs, 1H), 7.50 (d, J=8.7 Hz, 2H), 7.19 (d, J=1.8 Hz, 1H), 7.15 (dd, J=8.4, 2.2 Hz, 1H), 6.89 (d, J=8.6 Hz, 2H), 6.57 (d, J=8.4 Hz, 1H), 4.61 (s, 2H), 4.00 (m, 2H), 3.03-3.00 (m, 2H), 2.20 (s, 3H), 2.04 (m, 1H), 1.56-1.49 (m, 2H), 1.37-1.23 (m, 6H), 0.87 (t, J=6.8 Hz, 3H); MS (ES) m/z: 493 (M+Na+).

Example G

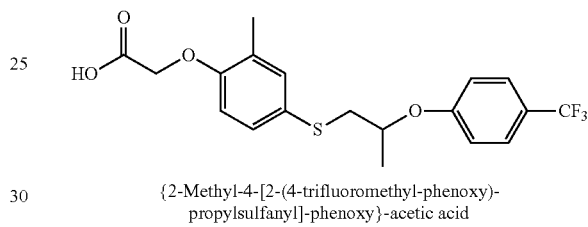

Compound 7
{2-Methyl-4-[2-(4-trifluoromethyl-phenoxy)-propylsulfanyl]-phenoxy}-acetic acid Scheme G

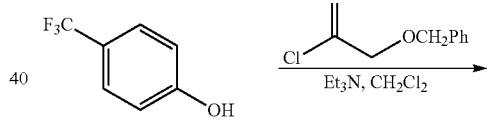

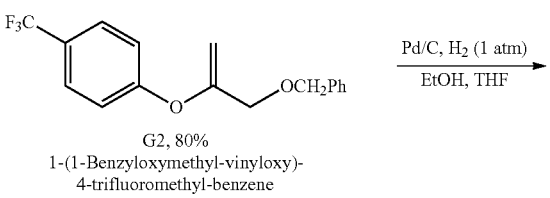

G1, 94%
Benzyloxy-acetic acid 4-trifluoromethyl-phenyl ester

G2, 80%
1-(1-Benzyloxymethyl-vinyloxy)-4-trifluoromethyl-benzene

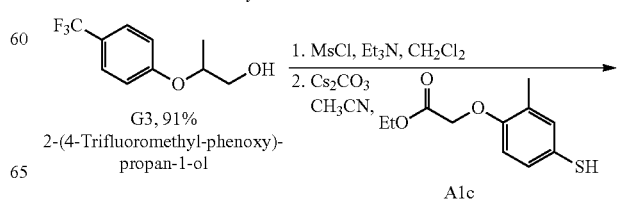

G3, 91%
2-(4-Trifluoromethyl-phenoxy)-propan-1-ol

A1c

-continued

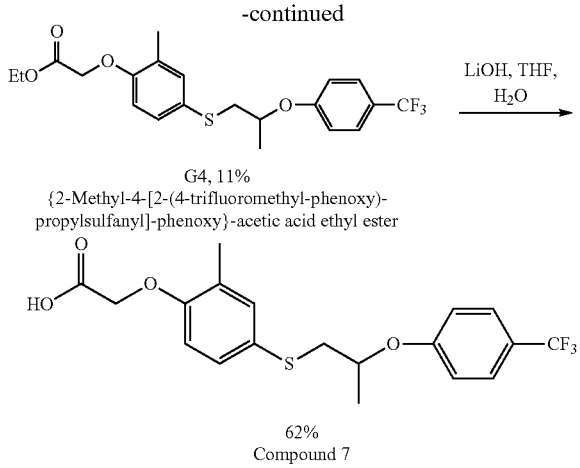

G4, 11%
{2-Methyl-4-[2-(4-trifluoromethyl-phenoxy)-propylsulfanyl]-phenoxy}-acetic acid ethyl ester LiOH, THF,
H₂O 62%
Compound 7

To a mixture of 4-trifluoromethylphenol (1.00 g, 6.17 mmol) and Et₃N (871 mg, 8.63 mmol) in CH₂Cl₂ (20 mL) at 4° C. was added phenoxylacetyl chloride (1.37 g, 7.42 mmol). After stirring for 2 h at room temperature, the white solid was filtered and washed with Et₂O. The filtrate was washed with water, dried, concentrated, and purified by column chromatography to give 1.79 g (94%) of G1 as a white solid; 1H NMR (300 MHz, CDCl₃) δ 7.66 (d, J=8.7 Hz, 2H), 7.43-7.33 (m, 5H), 7.25 (d, J=8.4 Hz, 2H), 4.73 (s, 2H), 4.37 (s, 2H).

To a solution of G1 (1.20 g, 3.87 mmol) in THF (20 mL) at −78° C. was introduced a solution of 0.5 M Tebbe reagent (9.3 mL, 4.7 mmol) in toluene. The mixture was stirred at −78° C. to 2° C. for 2 h and quenched with water dropwise. The formed solid was filtered and washed with Et₂O. The filtrate was concentrated and purified by column chromatography to provide 890 mg (75%) of G2 as a clear oil; 1H NMR (300 MHz, CDCl₃) δ 7.60 (d, J=8.5 Hz, 2H), 7.36-7.29 (m, 5H), 7.16 (d, J=8.6 Hz, 2H), 4.70 (d, J=2.1 Hz, 1H), 4.63 (s, 2H), 4.39 (d, J=2.1 Hz, 1H), 4.12 (s, 2H).

A mixture of G2 (870 mg, 2.82 mmol) and 10% Pd/C (100 mg) in EtOH (10 mL) and THF (5 mL) was degassed and filled with H₂ three times. After hydrogenating under 1 atm overnight, the mixture was filtered through Celite. The filtrate was concentrated and column chromatographed to give 563 mg (91%) of G3 as a clear oil; 1H NMR (300 MHz, CDCl₃) δ 7.54 (d, J=8.6 Hz, 2H), 7.99 (d, J=8.6 Hz, 2H), 4.57 (m, 1H), 3.76 (m, 2H), 1.93 (t, J=6.3 Hz, 1H), 1.30 (d, J=6.2 Hz, 3H); MS (ES) m/z: 243 (M+Na+).

Following general procedure 1 in Example A gave G4 (11%, clear oil); 1H NMR (400 MHz, CDCl₃) δ 7.47 (d, J=8.9 Hz, 2H), 7.24 (s, 1H), 7.21 (dd, J=8.5, 2.1 Hz, 1H), 6.76 (d, J=8.9 Hz, 2H), 6.63 (d, J=8.5 Hz, 1H), 4.64 (s, 2H), 4.46 (dd, J=12.0, 6.1 Hz, 1H), 4.27 (q, J=7.1 Hz, 2H), 3.16 (dd, J=13.8, 5.3 Hz, 1H), 2.90 (dd, J=13.8, 6.9 Hz, 1H), 2.26 (s, 3H), 1.43 (d, J=5.9 Hz, 3H), 1.30 (t, J=7.1 Hz, 3H); MS (ES) m/z: 451 (M+Na+).

Following general procedure 2 in Example A gave Compound 7 (62%, solid); 1H NMR (300 MHz, MeOH-d4) δ 7.50 (d, J=8.6 Hz, 2H), 7.21 (m, 2H), 6.83 (d, J=8.7 Hz, 2H), 6.75 (d, J=7.4 Hz, 1H), 4.62 (s, 2H), 4.54 (dd, J=11.8, 6.0 Hz, 1H), 3.12 (dd, J=13.9, 5.6 Hz, 1H), 2.96 (dd, J=14.0, 6.2 Hz, 1H), 2.21 (s, 3H), 1.41 (d, J=6.2 Hz, 3H); MS (ES) m/z: 423 (M+Na+); FAB-HRMS (M+). Calcd 400.0956. found 400.0944.

Example H

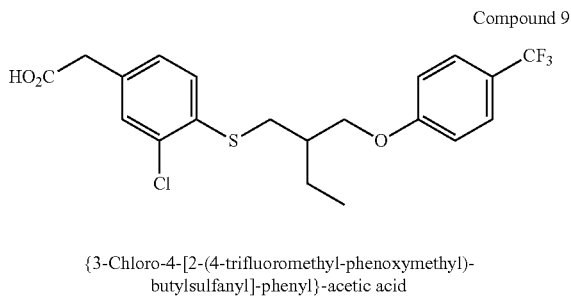

Compound 9

{3-Chloro-4-[2-(4-trifluoromethyl-phenoxymethyl)-butylsulfanyl]-phenyl}-acetic acid Scheme H

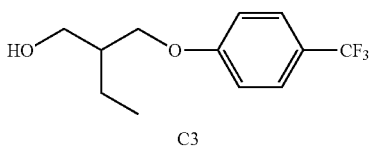

C3

MsCl, Et₃N, CH₂Cl₂

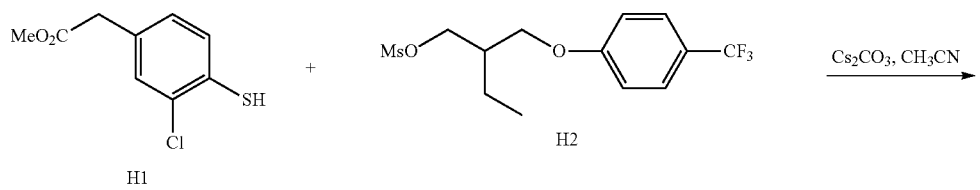

Cs₂CO₃, CH₃CN

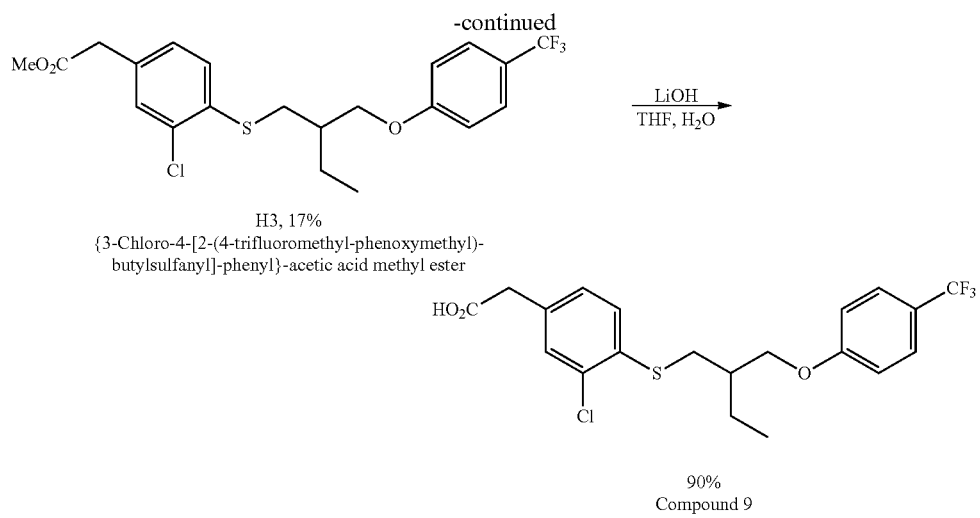

H3, 17%
{3-Chloro-4-[2-(4-trifluoromethyl-phenoxymethyl)-butylsulfanyl]-phenyl}-acetic acid methyl ester

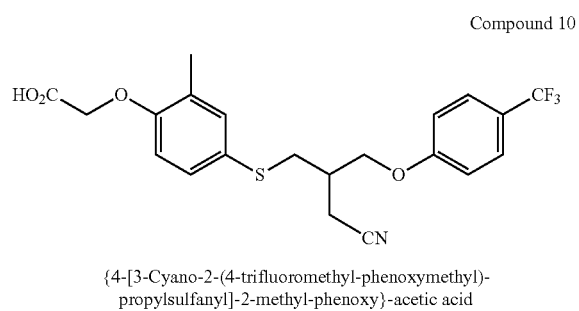

90%
Compound 9

A mixture of (3-chloro-4-mercaptophenyl) acetic acid methyl ester H1 (758 mg, 3.48 mmol; Sahoo, S. P., Preparation of arylthiazolidinediones as agonists of peroxisome proliferator activated receptor, WO99/32465), methanesulfonic acid 2-(4-trifluoromethyl-phenoxymethyl)pentyl ester H2 (880 mg, 2.70 mmol;), and $Cs_2CO_3$ (2.64 g, 8.10 mmol) in $CH_3CN$ (8 mL) was stirred for 2 h, diluted with water, and extracted with $Et_2O$. The combined organic layers were dried, concentrated, and column chromatographed (EtOAc/hexane: 1/7) to give 205 mg (17%) of H3; 1H NMR (400 MHz, $CDCl_3$) δ 7.51 (d, J=8.7 Hz, 2H), 7.29 (s, 1H), 7.27 (s, 1H), 7.08 (dd, J=8.1, 1.7 Hz, 1H), 6.93 (d, J=8.6 Hz, 2H), 4.09 (dd, J=9.3, 4.7 Hz, 1H), 4.00 (dd, J=9.3, 5.8 Hz, 1H), 3.69 (s, 3H), 3.53 (s, 2H), 3.14 (dd, J=13.0, 7.0 Hz, 1H), 3.06 (dd, J=13.0, 5.7 Hz, 1H), 2.06 (m, 1H), 1.69-1.61 (m, 2H), 0.99 (t, J=7.4 Hz, 3H).

Following general procedure 2 in Example A gave Compound 9 (90%); 1H NMR (300 MHz, $CDCl_3$) δ 7.51 (d, J=8.6 Hz, 2H), 7.26 (m, 2H), 7.06 (d, J=8.0 Hz, 1H), 6.92 (d, J=8.6 Hz, 2H), 4.08 (dd, J=9.3, 4.6 Hz, 1H), 3.99 (dd, J=9.3, 5.8 Hz, 1H), 3.54 (s, 2H), 3.14 (dd, J=13.0, 7.0 Hz, 1H), 3.05 (dd, J=13.0, 5.7 Hz, 1H), 2.06 (m, 1H), 1.64 (m, 2H), 0.99 (t, J=7.4 Hz, 3H); MS (ES) m/z: 455 (M+Na+).

Example I

Compound 10

{4-[3-Cyano-2-(4-trifluoromethyl-phenoxymethyl)-propylsulfanyl]-2-methyl-phenoxy}-acetic acid Scheme I

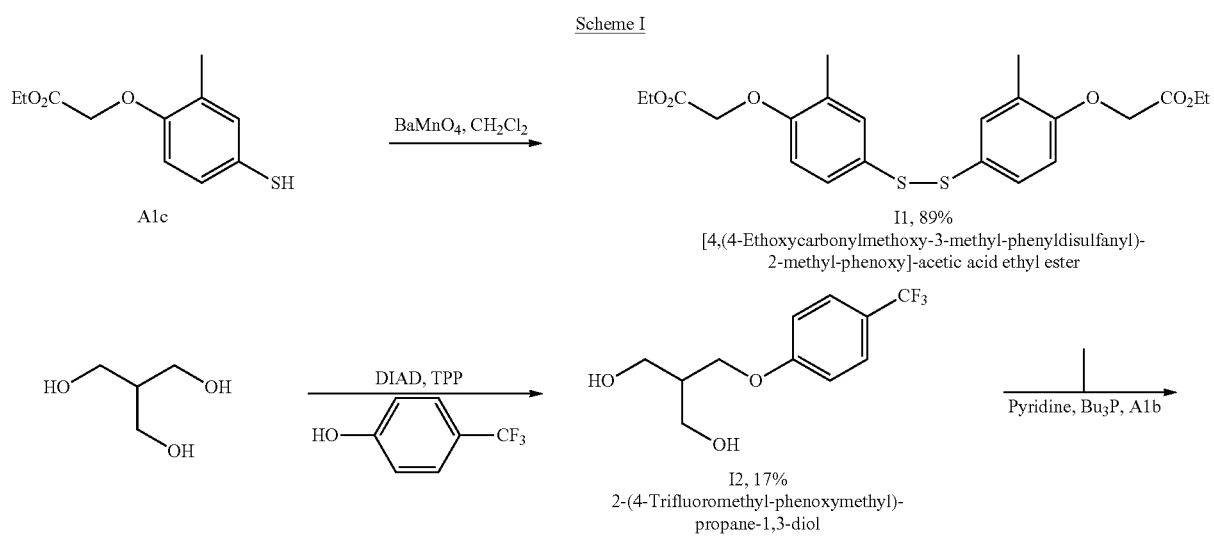

I1, 89%
[4,(4-Ethoxycarbonylmethoxy-3-methyl-phenyldisulfanyl)-2-methyl-phenoxy]-acetic acid ethyl ester I2, 17%
2-(4-Trifluoromethyl-phenoxymethyl)-propane-1,3-diol

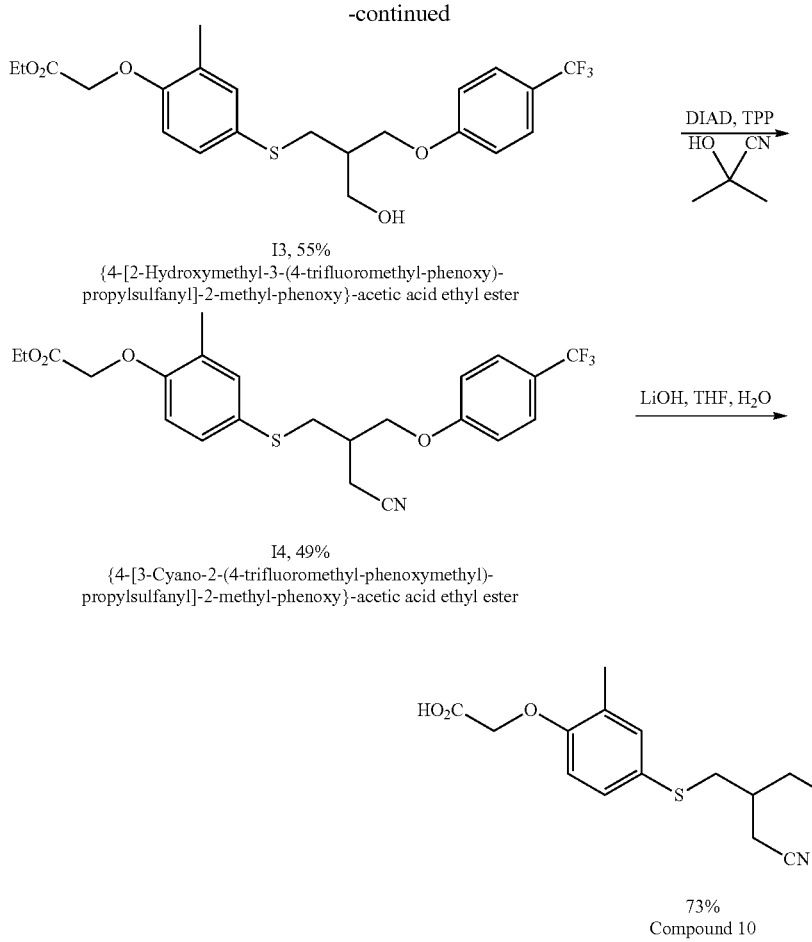

I3, 55%
{4-[2-Hydroxymethyl-3-(4-trifluoromethyl-phenoxy)-propylsulfanyl]-2-methyl-phenoxy}-acetic acid ethyl ester I4, 49%
{4-[3-Cyano-2-(4-trifluoromethyl-phenoxymethyl)-propylsulfanyl]-2-methyl-phenoxy}-acetic acid ethyl ester 73%
Compound 10

A mixture of (4-mercapto-2-methylphenoxy)acetic acid ethyl ester A1c (453 mg, 2.00 mmol) and barium manganate (513 mg, 2.00 mmol) in $CH_2Cl_2$ (5 mL) was stirred at room temperature for 20 min, filtered through silica gel, and washed with EtOAc/hexane (⅓). The filtrate was concentrated to give 802 mg (89%) of I1; 1H NMR (400 MHz, $CDCl_3$) δ 7.27 (s, 1H), 7.23 (dd, J=8.4, 2.3 Hz, 1H), 6.61 (d, J=8.5 Hz, 1H), 4.62 (s, 2H), 4.26 (q, J=7.1 Hz, 2H), 2.25 (s, 3H), 1.29 (t, J=7.1 Hz, 3H); MS (ES) m/z: 473 (M+Na+).

To a mixture of 2-hydroxymethylpropane-1,3-diol (500 mg, 4.71 mmol) in DMF (1.5 mL) and THF (3 mL) were added trifluoromethylphenol (822 mg, 5.07 mmol) and triphenylphosphine (1.02 g, 3.90 mmol). After the mixture was cooled to 0° C., diisopropyl azodicarboxylate (789 mg, 3.91 mmol) was introduced. The mixture was allowed to warm up to room temperature, stirred overnight, concentrated, and column chromatographed to provide 200 mg (17%) of I2; 1H NMR (300 MHz, $CDCl_3$) δ 7.50 (d, J=8.7 Hz, 2H), 6.93 (d, J=8.6 Hz, 2H), 4.05 (d, J=6.1 Hz, 2H), 3.90-3.80 (m, 4H), 3.42 (brs, 2H), 2.20 (m, 1H); MS (ES) m/z: 273 (M+Na+).

To a mixture of 11 (97 mg, 0.22 mmol) and I2 (81 mg, 0.32 mmol) in pyridine (0.2 mL) was added tributylphosphine (44 mg, 0.22 mmol). The mixture was stirred overnight, diluted with 1 N HCl, and extracted with $Et_2O$. The extracts were dried, concentrated, and column chromatographed (EtOAc/hexane: ⅖) to provide 54 mg (55%) of I3; 1H NMR (400 MHz, $CDCl_3$) δ 7.52 (d, J=8.9 Hz, 2H), 7.22 (d, J=2.2 Hz, 1H), 7.18 (dd, J=8.4, 2.3 Hz, 1H), 6.92 (d, J=8.8 Hz, 2H), 6.59 (d, J=8.4 Hz, 1H), 4.59 (s, 2H), 4.26 (q, J=7.1 Hz, 2H), 4.16-4.09 (m, 2H), 3.86 (d, J=5.3 Hz, 2H), 3.04 (d, J=6.8 Hz, 2H), 2.26-2.20 (m, 1H), 2.23 (s, 3H), 1.29 (t, J=7.1 Hz, 3H); MS (ES) m/z: 481 (M+Na+).

To a mixture of 13 (114 mg, 0.249 mmol) and triphenylphosphine (98 mg, 0.37 mmol) in THF (2 mL) at 0° C. was added diisopropyl azodicarboxylate (75 mg, 0.37 mmol) and acetone cyanohydrin (32 mg, 0.38 mmol). The mixture was stirred at room temperature overnight, concentrated, and column chromatographed to provide 57 mg (49%) of I4; 1H NMR (400 MHz, $CDCl_3$) δ 7.54 (d, J=8.7 Hz, 2H), 7.23 (s, 1H), 7.20 (dd, J=8.4, 2.2 Hz, 1H), 6.91 (d, J=8.7 Hz, 2H), 6.60 (d, J=8.4 Hz, 1H), 4.60 (s, 2H), 4.26 (q, J=7.1 Hz, 2H), 4.13 (dd, J=9.5, 4.6 Hz, 1H), 4.08 (dd, J=9.5, 6.0 Hz, 1H), 3.08 (dd, J=14.0, 6.9 Hz, 1H), 3.00 (dd, J=13.9, 7.0 Hz, 1H), 2.73 (dd, J=6.3, 1.8 Hz, 2H), 2.37 (m, 1H), 2.25 (s, 3H), 1.30 (t, J=7.1 Hz, 3H); MS (ES) m/z: 490 (M+Na+). Anal. Calcd for $C_{23}H_{24}F_3NO_4S$: C, 59.09; H, 5.17; N, 3.00. Found: C, 59.11; H, 5.12; N, 2.93.

Following general procedure 2 in Example A gave Compound 10 (73%); 1H NMR (300 MHz, $CD_3OD$) δ 7.55 (d, J=8.6 Hz, 2H), 7.23 (m, 2H), 7.00 (d, J=8.6 Hz, 2H), 6.71 (d, J=8.2 Hz, 1H), 4.55 (s, 2H), 4.12 (d, J=5.2 Hz, 2H), 3.11 (dd, J=14.0, 7.0 Hz, 1H), 3.01 (dd, J=14.0, 6.7 Hz, 1H), 2.78 (d, J=6.3 Hz, 2H), 2.33 (m, 1H), 2.18 (s, 3H); MS (ES) m/z: 462 (M+Na+).

Example J
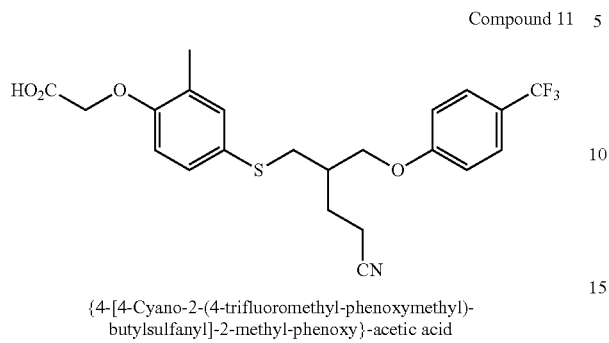
{4-[4-Cyano-2-(4-trifluoromethyl-phenoxymethyl)-butylsulfanyl]-2-methyl-phenoxy}-acetic acid
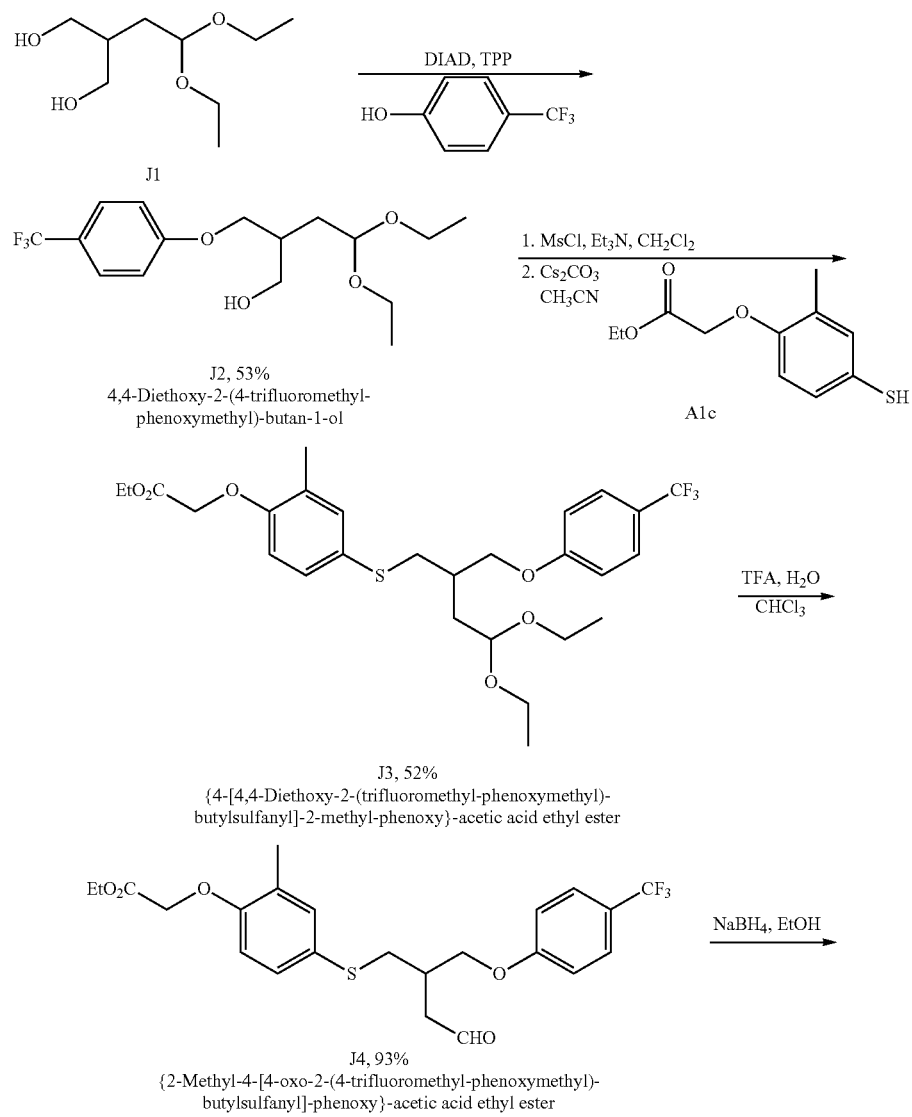

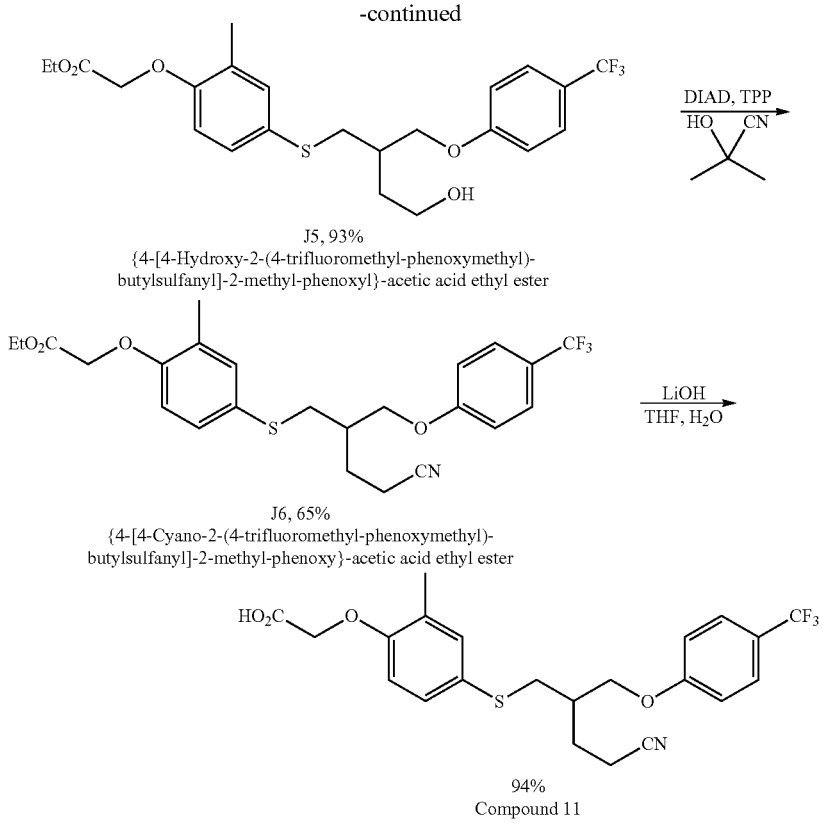

To a mixture of 2-(2,2-diethoxyethyl)-1,3-propanediol J1 (500 mg, 2.60 mmol), trifluoromethylphenol (357 mg, 2.20 mmol), and triphenylphosphine (525 mg, 2.00 mmol) in THF (5 mL) at 0° C. was added diisopropyl azodicarboxylate (384 mg, 1.90 mmol). The mixture was allowed to warm up to room temperature, stirred overnight, diluted with water, and extracted with Et$_2$O. The combined organic layers were dried, concentrated, and column chromatographed (EtOAc/hexane: 1/4) to provide 436 mg (53%) of J2; 1H NMR (300 MHz, CDCl$_3$) δ 7.53 (d, J=8.7 Hz, 2H), 6.94 (dd, J=8.8, 2.2 Hz, 2H), 5.18 (m, 1H), 4.15-4.03 (m, 2H), 3.92-3.88 (m, 1H), 3.85-3.78 (m, 1H), 3.77-3.67 (m, 2H), 3.49-3.43 (m, 1H), 2.95-2.86 (m, 1H), 2.28-2.18 (m, 1H), 2.15-2.07 (m, 1H), 1.88-1.79 (m, 1H), 1.23 (t, J=7.0 Hz, 6H); MS (ES) m/z: 359 (M+Na+).

Following general procedure 1 in Example A provided J3 (56%); 1H NMR (400 MHz, CDCl$_3$) δ 7.50 (d, J=8.8 Hz, 2H), 7.19 (d, J=2.1 Hz, 1H), 7.15 (dd, J=8.4, 2.3 Hz, 1H), 6.88 (d, J=8.7 Hz, 2H), 6.54 (d, J=8.4 Hz, 1H), 4.59 (t, J=5.7 Hz, 1H), 4.56 (s, 2H), 4.25 (q, J=7.1 Hz, 2H), 4.11 (dd, J=9.3, 4.6 Hz, 1H), 4.00 (dd, J=9.3, 5.6 Hz, 1H), 3.65-3.58 (m, 2H), 3.48-3.43 (m, 2H), 3.06-3.04 (m, 2H), 2.26-2.20 (m, 1H), 2.20 (s, 3H), 1.88 (m, 2H), 1.29 (t, J=7.1 Hz, 3H), 1.16 (t, J=7.0 Hz, 3H), 1.15 (t, J=7.0 Hz, 3H); MS (ES) m/z: 567 (M+Na+). Anal. Calcd for C$_{27}$H$_{35}$F$_3$O$_6$S: C, 59.54; H, 6.48. Found: C, 59.75; H, 6.45.

A mixture of J3 (130 mg, 0.239 mmol) in trifluoroacetic acid (1.5 mL), water (1.5 mL), and CHCl$_3$ (6 mL) was stirred at room temperature for 3 h, diluted with water, and extracted with CHCl$_3$. The organic phases were dried, concentrated, and column chromatographed (CH$_2$Cl$_2$) to afford 105 mg (93%) of J4; 1H NMR (300 MHz, CDCl$_3$) δ 9.78 (s, 1H), 7.51 (d, J=8.6 Hz, 2H), 7.21 (d, J=1.7 Hz, 1H), 7.16 (dd, J=8.4, 2.2 Hz, 1H), 6.88 (d, J=8.6 Hz, 2H), 6.58 (d, J=8.4 Hz, 1H), 4.58 (s, 2H), 4.25 (q, J=7.1 Hz, 2H), 4.04 (d, J=4.9 Hz, 2H), 3.07 (dd, J=13.7, 6.6 Hz, 1H), 2.97 (dd, J=13.7, 6.1 Hz, 1H), 2.77-2.64 (m, 3H), 2.23 (s, 3H), 1.29 (t, J=7.1 Hz, 3H); MS (ES) m/z: 493 (M+Na+).

To a solution of J4 (100 mg, 0.213 mmol) in EtOH (1.2 mL) at 0° C. was added NaBH$_4$ (48 mg, 1.3 mmol). After stirring for 15 min at the same temperature, the mixture was diluted with Et$_2$O, acidified with 1 N HCl, and extracted with Et$_2$O. The combined organic layers were dried, concentrated, and column chromatographed to afford 93 mg (93%) of J5; 1H NMR (300 MHz, CDCl$_3$) δ 7.51 (d, J=8.6 Hz, 2H), 7.20 (d, J=1.8 Hz, 1H), 7.15 (dd, J=8.4, 2.2 Hz, 1H), 6.89 (d, J=8.6 Hz, 2H), 6.56 (d, J=8.4 Hz, 1H), 4.57 (s, 2H), 4.25 (q, J=7.1 Hz, 2H), 4.05 (m, 2H), 3.73 (t, J=6.4 Hz, 2H), 3.03 (m, 2H), 2.29-2.21 (m, 1H), 2.21 (s, 3H), 1.82 (q, J=6.5 Hz, 2H), 1.29 (t, J=7.1 Hz, 3H); MS (ES) m/z: 495 (M+Na+). Anal. Calcd for C$_{23}$H$_{27}$F$_3$O$_5$S: C, 58.46; H, 5.76. Found: C, 58.39; H, 5.53.

Replacing I3 with J5 and following the same procedure as in the preparation of I4 in Example I provided J6 (65%); 1H NMR (300 MHz, CDCl$_3$) δ 7.53 (d, J=8.6 Hz, 2H), 7.21 (d, J=1.7 Hz, 1H), 7.18 (dd, J=8.4, 2.2 Hz, 1H), 6.88 (d, J=8.6 Hz, 2H), 6.58 (d, J=8.4 Hz, 1H), 4.58 (s, 2H), 4.25 (q, J=7.1 Hz, 2H), 4.05-4.02 (m, 2H), 3.00 (d, J=6.4 Hz, 2H), 2.44 (t, J=7.4 Hz, 2H), 2.26-2.16 (m, 1H), 2.22 (s, 3H), 2.00-1.92 (m, 2H), 1.29 (t, J=7.1 Hz, 3H); MS (ES) m/z: 504 (M+Na+). Anal. Calcd for C$_{24}$H$_{26}$F$_3$NO$_4$S: C, 59.86; H, 5.44; N, 2.91. Found: C, 59.85; H, 5.31; N, 2.93.

Following general procedure 2 in Example A gave Compound 11 (94%); 1H NMR (300 MHz, CDCl$_3$) δ 7.52 (d, J=8.6 Hz, 2H), 7.19 (s, 1H), 7.15 (d, J=8.2 Hz, 1H), 6.88 (d, J=8.6 Hz, 2H), 6.58 (d, J=7.8 Hz, 1H), 4.53 (s, 2H), 4.02 (m, 2H), 2.98 (d, J=6.2 Hz, 2H), 2.42 (t, J=7.3 Hz, 2H), 2.18 (m, 4H), 1.97-1.90 (m, 2H); MS (ES) m/z: 476 (M+Na+). Anal. Calcd for C$_{22}$H$_{22}$F$_3$NO$_4$S+0.3 H$_2$O: C57.58; H, 4.96; N, 3.05. Found: C, 57.40; H, 4.73; N, 2.96.

Example K
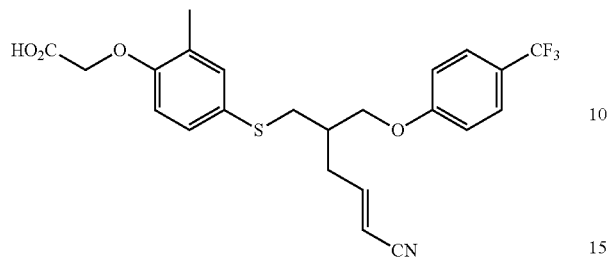
Compound 12
{4-[5-Cyano-2-(4-trifluoromethyl-phenoxymethyl)-pent-4-enylsulfanyl]-2-methyl-phenoxy}-acetic acid
Scheme K
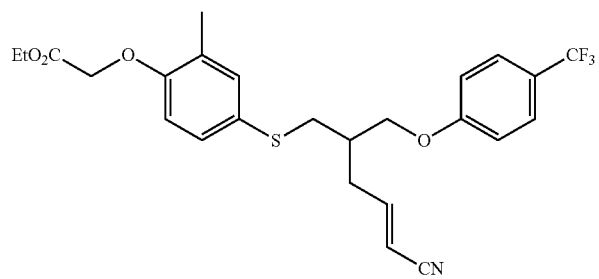 [SMILES: Cc1cc(SCC(C/C=C/C#N)COc2ccc(C(F)(F)F)cc2)ccc1OCC(=O)O]
K1
{4-[5-Cyano-2-(4-trifluoromethyl-phenoxymethyl)-pent-4-enylsulfanyl]-2-methyl-phenoxy}-acetic acid ethyl ester
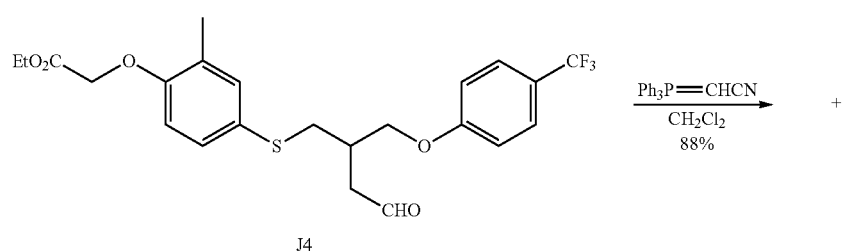
J4
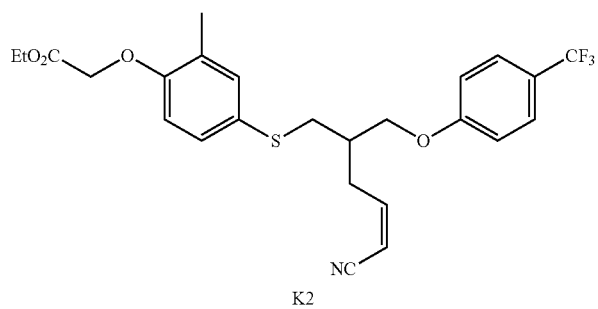
K2

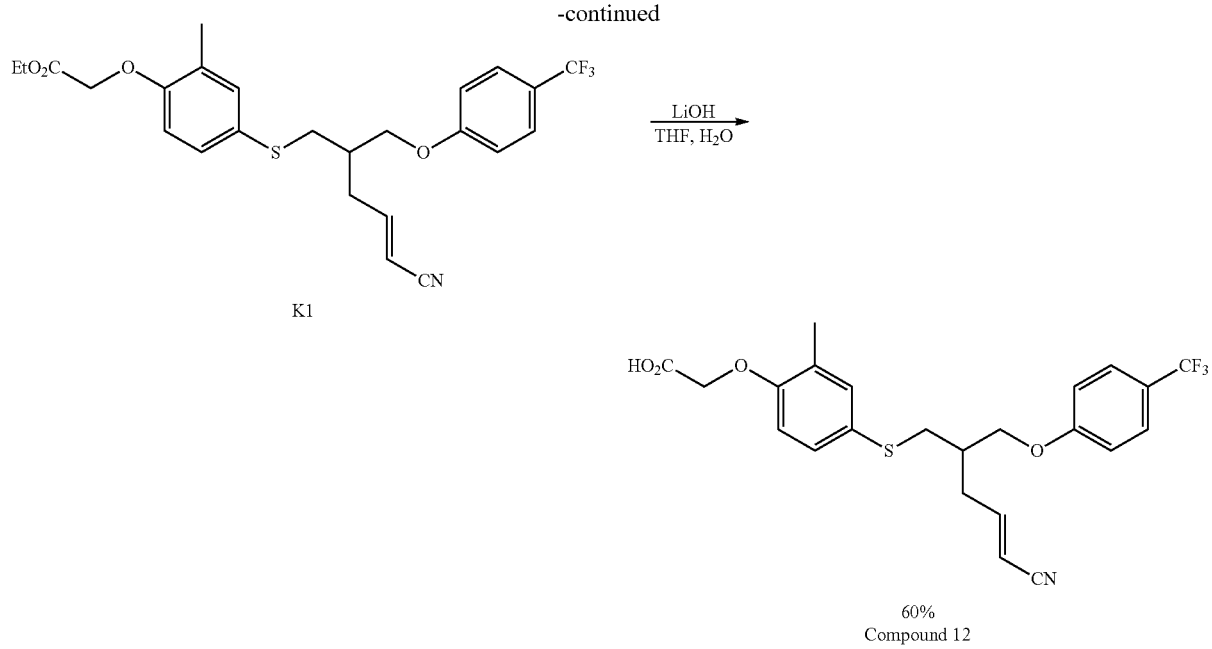

K1

A mixture of J4 (47 mg, 0.10 mmol) and (triphenylphosphoranylidene) acetonitrile (181 mg, 0.601 mmol) in CH$_2$Cl$_2$ (1 mL) was refluxed overnight, concentrated, and purified by column chromatography (EtOAc/hexane: 1/9) to give a mixture of K1 and K2. K1: 1H NMR (300 MHz, CDCl$_3$) δ 7.54 (d, J=8.6 Hz, 2H), 7.20 (d, J=1.7 Hz, 1H), 7.16 (dd, J=8.4, 2.2 Hz, 1H), 6.89 (d, J=8.6 Hz, 2H), 6.72-6.61 (m, 1H), 6.58 (d, J=8.4 Hz, 1H), 5.33 (d, J=16.3 Hz, 1H), 4.59 (s, 2H), 4.26 (q, J=7.1 Hz, 2H), 3.99 (d, J=5.1 Hz, 2H), 2.95 (m, 2H), 2.51 (m, 2H), 2.24 (s, 3H), 2.24-2.17 (m, 1H), 1.30 (t, J=7.1 Hz, 3H); MS (ES) m/z: 516 (M+Na+); K2: 1H NMR (300 MHz, CDCl$_3$) δ 7.52 (d, J=8.6 Hz, 2H), 7.21 (s, 1H), 7.17 (dd, J=8.4, 2.2 Hz, 1H), 6.90 (d, J=8.6 Hz, 2H), 6.58 (d, J=8.4 Hz, 1H), 6.49 (dt, J=10.9, 7.8 Hz, 1H), 5.40 (d, J=10.9 Hz, 1H), 4.58 (s, 2H), 4.26 (q, J=7.1 Hz, 2H), 4.03-4.00 (m, 2H), 2.98 (m, 2H), 2.73 (m, 2H), 2.22 (m, 4H), 1.30 (t, J=7.1 Hz, 3H); MS (ES) m/z: 516 (M+Na+).

Using K1 as the starting material and following general procedure 2 in Example A gave Compound 12 (60%); 1H NMR (300 MHz, CDCl$_3$) δ 7.52 (d, J=8.6 Hz, 2H), 7.17 (s, 1H), 7.13 (dd, J=8.0 Hz, 1H), 6.88 (d, J=8.6 Hz, 2H), 6.67-6.57 (m, 2H), 5.28 (d, J=16.3 Hz, 1H), 4.54 (s, 2H), 3.98 (d, J=5.0 Hz, 2H), 2.93 (m, 2H), 2.49 (t, J=6.9 Hz, 2H), 2.19 (s, 3H), 2.19-2.13 (m, 1H); MS (ES) m/z: 488 (M+Na+).

Example L

Compound 14

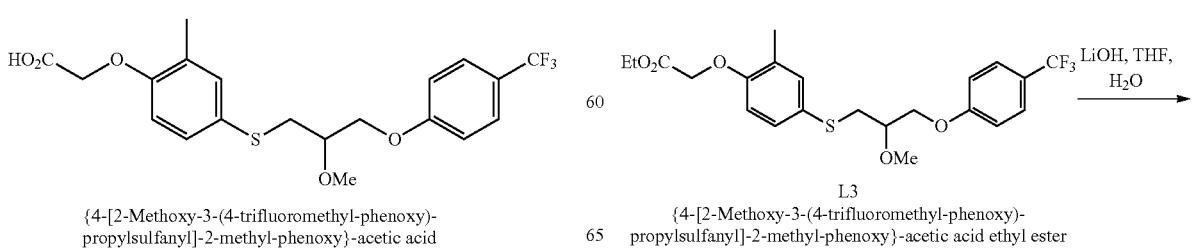

{4-[2-Methoxy-3-(4-trifluoromethyl-phenoxy)-propylsulfanyl]-2-methyl-phenoxy}-acetic acid Scheme L

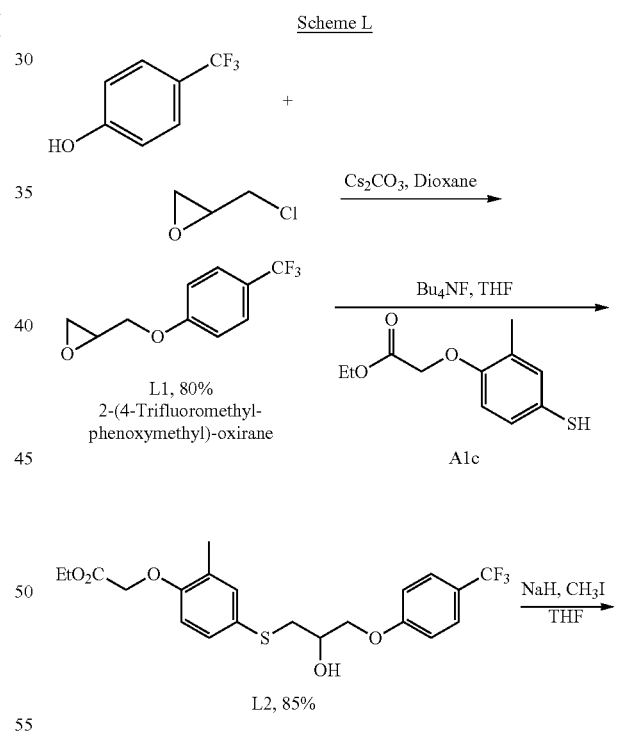

L1, 80%
2-(4-Trifluoromethyl-phenoxymethyl)-oxirane

L2, 85%

L3
{4-[2-Methoxy-3-(4-trifluoromethyl-phenoxy)-propylsulfanyl]-2-methyl-phenoxy}-acetic acid ethyl ester

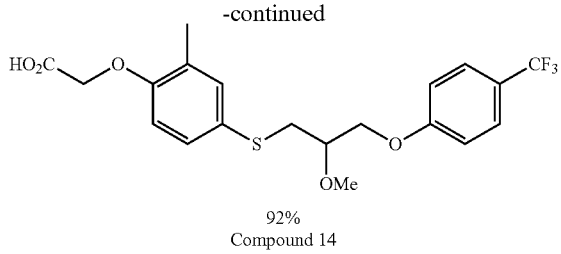

92%
Compound 14

A mixture of 4-trifluoromethylphenol (7.80 g, 48.1 mmol), 2-chloromethyloxirane (11.2 g, 121 mmol), and Cs$_2$CO$_3$ (15.7 g, 48.2 mmol) in dioxane (8 mL) was refluxed for 3-4 h and then allowed to cool to room temperature. Water and Et$_2$O were added, the organic phase was separated, and the aqueous phase was extracted with Et$_2$O. The combined organic layers were dried, concentrated, and column chromatographed (CH$_2$Cl$_2$/hexane: 1/1) to provide 8.40 g (80%) of L1; 1H NMR (300 MHz, CDCl$_3$) δ 7.55 (d, J=8.5 Hz, 2H), 6.99 (d, J=8.5 Hz, 2H), 4.29 (dd, J=11.1, 3.0 Hz, 1H), 3.98 (dd, J=11.1, 5.8 Hz, 1H), 3.37 (m, 1H), 2.93 (m, 1H), 2.77 (dd, J=4.9, 2.6 Hz, 1H).

To a mixture of L1 (2.57 g, 11.8 mmol) and (4-mercapto-2-methyl-phenoxy)acetic acid ethyl ester A1c (4.00 g, 17.7 mmol) in THF (20 mL) was added 1.0 M tetrabutylammonium fluoride in THF (0.44 mL, 0.44 mmol). The reaction mixture was stirred at room temperature for 1.5 h, heated at 60° C. for 1 h, concentrated, and purified by column chromatography to give 4.45 g (85%) of L2; 1H NMR (400 MHz, CDCl$_3$) δ 7.50 (d, J=8.9 Hz, 2H), 7.25 (d, J=2.2 Hz, 1H), 7.21 (dd, J=8.4, 2.3 Hz, 1H), 6.89 (d, J=8.8 Hz, 2H), 6.58 (d, J=8.4 Hz, 1H), 4.58 (s, 2H), 4.24 (q, J=7.1 Hz, 2H), 4.05-4.00 (m, 3H), 3.13 (dd, J=13.7, 5.1 Hz, 1H), 3.04 (dd, J=13.9, 6.5 Hz, 1H), 2.92 (d, J=4.2 Hz, 1H), 2.23 (s, 3H), 1.28 (t, J=7.1 Hz, 3H); MS (ES) m/z: 467 (M+Na+).

General Procedure 4 for Alkylation of Alcohols:

To a suspension of NaH (20 mg, 0.50 mmol, 60% in mineral oil) in THF (1 mL) was added a solution of L2 (222 mg, 0.500 mmol) in THF (1 mL) at room temperature. After 30 min, CH$_3$I (213 mg, 1.50 mmol) was introduced. The reaction mixture was stirred overnight, diluted with water, and extracted with Et$_2$O. The extracts were dried, concentrated, and purified by column chromatography (EtOAc/hexane:⅙) to give L3; 1H NMR (300 MHz, CDCl$_3$) δ 7.52 (d, J=8.6 Hz, 2H), 7.24 (d, J=1.7 Hz, 1H), 7.19 (dd, J=8.4, 2.1 Hz, 1H), 6.91 (d, J=8.5 Hz, 2H), 6.57 (d, J=8.4 Hz, 1H), 4.57 (s, 2H), 4.25 (q, J=7.1 Hz, 2H), 4.16 (dd, J=10.0, 4.0 Hz, 1H), 4.09 (dd, J=10.0, 5.0 Hz, 1H), 3.67 (m, 1H), 3.44 (s, 3H), 3.13 (d, J=6.2 Hz, 2H), 2.22 (s, 3H), 1.29 (t, J=7.1 Hz, 3H); MS (ES) m/z: 481 (M+Na+).

Following general procedure 2 in Example A gave Compound 14 (92%); 1H NMR (400 MHz, CDCl$_3$) δ 10.21 (brs, 1H), 7.50 (d, J=8.6 Hz, 2H), 7.23 (s, 1H), 7.20 (d, J=8.4 Hz, 1H), 6.89 (d, J=8.5 Hz, 2H), 6.58 (d, J=8.4 Hz, 1H), 4.61 (s, 2H), 4.16 (dd, J=10.0, 3.9 Hz, 1H), 4.09 (dd, J=9.9, 4.9 Hz, 1H), 3.68 (m, 1H), 3.45 (s, 3H), 3.14 (d, J=6.1 Hz, 2H), 2.20 (s, 3H); MS (ES) m/z: 453 (M+Na+).

Example M

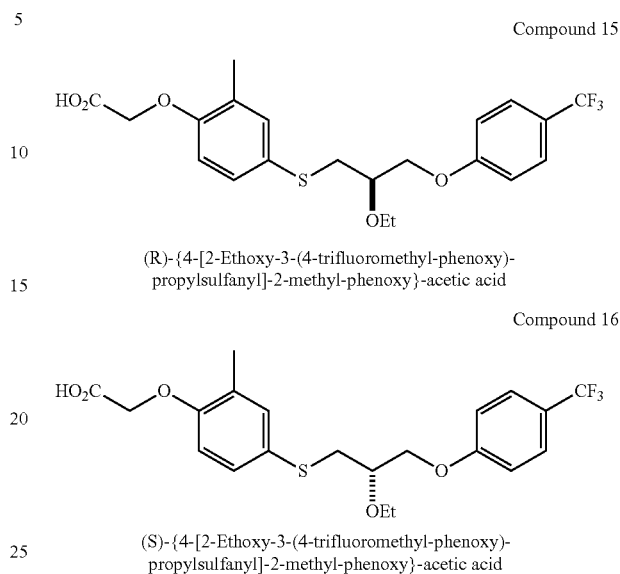

Compound 15

(R)-{4-[2-Ethoxy-3-(4-trifluoromethyl-phenoxy)-propylsulfanyl]-2-methyl-phenoxy}-acetic acid Compound 16

(S)-{4-[2-Ethoxy-3-(4-trifluoromethyl-phenoxy)-propylsulfanyl]-2-methyl-phenoxy}-acetic acid Scheme M

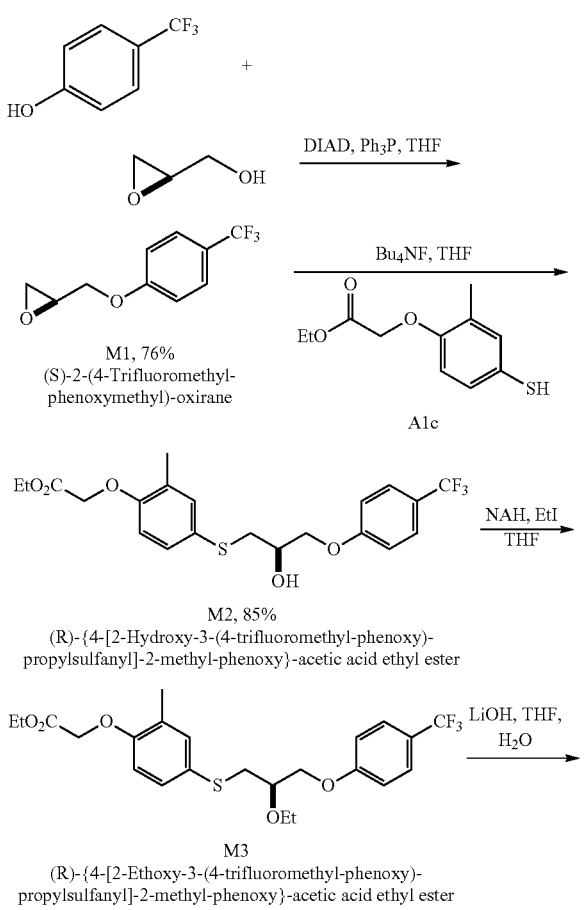

M1, 76%
(S)-2-(4-Trifluoromethyl-phenoxymethyl)-oxirane

A1c

M2, 85%
(R)-{4-[2-Hydroxy-3-(4-trifluoromethyl-phenoxy)-propylsulfanyl]-2-methyl-phenoxy}-acetic acid ethyl ester M3
(R)-{4-[2-Ethoxy-3-(4-trifluoromethyl-phenoxy)-propylsulfanyl]-2-methyl-phenoxy}-acetic acid ethyl ester

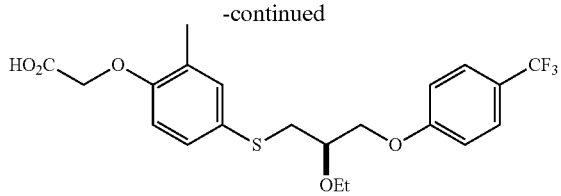

Compound 15

To a mixture of (R)-(+)-glycidol (2.00 g, 27.0 mmol), 4-trifluoromethylphenol (4.38 g, 27.0 mmol), triphenylphosphine (7.08 g, 27.0 mmol) in THF (50 mL) at 0° C. was slowly added diisopropyl azodicarboxylate (5.46 g, 27.0 mmol). The reaction mixture was allowed to warm up to room temperature, stirred at the same temperature overnight, diluted with water, and extracted with Et$_2$O. The extracts were dried and concentrated. The precipitated solid was filtered and rinsed with Et$_2$O. The filtrate was concentrated and column chromatographed (CH$_2$Cl$_2$/hexane:½) to provide 4.50 g (76%) of M1; [α]$_D$ +7.3° (c 1.0, CHCl$_3$); $^1$H NMR (300 MHz, CDCl$_3$) δ 7.54 (d, J=8.7 Hz, 2H), 6.98 (d, J=8.7 Hz, 2H), 4.29 (dd, J=11.1, 2.9 Hz, 1H), 3.96 (dd, J=11.1, 5.8 Hz, 1H), 3.39-3.33 (m, 1H), 2.92 (t, J=4.5 Hz, 1H), 2.76 (dd, J=4.9, 2.6 Hz, 1H).

To a mixture of M1 (2.11 g, 9.68 mmol), (4-mercapto-2-methyl-phenoxy) acetic acid ethyl ester A1c (3.28 g, 14.5 mmol) in THF (10 mL) was added 1.0 M tetrabutylammonium fluoride in THF (0.965 mL, 0.965 mmol). After stirring for 8 h, the solvent was evaporated and the residue was purified by column chromatography twice (EtOAc/hexane: 2/7 and EtOAc/CH2Cl2: 1/1) to give 3.69 g (85%) of M2; [α]$_D$ +32.5° (c 1.0, CHCl$_3$); $^1$H NMR (300 MHz, CDCl$_3$) δ 7.53 (d, J=8.8 Hz, 2H), 7.26 (s, 1H), 7.23 (dd, J=8.4, 2.3 Hz, 1H), 6.91 (d, J=8.8 Hz, 2H), 6.60 (d, J=8.4 Hz, 1H), 4.59 (s, 2H), 4.26 (q, J=7.1 Hz, 2H), 4.08-4.02 (m, 1H), 4.05 (s, 2H), 3.17-3.01 (m, 2H), 2.70 (brs, 1H), 2.24 (s, 3H), 1.29 (t, J=7.1 Hz, 3H); MS (ES) m/z: 467 (M+Na+).

Following general procedure 4 in Example L gave M3; [α]$_D$ +38.9° (c 1.0, CHCl$_3$); $^1$H NMR (300 MHz, CDCl$_3$) δ 7.51 (d, J=8.6 Hz, 2H), 7.24 (d, J=1.7 Hz, 1H), 7.19 (dd, J=8.4, 2.2 Hz, 1H), 6.91 (d, J=8.6 Hz, 2H), 6.57 (d, J=8.4 Hz, 1H), 4.57 (s, 2H), 4.25 (q, J=7.1 Hz, 2H), 4.15 (dd, J=9.9, 4.3 Hz, 1H), 4.07 (dd, J=9.9, 5.1 Hz, 1H), 3.76 (m, 1H), 3.61 (q, J=7.0 Hz, 2H), 3.13-3.11 (m, 2H), 2.23 (s, 3H), 1.29 (t, J=7.1 Hz, 3H), 1.18 (t, J=7.0 Hz, 3H); MS (ES) m/z: 495 (M+Na+). Anal. Calcd for C$_{23}$H$_{27}$F$_3$O$_5$S: C, 58.46; H, 5.76. Found: C, 58.83; H, 5.55.

Following general procedure 2 in Example A gave Compound 15; [α]$_D$ +39.2° (c 1.0, CHCl$_3$); $^1$H NMR (300 MHz, CDCl$_3$) δ 7.51 (d, J=8.7 Hz, 2H), 7.23 (s, 1H), 7.20 (dd, J=8.4, 2.1 Hz, 1H), 6.91 (d, J=8.6 Hz, 2H), 6.59 (d, J=8.4 Hz, 1H), 4.61 (s, 2H), 4.14 (dd, J=9.9, 4.4 Hz, 1H), 4.08 (dd, J=9.9, 5.0 Hz, 1H), 3.77 (m, 1H), 3.61 (q, J=7.0 Hz, 2H), 3.20-3.07 (m, 2H), 2.21 (s, 3H), 1.19 (t, J=7.0 Hz, 3H); MS (ES) m/z: 467 (M+Na+).

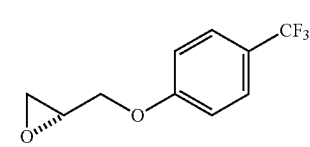

M4

(R)-2-(4-Trifluoromethyl-phenoxymethyl)-oxirane

Following the same procedure as in the preparation of M1 gave M4 (74%); $^1$H NMR (400 MHz, CDCl$_3$) δ 7.54 (d, J=9.0 Hz, 2H), 6.98 (d, J=8.9 Hz, 2H), 4.29 (dd, J=11.1, 2.9 Hz, 1H), 3.96 (dd, J=11.1, 5.8 Hz, 1H), 3.37 (m, 1H), 2.92 (m, 1H), 2.76 (dd, J=4.8, 2.6 Hz, 1H); MS (ES) m/z: 241 (M+Na+).

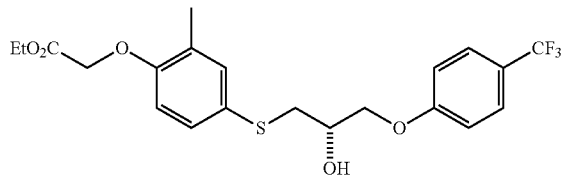 [SMILES: Cc1cc(SCC(O)COc2ccc(C(F)(F)F)cc2)ccc1OCC(=O)O]

M5

(S)-{4-[2-Hydroxy-3-(4-trifluoromethyl-phenoxy)-propylsulfanyl]-2-methyl-phenoxy}-acetic acid ethyl ester Following the same procedure as in the preparation of M2 provided M5 (88%); 1H NMR (300 MHz, CDCl$_3$) δ 7.52 (d, J=8.7 Hz, 2H), 7.26 (s, 1H), 7.22 (dd, J=8.4, 2.3 Hz, 1H), 6.91 (d, J=8.7 Hz, 2H), 6.59 (d, J=8.4 Hz, 1H), 4.59 (s, 2H), 4.25 (q, J=7.1 Hz, 2H), 4.07-4.01 (m, 3H), 3.17-3.01 (m, 2H), 2.72 (brs, 1H), 2.23 (s, 3H), 1.29 (t, J=7.1 Hz, 3H); MS (ES) m/z: 467 (M+Na+).

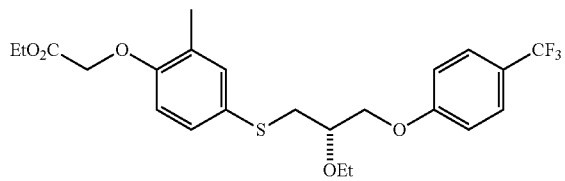 [SMILES: CCO[C@@H](COc1ccc(C(F)(F)F)cc1)CSc1ccc(OCC(=O)O)c(C)c1]

M6

(S)-{4-[2-Hydroxy-3-(4-trifluoromethyl-phenoxy)-propylsulfanyl]-2-methyl-phenoxy}-acetic acid ethyl ester Following general procedure 4 in Example L gave M6; 1H NMR (400 MHz, CDCl$_3$) δ 7.51 (d, J=8.7 Hz, 2H), 7.24 (d, J=2.0 Hz, 1H), 7.19 (dd, J=8.4, 2.3 Hz, 1H), 6.91 (d, J=8.7 Hz, 2H), 6.57 (d, J=8.4 Hz, 1H), 4.57 (s, 2H), 4.25 (q, J=7.1 Hz, 2H), 4.15 (dd, J=9.9, 4.3 Hz, 1H), 4.08 (dd, J=9.9, 5.1 Hz, 1H), 3.76 (m, 1H), 3.61 (q, J=7.0 Hz, 2H), 3.13-3.11 (m, 2H), 2.22 (s, 3H), 1.29 (t, J=7.1 Hz, 3H), 1.18 (t, J=7.0 Hz, 3H); MS (ES) m/z: 495 (M+Na+). Anal. Calcd for C$_{23}$H$_{27}$F$_3$O$_5$S: C, 58.46; H, 5.76. Found: C, 58.82; H, 5.37.

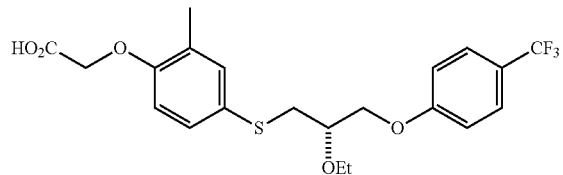

Compound 16

(S)-{4-[2-Ethoxy-3-(4-trifluoromethyl-phenoxy)-propylsulfanyl]-2-methyl-phenoxy}-acetic acid Following general procedure 2 in Example A gave Compound 16; 1H NMR (300 MHz, CDCl$_3$) δ 7.50 (d, J=8.6 Hz, 2H), 7.23 (s, 1H), 7.19 (dd, J=8.4, 1.9 Hz, 1H), 6.90 (d, J=8.6 Hz, 2H), 6.58 (d, J=8.4 Hz, 1H), 4.59 (s, 2H), 4.14 (dd, J=9.9, 4.4 Hz, 1H), 4.08 (dd, J=9.9, 4.9 Hz, 1H), 3.77 (m, 1H), 3.61 (q, J=7.0 Hz, 2H), 3.13 (m, 2H), 2.20 (s, 3H), 1.18 (t, J=7.0 Hz, 3H); MS (ES) m/z: 467 (M+Na+).

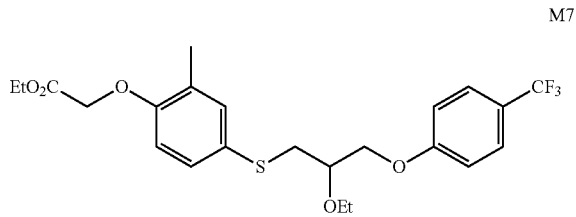

M7

{4-[2-Ethoxy-3-(4-trifluoromethyl-phenoxy)-propylsulfanyl]-2-methyl-phenoxy}-acetic acid ethyl ester Following general procedure 4 in Example L gave M7 (59%); 1H NMR (300 MHz, CDCl$_3$) δ 7.51 (d, J=8.6 Hz, 2H), 7.24 (d, J=1.7 Hz, 1H), 7.19 (dd, J=8.4, 2.2 Hz, 1H), 6.91 (d, J=8.6 Hz, 2H), 6.57 (d, J=8.4 Hz, 1H), 4.57 (s, 2H), 4.25 (q, J=7.1 Hz, 2H), 4.15 (dd, J=9.9, 4.3 Hz, 1H), 4.07 (dd, J=9.9, 5.1 Hz, 1H), 3.76 (m, 1H), 3.60 (q, J=7.0 Hz, 2H), 3.13-3.11 (m, 2H), 2.22 (s, 3H), 1.28 (t, J=7.1 Hz, 3H), 1.18 (t, J=7.0 Hz, 3H); MS (ES) m/z: 495 (M+Na+). Anal. Calcd for C$_{23}$H$_{27}$F$_3$O$_5$S: C, 58.46; H, 5.76. Found: C, 57.62; H, 5.52.

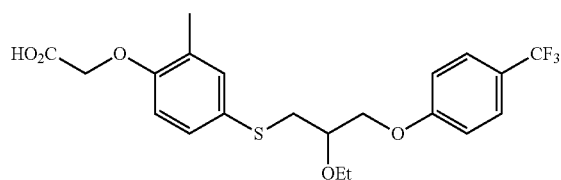

Compound 17

{4-[2-Ethoxy-3-(4-trifluoromethyl-phenoxy)-propylsulfanyl]-2-methyl-phenoxy}-acetic acid Following general procedure 2 in Example A gave Compound 17 (94%); 1H NMR (400 MHz, CDCl$_3$) δ 7.50 (d, J=8.7 Hz, 2H), 7.22 (s, 1H), 7.18 (d, J=8.6 Hz, 1H), 6.90 (d, J=8.7 Hz, 2H), 6.57 (d, J=8.4 Hz, 1H), 4.57 (s, 2H), 4.14 (dd, J=9.9, 4.3 Hz, 1H), 4.07 (dd, J=9.8, 5.0 Hz, 1H), 3.77 (m, 1H), 3.61 (q, J=7.0 Hz, 2H), 3.18-3.08 (m, 2H), 2.19 (s, 3H), 1.18 (t, J=7.0 Hz, 3H); MS (ES) m/z: 467 (M+Na+). Anal. Calcd for C$_{21}$H$_{23}$F$_3$O$_5$S+0.2 H$_2$O: C, 56.29; H, 5.26. Found: C, 56.23; H, 5.27.

M8

{2-Methyl-4-{2-propoxy-3-(4-trifluoromethyl-phenoxy)-propylsulfanyl]-phenoxy}-acetic acid ethyl ester Replacing THF with DMF as solvent and following general procedure 4 in Example L gave M8 (12%); 1H NMR (300 MHz, CDCl$_3$) δ 7.51 (d, J=8.6 Hz, 2H), 7.23 (d, J=1.7 Hz, 1H), 7.19 (dd, J=8.4, 2.2 Hz, 1H), 6.91 (d, J=8.6 Hz, 2H), 6.57 (d, J=8.4 Hz, 1H), 4.57 (s, 2H), 4.25 (q, J=7.1 Hz, 2H), 4.15 (dd, J=9.9, 4.3 Hz, 1H), 4.07 (dd, J=9.9, 5.1 Hz, 1H), 3.75 (m, 1H), 3.50 (t, J=6.7 Hz, 2H), 3.12 (d, J=6.2 Hz, 2H), 2.23 (s, 3H), 1.63-1.51 (m, 2H), 1.29 (t, J=7.1 Hz, 3H), 0.90 (t, J=7.4 Hz, 3H); MS (ES) m/z: 509 (M+Na+).

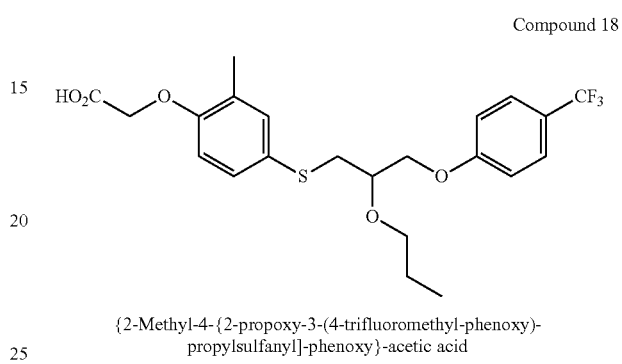

Compound 18

{2-Methyl-4-{2-propoxy-3-(4-trifluoromethyl-phenoxy)-propylsulfanyl]-phenoxy}-acetic acid Following general procedure 2 in Example A gave Compound 18 (92%); 1H NMR (400 MHz, CDCl$_3$) δ 7.51 (d, J=8.6 Hz, 2H), 7.24 (s, 1H), 7.20 (d, J=8.3 Hz, 1H), 6.91 (d, J=8.5 Hz, 2H), 6.59 (d, J=8.4 Hz, 1H), 4.63 (s, 2H), 4.15 (dd, J=9.8, 4.3 Hz, 1H), 4.08 (dd, J=9.8, 5.1 Hz, 1H), 3.76 (m, 1H), 3.51 (t, J=6.6 Hz, 2H), 3.15-3.13 (m, 2H), 2.22 (s, 3H), 1.57 (m, 2H), 0.90 (t, J=7.4 Hz, 3H); MS (ES) m/z: 481 (M+Na+).

M9

{4-[2-Butoxy-3-(4-trifluoromethyl-phenoxy)-propylsulfanyl]-2-methyl-phenoxy}-acetic acid ethyl ester Replacing THF with DMF as solvent and following general procedure 4 in Example L gave M9 (10%); 1H NMR (300 MHz, CDCl$_3$) δ 7.51 (d, J=8.6 Hz, 2H), 7.23 (d, J=1.9 Hz, 1H), 7.18 (dd, J=8.4, 2.2 Hz, 1H), 6.91 (d, J=8.6 Hz, 2H), 6.57 (d, J=8.4 Hz, 1H), 4.57 (s, 2H), 4.26 (q, J=7.1 Hz, 2H), 4.15 (dd, J=9.9, 4.4 Hz, 1H), 4.07 (dd, J=9.9, 5.2 Hz, 1H), 3.75 (m, 1H), 3.54 (t, J=6.6 Hz, 2H), 3.12 (d, J=6.2 Hz, 2H), 2.23 (s, 3H), 1.58-1.48 (m, 2H), 1.41-1.34 (m, 2H), 1.29 (t, J=7.1 Hz, 3H), 0.90 (t, J=7.3 Hz, 3H); MS (ES) m/z: 523 (M+Na+).

Compound 19

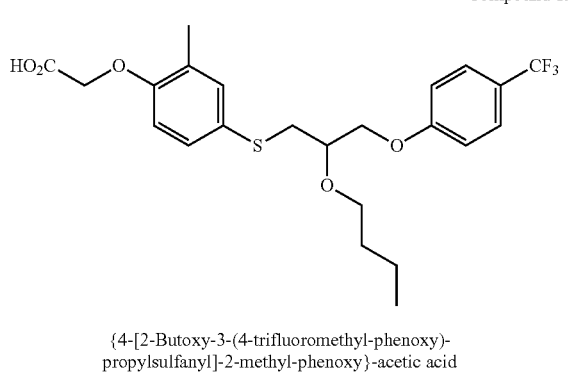

{4-[2-Butoxy-3-(4-trifluoromethyl-phenoxy)-propylsulfanyl]-2-methyl-phenoxy}-acetic acid Following general procedure 2 in Example A gave Compound 19 (92%); 1H NMR (400 MHz, CDCl$_3$) δ 7.47 (m, 2H), 7.25-7.23 (m, 1H), 7.13-7.12 (m, 1H), 6.87 (m, 2H), 6.52 (m, 1H), 4.37 (s, 2H), 4.08-4.05 (m, 2H), 3.71 (m, 1H), 3.52-3.50 (m, 2H), 3.08 (m, 2H), 2.11 (s, 3H), 1.49 (m, 2H), 1.32-1.25 (m, 2H), 0.87 (m, 3H); MS (ES) m/z: 495 (M+Na+). Anal. Calcd for C$_{23}$H$_{27}$F$_3$O$_5$S+0.3 H$_2$O: C, 57.80; H, 5.82. Found: C, 57.78; H, 6.00.

M10

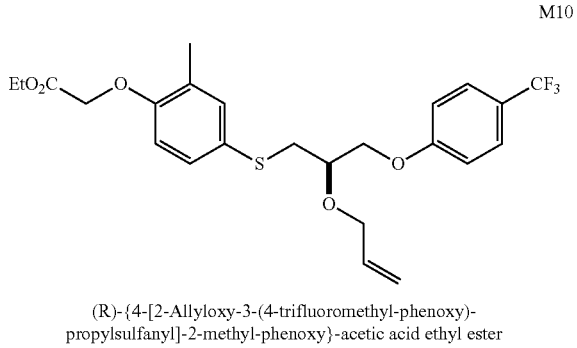

(R)-{4-[2-Allyloxy-3-(4-trifluoromethyl-phenoxy)-propylsulfanyl]-2-methyl-phenoxy}-acetic acid ethyl ester Following general procedure 4 in Example L gave M10; 1H NMR (400 MHz, CDCl$_3$) δ 7.52 (d, J=8.7 Hz, 2H), 7.23 (s, 1H), 7.19 (dd, J=8.4, 2.3 Hz, 1H), 6.91 (d, J=8.7 Hz, 2H), 6.57 (d, J=8.4 Hz, 1H), 5.93-5.83 (m, 1H), 5.23 (dd, J=17.2, 1.5 Hz, 1H), 5.16 (dd, J=10.3, 1.0 Hz, 1H), 4.58 (s, 2H), 4.26 (q, J=7.1 Hz, 2H), 4.17 (dd, J=9.9, 4.1 Hz, 1H), 4.13-4.05 (m, 3H), 3.82 (m, 1H), 3.13 (d, J=6.2 Hz, 2H), 2.23 (s, 3H), 1.29 (t, J=7.1 Hz, 3H); MS (ES) m/z: 507 (M+Na+).

Compound 20

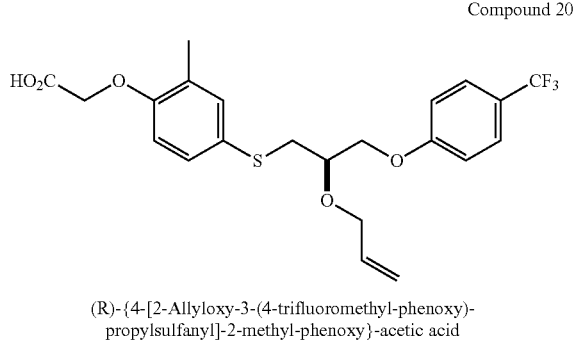

(R)-{4-[2-Allyloxy-3-(4-trifluoromethyl-phenoxy)-propylsulfanyl]-2-methyl-phenoxy}-acetic acid Following general procedure 2 in Example A gave Compound 20; 1H NMR (300 MHz, MeOH-d4) δ 7.54 (d, J=8.6 Hz, 2H), 7.24 (s, 1H), 7.21 (d, J=2.1 Hz, 1H), 6.99 (d, J=8.6 Hz, 2H), 6.70 (d, J=8.1 Hz, 1H), 5.93-5.80 (m, 1H), 5.20 (dd, J=17.2, 1.6 Hz, 1H), 5.10 (dd, J=10.4, 1.3 Hz, 1H), 4.62 (s, 2H), 4.19 (dd, J=10.3, 4.0 Hz, 1H), 4.11 (dd, J=10.3, 5.1 Hz, 1H), 4.09-4.06 (m, 2H), 3.81 (m, 1H), 3.12 (d, J=6.4 Hz, 2H), 2.18 (s, 3H); MS (ES) m/z: 479 (M+Na+).

M11

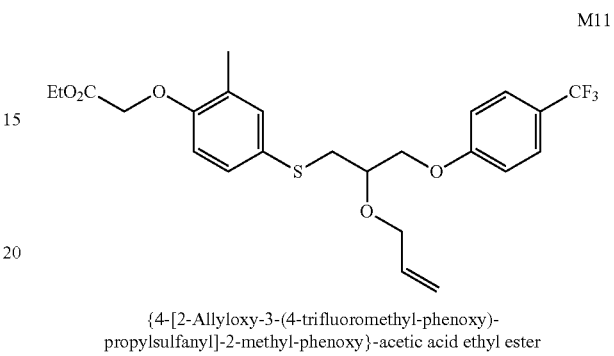

{4-[2-Allyloxy-3-(4-trifluoromethyl-phenoxy)-propylsulfanyl]-2-methyl-phenoxy}-acetic acid ethyl ester Replacing NaH with NaHMDS as a base and following general procedure 4 in Example L gave M11 (58%); 1H NMR (400 MHz, CDCl$_3$) δ 7.51 (d, J=8.8 Hz, 2H), 7.23 (d, J=2.1 Hz, 1H), 7.19 (dd, J=8.4, 2.3 Hz, 1H), 6.91 (d, J=8.8 Hz, 2H), 6.57 (d, J=8.4 Hz, 1H), 5.93-5.83 (m, 1H), 5.23 (dd, J=17.2, 1.5 Hz, 1H), 5.16 (d, J=10.3 Hz, 1H), 4.57 (s, 2H), 4.25 (q, J=7.1 Hz, 2H), 4.16 (dd, J=10.0, 4.1 Hz, 1H), 4.11-4.08 (m, 3H), 3.82 (m, 1H), 3.13 (d, J=6.1 Hz, 2H), 2.22 (s, 3H), 1.29 (t, J=7.1 Hz, 3H). Anal. Calcd for C$_{24}$H$_{27}$F$_3$O$_5$S: C, 59.49; H, 5.62. Found: C, 59.76; H, 5.71.

Compound 21

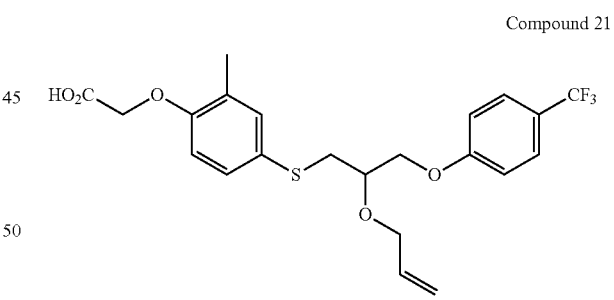

{4-[2-Allyloxy-3-(4-trifluoromethyl-phenoxy)-propylsulfanyl]-2-methyl-phenoxy}-acetic acid Following general procedure 2 in Example A gave Compound 21 (90%); 1H NMR (400 MHz, CDCl$_3$) δ 7.49 (d, J=8.5 Hz, 2H), 7.18 (s, 1H), 7.14 (d, J=7.1 Hz, 1H), 6.89 (d, J=8.5 Hz, 2H), 6.53 (m, 1H), 5.91-5.82 (m, 1H), 5.21 (d, J=17.2, 1H), 5.15 (d, J=10.3 Hz, 1H), 4.44 (s, 2H), 4.13 (dd, J=9.8, 4.2 Hz, 1H), 4.09-4.06 (m, 3H), 3.82 (m, 1H), 3.11 (d, J=4.5 Hz, 2H), 2.15 (s, 3H); MS (ES) m/z: 455 (M−H+).

M12

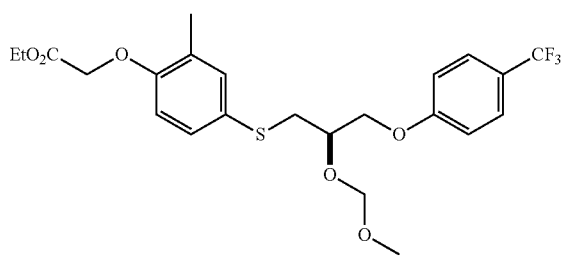

(R)-{4-[2-Methoxymethoxy-3-(4-trifluoromethyl-phenoxy)-propylsulfanyl]-2-methyl-phenoxy}-acetic acid ethyl ester Replacing NaH with iPr$_2$NEt as a base and following general procedure 4 in Example L gave M12 (79%); [α]$_D$ +47.8° (c 1.0, CHCl$_3$); $^1$H NMR (400 MHz, CDCl$_3$) δ 7.51 (d, J=8.9 Hz, 2H), 7.23 (d, J=2.2 Hz, 1H), 7.18 (dd, J=8.4, 2.3 Hz, 1H), 6.90 (d, J=8.8 Hz, 2H), 6.56 (d, J=8.4 Hz, 1H), 4.73 (s, 2H), 4.57 (s, 2H), 4.25 (q, J=7.1 Hz, 2H), 4.19-4.10 (m, 2H), 4.05 (m, 1H), 3.39 (s, 3H), 3.18-3.16 (m, 2H), 2.22 (s, 3H), 1.29 (t, J=7.1 Hz, 3H); MS (ES) m/z: 511 (M+Na+).

Compound 22

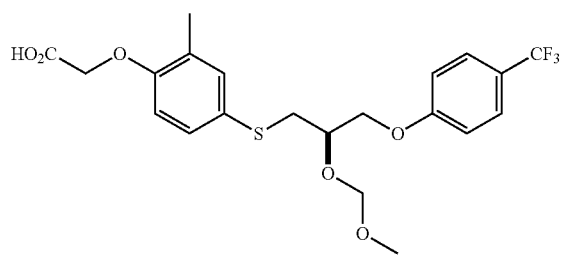

(R)-{4-[2-Methoxymethoxy-3-(4-trifluoromethyl-phenoxy)-propylsulfanyl]-2-methyl-phenoxy}-acetic acid Following general procedure 2 in Example A gave Compound 22 (95%); [α]$_D$ +49.2° (c 1.0, CHCl$_3$); $^1$H NMR (400 MHz, CDCl$_3$) δ 7.51 (d, J=8.6 Hz, 2H), 7.23 (s, 1H), 7.19 (d, J=8.4 Hz, 1H), 6.89 (d, J=8.6 Hz, 2H), 6.59 (d, J=8.4 Hz, 1H), 4.74 (s, 2H), 4.60 (s, 2H), 4.19-4.10 (m, 2H), 4.05 (m, 1H), 3.40 (s, 3H), 3.19-3.17 (m, 2H), 2.21 (s, 3H); MS (ES) m/z: 483 (M+Na+). Anal. Calcd for C$_{21}$H$_{23}$F$_3$O$_6$S: C, 54.78; H, 5.03. Found: C, 54.51; H, 4.90.

M13

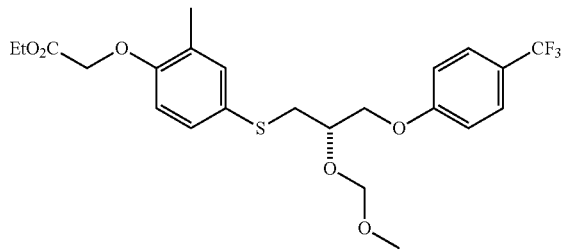 [SMILES: CCCOC(COc1ccc(C(F)(F)F)cc1)CSc1ccc(OCC(=O)O)c(C)c1]

(S)-{4-[2-Methoxymethoxy-3-(4-trifluoromethyl-phenoxy)-propylsulfanyl]-2-methyl-phenoxy}-acetic acid ethyl ester Replacing NaH with iPr$_2$NEt as a base and following general procedure 4 gave M13 (73%); 1H NMR (300 MHz, CDCl$_3$) δ 7.51 (d, J=8.7 Hz, 2H), 7.22 (s, 1H), 7.18 (dd, J=8.4, 2.1 Hz, 1H), 6.90 (d, J=8.6 Hz, 2H), 6.57 (d, J=8.4 Hz, 1H), 4.73 (s, 2H), 4.56 (s, 2H), 4.25 (q, J=7.1 Hz, 2H), 4.18-4.13 (m, 1H), 4.09-4.03 (m, 1H), 3.39 (s, 3H), 3.17 (d, J=6.2 Hz, 2H), 2.22 (s, 3H), 1.29 (t, J=7.1 Hz, 3H); MS (ES) m/z: 511 (M+Na+).

Compound 23

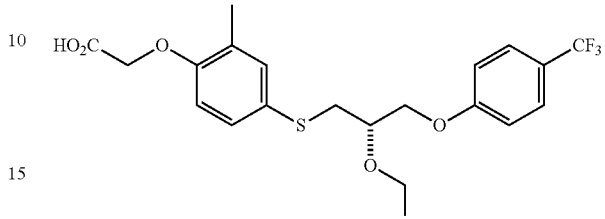

(S)-{4-[2-Methoxymethoxy-3-(4-trifluoromethyl-phenoxy)-propylsulfanyl]-2-methyl-phenoxy}-acetic acid Following general procedure 2 in Example A gave Compound 23 (91%); 1H NMR (400 MHz, CDCl$_3$) δ 7.51 (d, J=8.7 Hz, 2H), 7.23 (s, 1H), 7.19 (d, J=8.4 Hz, 1H), 6.90 (d, J=8.6 Hz, 2H), 6.59 (d, J=8.4 Hz, 1H), 4.74 (s, 2H), 4.60 (s, 2H), 4.19-4.10 (m, 2H), 4.08-4.04 (m, 1H), 3.40 (s, 3H), 3.19-3.17 (m, 2H), 2.21 (s, 3H); MS (ES) m/z: 483 (M+Na+).

M14

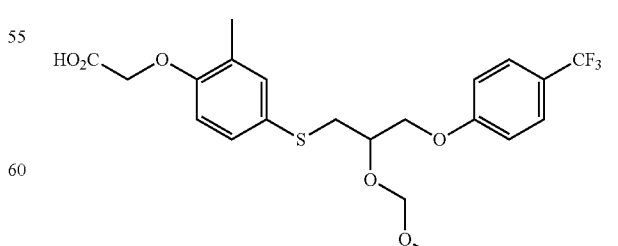

{4-[2-Methoxymethoxy-3-(4-trifluoromethyl-phenoxy)-propylsulfanyl]-2-methyl-phenoxy}-acetic acid ethyl ester Following general procedure 4 in Example L gave M14 (84%); 1H NMR (400 MHz, CDCl$_3$) δ 7.51 (d, J=8.7 Hz, 2H), 7.23 (d, J=2.1 Hz, 1H), 7.18 (dd, J=8.4, 2.2 Hz, 1H), 6.90 (d, J=8.7 Hz, 2H), 6.56 (d, J=8.4 Hz, 1H), 4.73 (s, 2H), 4.57 (s, 2H), 4.25 (q, J=7.1 Hz, 2H), 4.19-4.10 (m, 2H), 4.05 (m, 1H), 3.39 (s, 3H), 3.18-3.16 (m, 2H), 2.22 (s, 3H), 1.29 (t, J=7.1 Hz, 3H); MS (ES) m/z: 511 (M+Na+). Anal. Calcd for C$_{23}$H$_{27}$F$_3$O$_6$S: C, 56.55; H, 5.57. Found: C, 56.68; H, 5.38.

Compound 24

{4-[2-Methoxymethoxy-3-(4-trifluoromethyl-phenoxy)-propylsulfanyl]-2-methyl-phenoxy}-acetic acid Following general procedure 2 in Example A gave Compound 24 (91%); 1H NMR (400 MHz, CDCl₃) δ 7.50 (d, J=8.6 Hz, 2H), 7.23 (s, 1H), 7.19 (d, J=8.4 Hz, 1H), 6.89 (d, J=8.5 Hz, 2H), 6.58 (d, J=8.4 Hz, 1H), 4.74 (s, 2H), 4.61 (s, 2H), 4.18-4.10 (m, 2H), 4.06 (m, 1H), 3.40 (s, 3H), 3.19-3.17 (m, 2H), 2.21 (s, 3H); MS (ES) m/z: 483 (M+Na+). Anal. Calcd for C₂₁H₂₃F₃O₆S+0.2 H₂O: C, 54.35; H, 5.08. Found: C, 54.25; H, 5.13.

M15

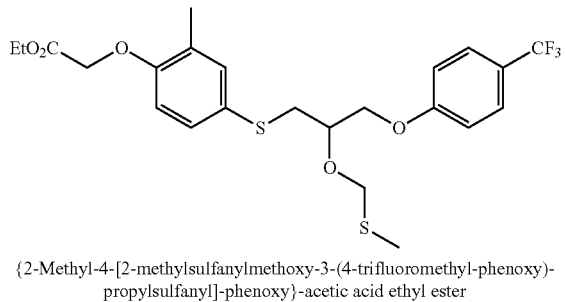

{2-Methyl-4-[2-methylsulfanylmethoxy-3-(4-trifluoromethyl-phenoxy)-propylsulfanyl]-phenoxy}-acetic acid ethyl ester A reaction mixture of L1b (1.08 g, 2.43 mmol), Ac₂O (2.56 mL, 27.2 mmol), and DMSO (3.84 mL) was stirred at room temperature for 24 h, and diluted with saturated NaHCO₃ and Et₂O. The organic phase was separated, washed with water (×3), dried, and column chromatographed (EtOAc/hexane: ¼) to give 61 mg (5%) of M15 as a by-product; 1H NMR (400 MHz, CDCl₃) δ 7.51 (d, J=8.6 Hz, 2H), 7.24 (s, 1H), 7.20 (dd, J=8.4, 1.9 Hz, 1H), 6.90 (d, J=8.6 Hz, 2H), 6.57 (d, J=8.4 Hz, 1H), 4.74 (d, J=6.0 Hz, 2H), 4.57 (s, 2H), 4.25 (q, J=7.1 Hz, 2H), 4.21-4.10 (m, 3H), 3.15 (d, J=6.0 Hz, 2H), 2.23 (s, 3H), 2.16 (s, 3H), 1.29 (t, J=7.1 Hz, 3H); MS (ES) m/z: 527 (M+Na+).

Compound 25

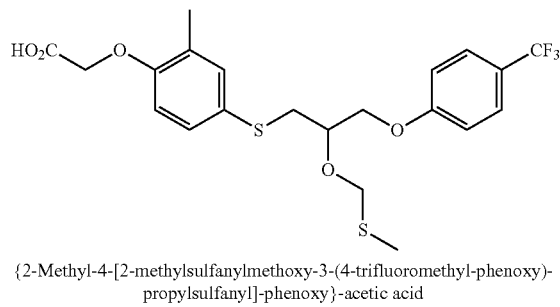

{2-Methyl-4-[2-methylsulfanylmethoxy-3-(4-trifluoromethyl-phenoxy)-propylsulfanyl]-phenoxy}-acetic acid Following general procedure 2 in Example A gave Compound 25 (92%); 1H NMR (300 MHz, CDCl₃) δ 9.45 (brs, 1H), 7.51 (d, J=8.5 Hz, 2H), 7.25 (s, 1H), 7.21 (d, J=8.5 Hz, 1H), 6.90 (d, J=8.4 Hz, 2H), 6.59 (d, J=8.4 Hz, 1H), 4.74 (d, J=3.0 Hz, 2H), 4.63 (s, 2H), 4.19-4.10 (m, 3H), 3.16 (d, J=5.7 Hz, 2H), 2.21 (s, 3H), 2.16 (s, 3H); MS (ES) m/z: 499 (M+Na+).

M16

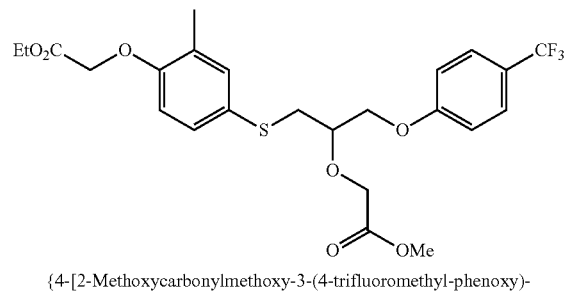

{4-[2-Methoxycarbonylmethoxy-3-(4-trifluoromethyl-phenoxy)-propylsulfanyl]-2-methyl-phenoxy}-acetic acid ethyl ester Following general procedure 4 in Example L gave M16; 1H NMR (300 MHz, CDCl₃) δ 7.51 (d, J=8.6 Hz, 2H), 7.24 (d, J=1.9 Hz, 1H), 7.19 (dd, J=8.4, 2.2 Hz, 1H), 6.91 (d, J=8.7 Hz, 2H), 6.57 (d, J=8.4 Hz, 1H), 4.58 (s, 2H), 4.28-4.23 (m, 5H), 4.19-4.13 (m, 2H), 3.89-3.86 (m, 1H), 3.69 (s, 2H), 3.25-3.14 (m, 2H), 2.23 (s, 3H), 1.29 (t, J=7.1 Hz, 3H); MS (ES) m/z: 539 (M+Na+).

Compound 26

{4-[2-Carboxymethoxy-3-(4-trifluoromethyl-phenoxy)-propylsulfanyl]-2-methyl-phenoxy}-acetic acid Following general procedure 2 in Example A gave Compound 26 (97%); 1H NMR (300 MHz, MeOH-d4) δ 7.53 (d, J=8.7 Hz, 2H), 7.24 (s, 1H), 7.22 (dd, J=8.5, 2.2 Hz, 1H), 6.97 (d, J=8.7 Hz, 2H), 6.68 (d, J=8.4 Hz, 1H), 4.61 (s, 2H), 4.24-4.15 (m, 4H), 3.88-3.84 (m, 1H), 3.20-3.16 (m, 2H), 2.17 (s, 3H); MS (ES) m/z: 497 (M+Na+).

M17

{4-[2-(5-Chloro-thiophen-2-ylmethoxy)-3-(4-trifluoromethyl-phenoxy)-propylsulfanyl]-2-methyl-phenoxy}-acetic acid ethyl ester Replacing NaH with sodium bis(trimethylsilyl)amide and following general procedure 4 gave M17 (26%); 1H NMR (300 MHz, CDCl₃) δ 7.52 (d, J=8.6 Hz, 2H), 7.20 (d, J=1.7

Hz, 1H), 7.15 (dd, J=8.4, 2.1 Hz, 1H), 6.90 (d, J=8.6 Hz, 2H), 6.72 (d, J=3.7 Hz, 1H), 6.63 (d, J=3.7 Hz, 1H), 6.57 (d, J=8.4 Hz, 1H), 4.67 (d, J=1.5 Hz, 2H), 4.59 (s, 2H), 4.26 (q, J=7.1 Hz, 2H), 4.18 (dd, J=10.1, 3.9 Hz, 1H), 4.09 (dd, J=10.1, 5.5 Hz, 1H), 3.92-3.85 (m, 1H), 3.09 (d, J=6.2 Hz, 2H), 2.23 (s, 3H), 1.30 (t, J=7.1 Hz, 3H); MS (ES) m/z: 597 (M+Na+).

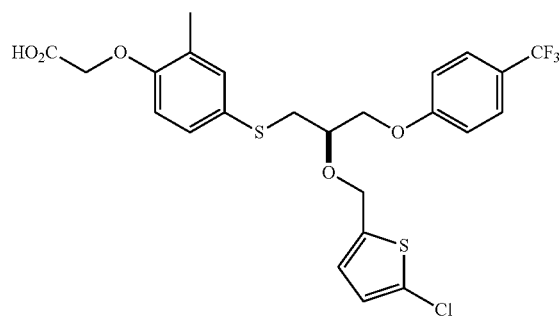 [SMILES: Cc1cc(SC[C@@H](COc2ccc(C(F)(F)F)cc2)OCc2ccc(Cl)s2)ccc1OCC(=O)O]

Compound 27

{4-[2-(5-Chloro-thiophen-2-ylmethoxy)-3-(4-trifluoromethyl-phenoxy)-propylsulfanyl]-2-methyl-phenoxy}-acetic acid Following general procedure 2 in Example A gave Compound 27 (93%); 1H NMR (300 MHz, CDCl$_3$) δ 7.48 (d, J=8.6 Hz, 2H), 7.11 (s, 1H), 7.07 (d, J=8.3 Hz, 1H), 6.85 (d, J=8.6 Hz, 2H), 6.68 (d, J=3.7 Hz, 1H), 6.62 (d, J=3.7 Hz, 1H), 6.50 (d, J=7.9 Hz, 1H), 4.64 (s, 2H), 4.36 (s, 2H), 4.13-4.02 (m, 2H), 3.89-3.84 (m, 1H), 3.05 (d, J=4.8 Hz, 2H), 2.11 (s, 3H); MS (ES) m/z: 545 (M−H+).

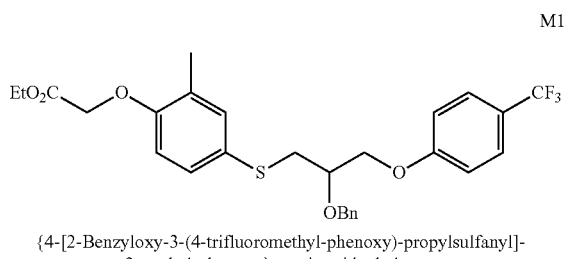

M18

{4-[2-Benzyloxy-3-(4-trifluoromethyl-phenoxy)-propylsulfanyl]-2-methyl-phenoxy}-acetic acid ethyl ester Following general procedure 4 in Example L gave M18 (78%); 1H NMR (300 MHz, CDCl$_3$) δ 7.50 (d, J=8.6 Hz, 2H), 7.31-7.25 (m, 5H), 7.19 (d, J=1.8 Hz, 1H), 7.14 (dd, J=8.4, 2.2 Hz, 1H), 6.89 (d, J=8.6 Hz, 2H), 6.55 (d, J=8.4 Hz, 1H), 4.62 (d, J=4.9 Hz, 2H), 4.57 (s, 2H), 4.25 (q, J=7.1 Hz, 2H), 4.20-4.11 (m, 2H), 3.87 (m, 1H), 3.14 (d, J=6.1 Hz, 2H), 2.21 (s, 3H), 1.29 (t, J=7.1 Hz, 3H); MS (ES) m/z: 557 (M+Na+).

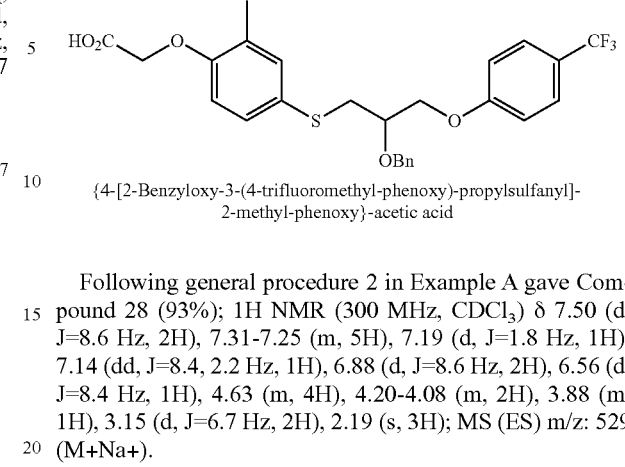

Compound 28

{4-[2-Benzyloxy-3-(4-trifluoromethyl-phenoxy)-propylsulfanyl]-2-methyl-phenoxy}-acetic acid Following general procedure 2 in Example A gave Compound 28 (93%); 1H NMR (300 MHz, CDCl$_3$) δ 7.50 (d, J=8.6 Hz, 2H), 7.31-7.25 (m, 5H), 7.19 (d, J=1.8 Hz, 1H), 7.14 (dd, J=8.4, 2.2 Hz, 1H), 6.88 (d, J=8.6 Hz, 2H), 6.56 (d, J=8.4 Hz, 1H), 4.63 (m, 4H), 4.20-4.08 (m, 2H), 3.88 (m, 1H), 3.15 (d, J=6.7 Hz, 2H), 2.19 (s, 3H); MS (ES) m/z: 529 (M+Na+).

Example N

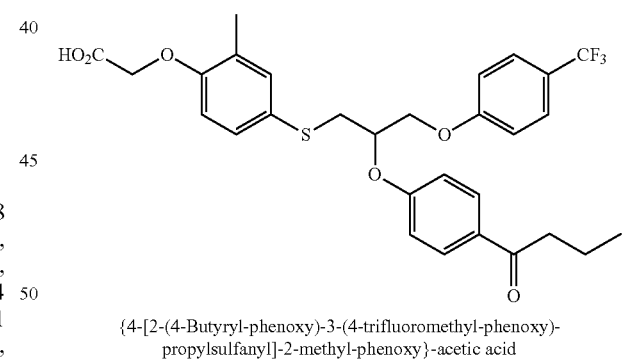

Compound 29

{4-[2-(4-Methoxy-phenoxy)-3-(4-trifluoromethyl-phenoxy)-propylsulfanyl]-2-methyl-phenoxy}-acetic acid Compound 30

{4-[2-(4-Butyryl-phenoxy)-3-(4-trifluoromethyl-phenoxy)-propylsulfanyl]-2-methyl-phenoxy}-acetic acid Scheme N

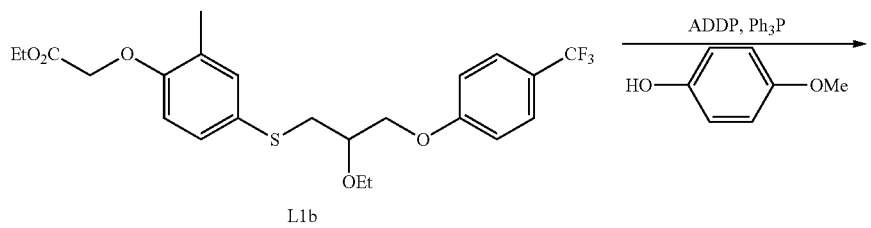

L1b

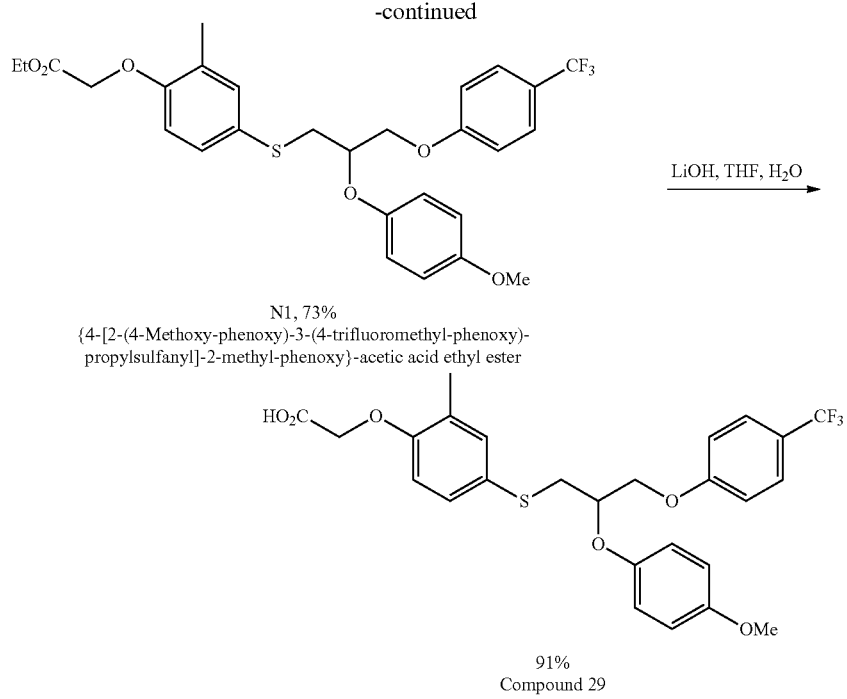

N1, 73%
{4-[2-(4-Methoxy-phenoxy)-3-(4-trifluoromethyl-phenoxy)-propylsulfanyl]-2-methyl-phenoxy}-acetic acid ethyl ester 91%
Compound 29

To a mixture of L1b (122 mg, 0.275 mmol) and 4-methoxyphenol (51 mg, 0.41 mmol) in CH$_2$Cl$_2$ (3 mL) at 0° C. were slowly added 1,1'-(azodicarbonyl)dipiperidine (104 mg, 0.412 mmol) followed by a solution of triphenylphosphine (108 mg, 0.412 mmol) in CH$_2$Cl$_2$ (3 mL). The reaction mixture was allowed to warm up to room temperature, stirred at the same temperature overnight, and filtered. The filtration was concentrated and column chromatographed (EtOAc/hexane:1/7) to provide 110 mg (73%) of N1; MS (ES) m/z: 573 (M+Na+). Following general procedure 2 in Example A gave Compound 29 (91%); MS (ES) m/z: 545 (M+Na+).

N2

{4-[2-Butyryl-phenoxy-3-(4-trifluoromethyl-phenoxy)-propylsulfanyl]-2-methyl-phenoxy}-acetic acid ethyl ester To a mixture of L1b (105 mg, 0.236 mmol) and 1-(4-hydroxyphenyl)-butan-1-one (59 mg, 0.36 mmol) in CH$_2$Cl$_2$ (3 mL) at 0° C. were slowly added 1,1'-(azodicarbonyl)dipiperidine (91 mg, 0.36 mmol) followed by a solution of triphenylphosphine (94 mg, 0.36 mmol) in CH$_2$Cl$_2$ (3 mL). The reaction mixture was allowed to warm up to room temperature, stirred at the same temperature overnight, and filtered. The filtration was concentrated and column chromatographed (EtOAc/hexane:1/7) to provide 95 mg (68%) of N2; MS (ES) m/z: 613 (M+Na+). Following general procedure 2 in Example A gave Compound 30 (95%); MS (ES) m/z: 585 (M+Na+).

Example O

Compound 32

{3-Chloro-4-[2-ethoxy-3-(4-trifluoromethyl-phenoxy)-propylsulfanyl]-phenyl}-acetic acid Scheme O

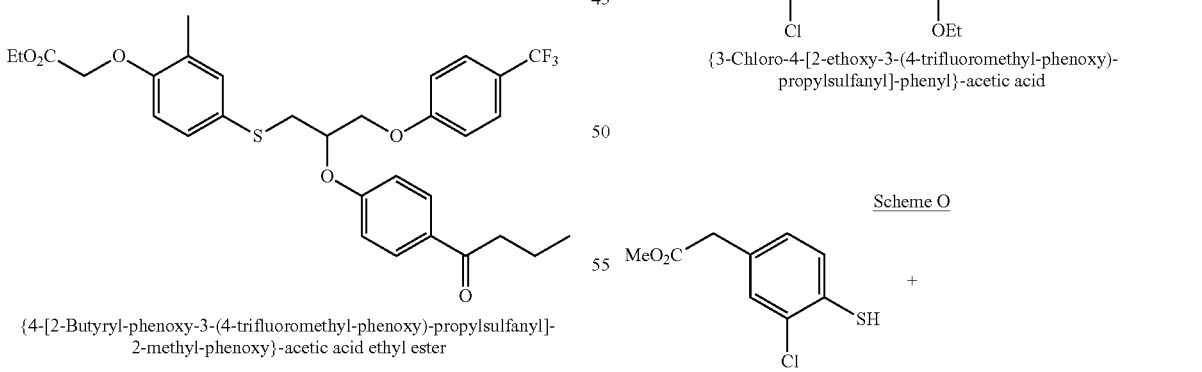

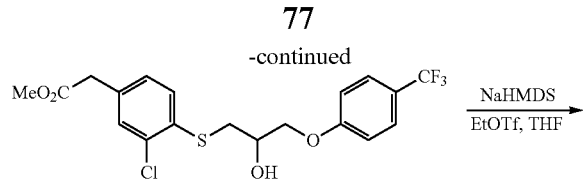

O1, 77%
{3-Chloro-4-[2-hydroxy-3-(4-trifluoromethyl-phenoxy)-propylsulfanyl]phenyl}-acetic acid methyl ester

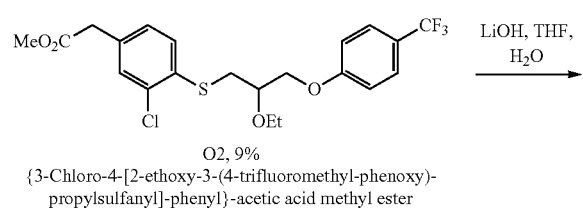

O2, 9%
{3-Chloro-4-[2-ethoxy-3-(4-trifluoromethyl-phenoxy)-propylsulfanyl]-phenyl}-acetic acid methyl ester

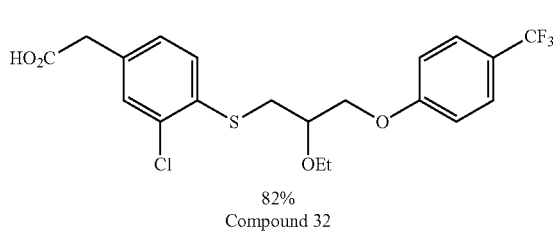

82%
Compound 32

To a mixture of L1a (171 mg, 0.784 mmol) and (3-chloro-4-mercaptophenyl)acetic acid methyl ester H1 (170 mg, 0.787 mmol; WO99/32465) in THF (3 mL) was added 1.0 M tetrabutylammonium fluoride in THF (0.12 mL, 0.12 mmol). The reaction mixture was stirred at room temperature overnight, concentrated, and purified by column chromatography (EtOAc/hexane: ⅓) to give 261 mg (77%) of O1; 1H NMR (400 MHz, CDCl₃) δ 7.53 (d, J=8.8 Hz, 2H), 7.38 (dd, J=8.1 Hz, 1H), 7.32 (d, J=1.7 Hz, 1H), 7.12 (dd, J=8.1, 1.8 Hz, 1H), 6.94 (d, J=8.8 Hz, 2H), 4.15-4.09 (m, 3H), 3.70 (s, 3H), 3.55 (s, 2H), 3.27 (dd, J=13.8, 5.4 Hz, 1H), 3.16 (dd, J=13.7, 6.5 Hz, 1H), 2.75 (brs, 1H); MS (ES) m/z: 457 (M+Na+). Anal. Calcd for C₁₉H₁₈ClF₃O₄S: C, 52.48; H, 4.17. Found: C, 52.50; H, 4.27.

A solution of O1 (368 mg, 0.848 mmol) in THF (2.4 mL) was treated with 1.0 M NaHMDS in THF (0.85 mL, 0.85 mmol) at −78° C. for 15 min. To the mixture was added EtOTf (151 mg, 0.849 mmol) and the cooling bath was removed. The mixture was stirred at room temperature for 1 h, diluted with saturated NaHCO₃, and extracted with Et₂O. The extracts were dried, concentrated, and column chromatographed (EtOAc/hexane) to give 37 mg (9%) of O2; 1H NMR (300 MHz, CDCl₃) δ 7.52 (d, J=8.8 Hz, 2H), 7.36 (dd, J=8.1 Hz, 1H), 7.29 (d, J=1.8 Hz, 1H), 7.10 (dd, J=8.1, 1.8 Hz, 1H), 6.95 (d, J=8.7 Hz, 2H), 4.14 (dd, J=4.9, 1.4 Hz, 2H), 3.85 (m, 1H), 3.70 (s, 3H), 3.66 (q, J=7.0 Hz, 2H), 3.54 (s, 2H), 3.28 (dd, J=13.6, 6.2 Hz, 1H), 3.19 (dd, J=13.6, 5.8 Hz, 1H), 1.20 (t, J=7.0 Hz, 3H); MS (ES) m/z: 485 (M+Na+).

Following general procedure 2 in Example A gave Compound 32 (82%); 1H NMR (400 MHz, MeOH-d4) δ 7.56 (d, J=8.6 Hz, 2H), 7.45 (d, J=8.1 Hz, 1H), 7.32 (d, J=1.3 Hz, 1H), 7.16 (dd, J=8.1, 1.4 Hz, 1H), 7.04 (d, J=8.6 Hz, 2H), 4.22-4.14 (m, 2H), 3.86 (m, 1H), 3.65 (q, J=7.0 Hz, 2H), 3.55 (s, 2H), 3.30-3.28 (m, 1H), 3.22 (dd, J=13.8, 6.1 Hz, 1H), 1.15 (t, J=7.0 Hz, 3H); MS (ES) m/z: 471 (M+Na+).

Example P

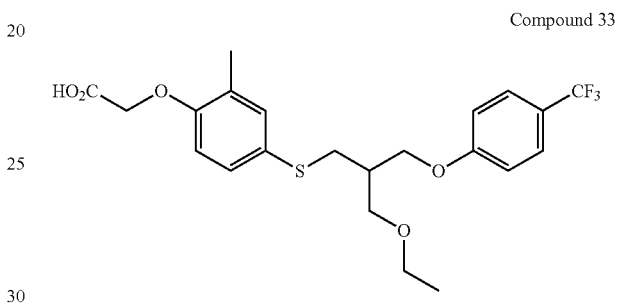

Compound 33

{4-[2-Ethoxymethyl-3-(4-trifluoromethyl-phenoxy)-propylsulfanyl]-2-methyl-phenoxy}-acetic acid

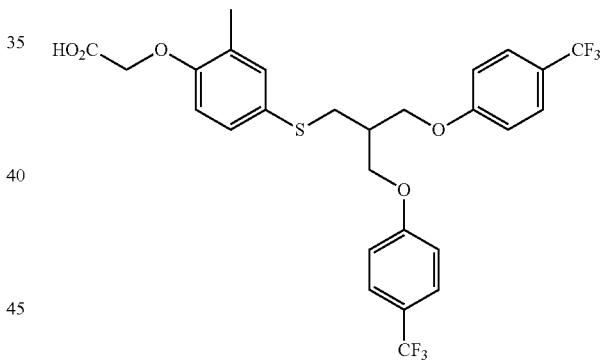

Compound 34

{2-Methyl-4-[3-(4-trifluoromethyl-phenoxy)-2-(4-trifluoromethyl-phenoxymethyl)-propylsulfanyl]-phenoxy}-acetic acid Scheme P

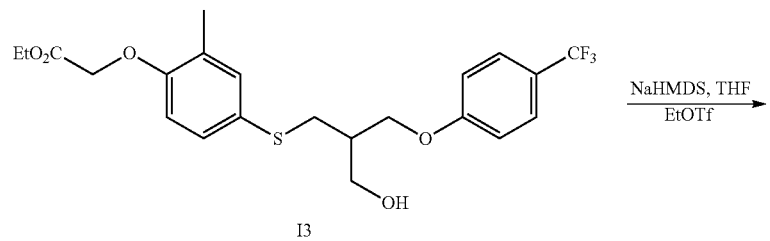

I3

-continued

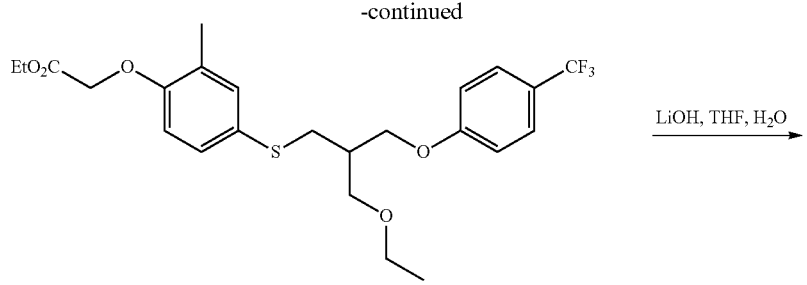

P1, 47%
{4-[2-Ethoxymethyl-3-(4-trifluoromethyl-phenoxy)-propylsulfanyl]-2-methyl-phenoxy}-acetic acid ethyl ester

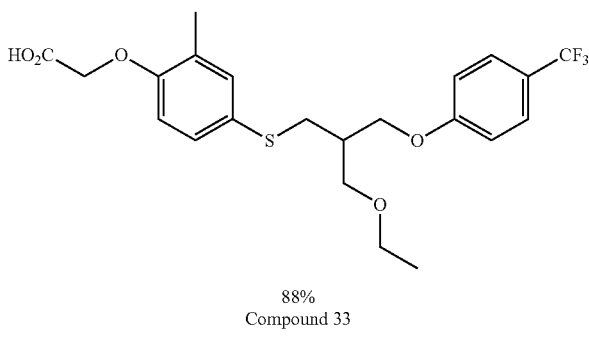

88%
Compound 33

To a solution of I3 (126 mg, 0.275 mmol) in THF (2 mL) at −78° C. was added 1.0 M sodium bis(trimethylsilyl)amide (0.27 mL, 0.27 mmol) in THF. After stirring for 5 min, ethyl trifluoromethanesulfonate (48 mg, 0.27 mmol) was introduced and the cooling bath was removed. The mixture was stirred for 30 min, quenched with saturated NaHCO$_3$, and extracted with Et$_2$O (×3). The extracts were dried, concentrated, and purified by column chromatography (EtOAc/hexane: 1/7) to provide 62 mg (47%) of P1; 1H NMR (300 MHz, CDCl$_3$) δ 7.51 (d, J=8.6 Hz, 2H), 7.21 (d, J=2.2 Hz, 1H), 7.16 (dd, J=8.4, 2.2 Hz, 1H), 6.91 (d, J=8.6 Hz, 2H), 6.58 (d, J=8.4 Hz, 1H), 4.57 (s, 2H), 4.25 (q, J=7.1 Hz, 2H), 4.12 (dd, J=9.3, 5.4 Hz, 1H), 4.06 (dd, J=9.3, 5.4 Hz, 1H), 3.58-3.55 (m, 2H), 3.44 (q, J=7.0 Hz, 2H), 3.04 (d, J=6.7 Hz, 2H), 2.29 (m, 1H), 2.23 (s, 3H), 1.29 (t, J=7.1 Hz, 3H), 1.16 (t, J=7.0 Hz, 3H); MS (ES) m/z: 509 (M+Na+).

Following general procedure 2 in Example A gave Compound 33 (88%); 1H NMR (300 MHz, CDCl$_3$) δ 7.50 (d, J=8.6 Hz, 2H), 7.17 (s, 1H), 7.14 (d, J=8.3, 1H), 6.90 (d, J=8.6 Hz, 2H), 6.57 (d, J=8.3 Hz, 1H), 4.50 (s, 2H), 4.11 (dd, J=9.3, 5.4 Hz, 1H), 4.04 (dd, J=9.3, 5.4 Hz, 1H), 3.57-3.54 (m, 2H), 3.44 (q, J=7.0 Hz, 2H), 3.02 (d, J=6.7 Hz, 2H), 2.27 (m, 1H), 2.17 (s, 3H), 1.15 (t, J=7.0 Hz, 3H); MS (ES) m/z: 481 (M+Na+). Anal. Calcd for C$_{22}$H$_{25}$F$_3$O$_5$S: C, 57.63; H, 5.50. Found: C, 57.77; H, 5.42.

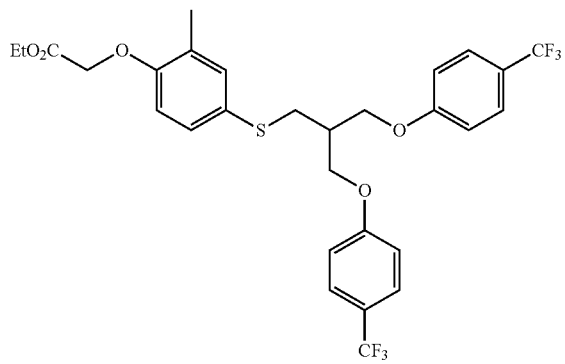 [SMILES: Cc1cc(SCC(COc2ccc(C(F)(F)F)cc2)COc2ccc(C(F)(F)F)cc2)ccc1OCC(=O)O]

P2
{2-Methyl-4-[3-(4-trifluoromethyl-phenoxy)-2-(4-trifluoromethyl-phenoxymethyl)-propylsulfanyl]-phenoxy}-acetic acid ethyl ester To a mixture of I3 (104 mg, 0.227 mmol), trifluoromethylphenol (56 mg, 0.35 mmol), and triphenylphosphine (91 mg, 0.35 mmol) in THF (3 mL) at 0° C. was added diisopropyl azodicarboxylate (70 mg, 0.35 mmol). The mixture was stirred at 0° C. for 30 min and room temperature for 7 h, concentrated, and column chromatographed (EtOAc/hexane: 1/8) to provide 110 mg (79%) of P2; 1H NMR (300 MHz, CDCl$_3$) δ 7.52 (d, J=8.6 Hz, 4H), 7.22 (d, J=1.8 Hz, 1H), 7.17 (dd, J=8.4, 2.3 Hz, 1H), 6.92 (d, J=8.6 Hz, 4H), 6.56 (d, J=8.4 Hz, 1H), 4.57 (s, 2H), 4.26 (q, J=7.1 Hz, 2H), 4.21-4.16 (m, 4H), 3.14 (d, J=6.7 Hz, 2H), 2.54 (m, 1H), 2.21 (s, 3H), 1.29 (t, J=7.1 Hz, 3H); MS (ES) m/z: 625 (M+Na+). Anal. Calcd for C$_{29}$H$_{28}$F$_6$O$_5$S: C, 57.80; H, 4.68. Found: C, 57.92; H, 4.52.

Compound 34

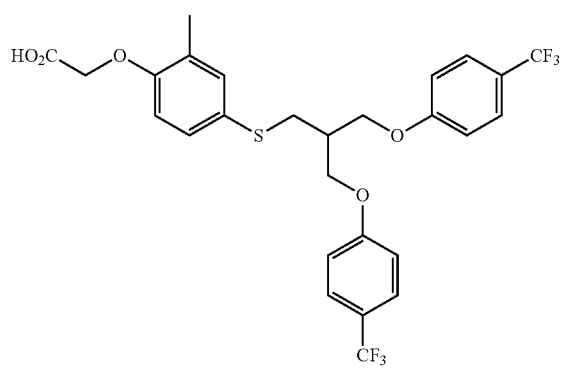

{2-Methyl-4-[3-(4-trifluoromethyl-phenoxy)-2-(4-trifluoromethyl-phenoxymethyl)-propylsulfanyl]-phenoxy}-acetic acid Following general procedure 2 in Example A gave Compound 34 (84%); 1H NMR (300 MHz, MeOH-d4) δ 7.54 (d, J=8.1 Hz, 4H), 7.22 (m, 2H), 7.01 (d, J=8.1 Hz, 4H), 6.66 (d, J=8.1 Hz, 1H), 4.56 (s, 2H), 4.22 (m, 4H), 3.16 (d, J=6.2 Hz, 2H), 2.50 (m, 1H), 2.14 (s, 3H); MS (ES) m/z: 597 (M+Na+). Anal. Calcd for $C_{27}H_{24}F_6O_5S$: C, 56.44; H, 4.21. Found: C, 56.08; H, 4.01.

Example Q

Compound 35

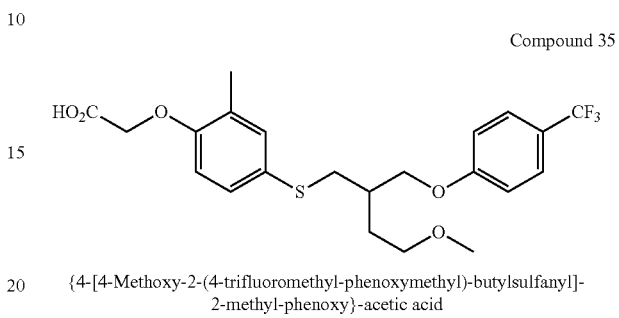

{4-[4-Methoxy-2-(4-trifluoromethyl-phenoxymethyl)-butylsulfanyl]-2-methyl-phenoxy}-acetic acid Scheme Q

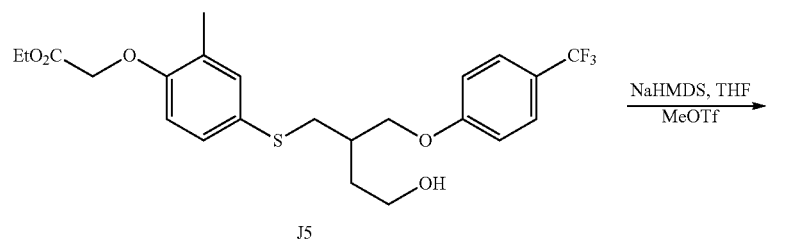

J5

NaHMDS, THF
MeOTf
⟶

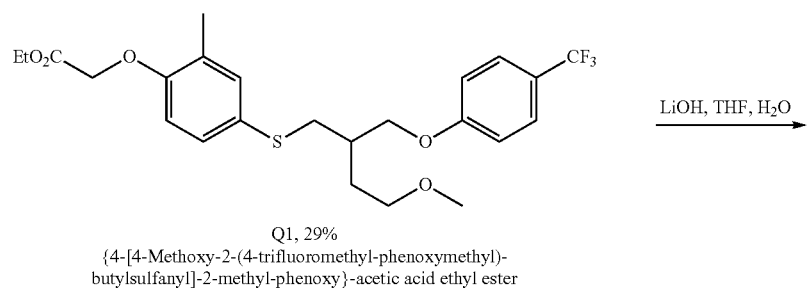

Q1, 29%
{4-[4-Methoxy-2-(4-trifluoromethyl-phenoxymethyl)-butylsulfanyl]-2-methyl-phenoxy}-acetic acid ethyl ester LiOH, THF, H₂O
⟶

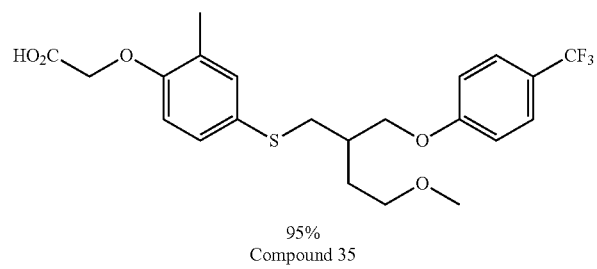

95%
Compound 35

To a solution of J5 (117 mg, 0.248 mmol) in THF (2 mL) at −78° C. was added 1.0 M sodium bis(trimethylsilyl)amide (0.25 mL, 0.25 mmol) in THF. After stirring for 5 min, methyl trifluoromethanesulfonate (41 mg, 0.25 mmol) was introduced and the cooling bath was removed. After the temperature rising to room temperature, the mixture was quenched with water and extracted with Et$_2$O (×3). The extracts were dried, concentrated, and purified by column chromatography (EtOAc/hexane: ⅙) to provide 35 mg (29%) of Q1; 1H NMR (300 MHz, CDCl$_3$) δ 7.51 (d, J=8.6 Hz, 2H), 7.19 (d, J=1.6 Hz, 1H), 7.14 (dd, J=8.4, 2.1 Hz, 1H), 6.89 (d, J=8.6 Hz, 2H), 6.55 (d, J=8.4 Hz, 1H), 4.56 (s, 2H), 4.25 (q, J=7.1 Hz, 2H), 4.08 (dd, J=9.3, 4.7 Hz, 1H), 3.99 (dd, J=9.3, 5.5 Hz, 1H), 3.45 (t, J=6.3 Hz, 2H), 3.31 (s, 3H), 3.04 (d, J=6.2 Hz, 2H), 2.26-2.18 (m, 1H), 2.21 (s, 3H), 1.82 (q, J=6.4 Hz, 2H), 1.29 (t, J=7.1 Hz, 3H); MS (ES) m/z: 509 (M+Na+).

Following general procedure 2 in Example A gave Compound 35 (95%); 1H NMR (300 MHz, CDCl$_3$) δ 7.49 (d, J=8.6 Hz, 2H), 7.19-7.12 (m, 2H), 6.87 (d, J=8.6 Hz, 2H), 6.55 (m, 1H), 4.51 (s, 2H), 4.07 (m, 1H), 3.97 (m, 1H), 3.45 (t, J=6.0 Hz, 2H), 3.30 (s, 3H), 3.03 (d, J=6.2 Hz, 2H), 2.21-2.17 (m, 1H), 2.17 (s, 3H), 1.82 (q, J=6.3 Hz, 2H); MS (ES) m/z: 481 (M+Na+).

Compound 36

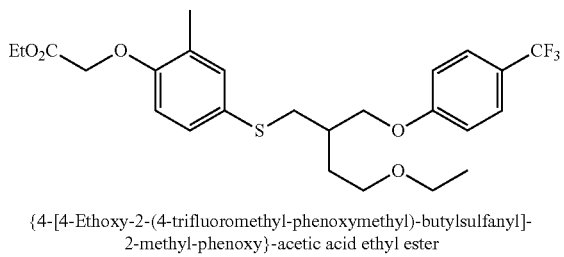

{4-[4,4-Diethoxy-2-(4-trifluoromethyl-phenoxymethyl)-butylsulfanyl]-2-methyl-phenoxy}-acetic acid Using J3 as the starting material and following general procedure 2 in Example A gave Compound 36 (85%); 1H NMR (300 MHz, CDCl$_3$) δ 7.49 (d, J=8.6 Hz, 2H), 7.17 (s, 1H), 7.14 (d, J=8.7 Hz, 1H), 6.87 (d, J=8.6 Hz, 2H), 6.55 (d, J=7.9 Hz, 1H), 4.60 (t, J=5.6 Hz, 1H), 4.54 (s, 2H), 4.10 (dd, J=9.3, 4.5 Hz, 1H), 3.99 (dd, J=9.3, 5.7 Hz, 1H), 3.68-3.56 (m, 2H), 3.51-3.40 (m, 2H), 3.05-3.00 (m, 2H), 2.25-2.17 (m, 1H), 2.17 (s, 3H), 1.89-1.84 (m, 2H), 1.16 (t, J=7.0 Hz, 3H), 1.15 (t, J=7.0 Hz, 3H); MS (ES) m/z: 539 (M+Na+).

Q2

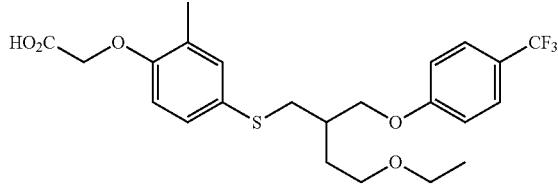 [SMILES: CCOCCC(COc1ccc(C(F)(F)F)cc1)CSc1ccc(OCC(=O)O)c(C)c1]

{4-[4-Ethoxy-2-(4-trifluoromethyl-phenoxymethyl)-butylsulfanyl]-2-methyl-phenoxy}-acetic acid ethyl ester Replacing methyl trifluoromethanesulfonate with ethyl trifluoromethanesulfonate and following the same procedure as in the preparation of Q1 provided the title compound Q2 (23%); 1H NMR (300 MHz, CDCl$_3$) δ 7.50 (d, J=8.6 Hz, 2H), 7.19 (d, J=1.7 Hz, 1H), 7.14 (dd, J=8.4, 2.2 Hz, 1H), 6.88 (d, J=8.6 Hz, 2H), 6.55 (d, J=8.4 Hz, 1H), 4.56 (s, 2H), 4.25 (q, J=7.1 Hz, 2H), 4.10 (dd, J=9.3, 4.6 Hz, 1H), 4.00 (dd, J=9.3, 5.6 Hz, 1H), 3.51-3.40 (m, 4H), 3.04 (d, J=6.1 Hz, 2H), 2.27-2.21 (m, 1H), 2.21 (s, 3H), 1.82 (q, J=6.5 Hz, 2H), 1.29 (t, J=7.1 Hz, 3H), 1.16 (t, J=7.0 Hz, 3H); MS (ES) m/z: 523 (M+Na+).

Compound 37

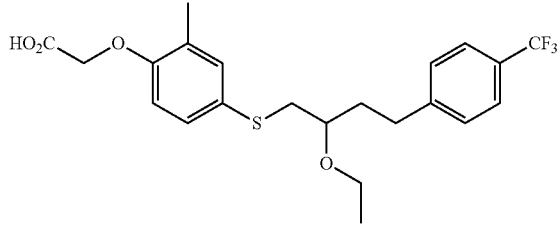 [SMILES: CCOC(COc1ccc(C(F)(F)F)cc1)CSc1ccc(OCC(=O)O)c(C)c1]

{4-[4-Ethoxy-2-(4-trifluoromethyl-phenoxymethyl)-butylsulfanyl]-2-methyl-phenoxy}-acetic acid Following general procedure 2 in Example A gave Compound 37 (92%); 1H NMR (300 MHz, MeOH-d4) δ 7.53 (d, J=8.6 Hz, 2H), 7.17 (m, 1H), 7.14 (d, J=2.1 Hz, 1H), 6.98 (d, J=8.6 Hz, 2H), 6.66 (d, J=8.2 Hz, 1H), 4.41 (s, 2H), 4.12 (dd, J=9.5, 4.8 Hz, 1H), 4.03 (dd, J=9.5, 5.5 Hz, 1H), 3.52-3.40 (m, 4H), 3.00 (d, J=6.4 Hz, 2H), 2.17 (s, 3H), 2.17-2.11 (m, 1H), 1.83-1.76 (m, 2H), 1.13 (t, J=7.0 Hz, 3H); MS (ES) m/z: 495 (M+Na+).

Example R

Compound 38

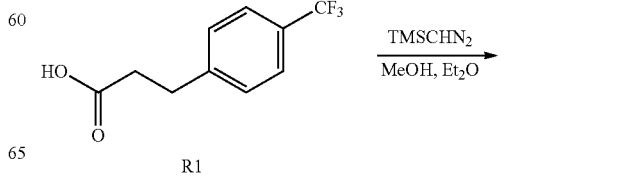

{4-[2-Ethoxy-4-(4-trifluoromethyl-phenyl)-butylsulfanyl]-2-methyl-phenoxy}-acetic acid Scheme R HO$\underset{O}{\overset{}{\bigcirc}}$ —CF$_3$ structure with TMSCHN$_2$, MeOH, Et$_2$O

R1

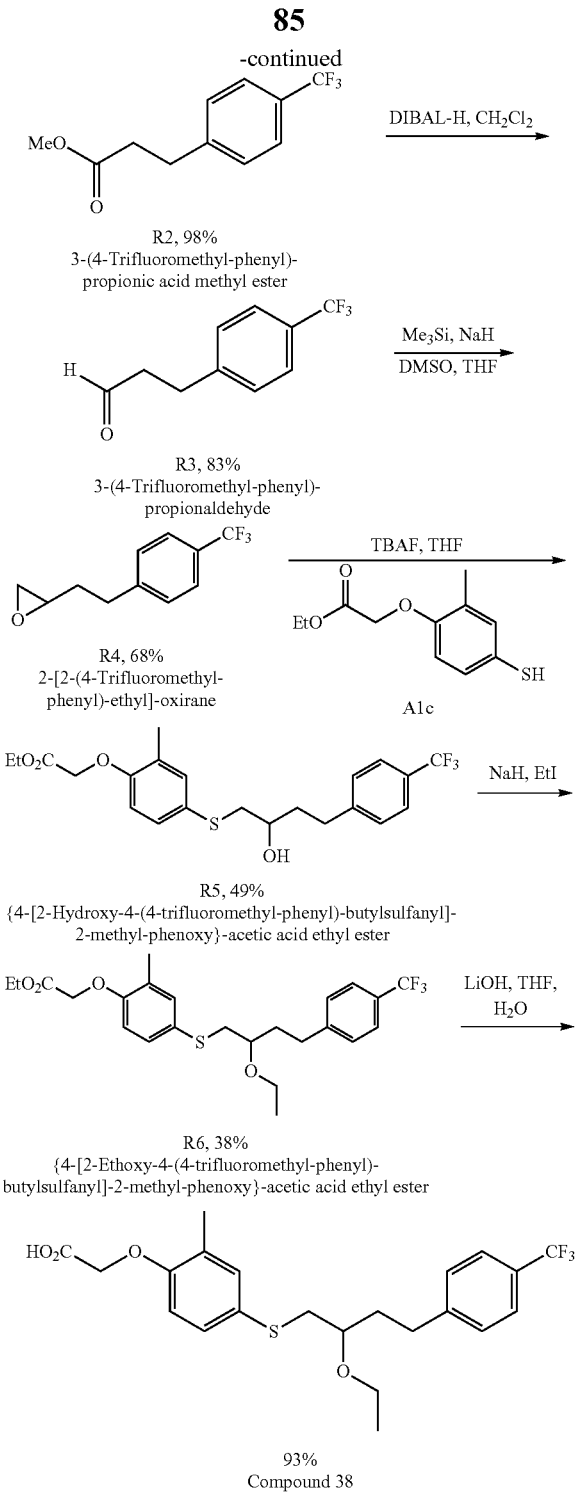

-continued

R2, 98%
3-(4-Trifluoromethyl-phenyl)-propionic acid methyl ester

R3, 83%
3-(4-Trifluoromethyl-phenyl)-propionaldehyde

R4, 68%
2-[2-(4-Trifluoromethyl-phenyl)-ethyl]-oxirane

A1c

R5, 49%
{4-[2-Hydroxy-4-(4-trifluoromethyl-phenyl)-butylsulfanyl]-2-methyl-phenoxy}-acetic acid ethyl ester R6, 38%
{4-[2-Ethoxy-4-(4-trifluoromethyl-phenyl)-butylsulfanyl]-2-methyl-phenoxy}-acetic acid ethyl ester 93%
Compound 38

To a solution of R1 (1.00 g, 4.59 mmol) in Et$_2$O (20 mL) and MeOH (10 mL) was added 1.0 M (trimethylsilyl) diazomethane (9.16 mL, 9.16 mmol) in hexane. After stirring at room temperature for 1 h, the solvents were removed under reduced pressure. The residue was dissolved in Et$_2$O, washed with saturated NaHCO$_3$ and brine, dried, and concentrated to give 1.04 g (98%) of R2; 1H NMR (300 MHz, CDCl$_3$) δ 7.54 (d, J=8.1 Hz, 2H), 7.31 (d, J=8.1 Hz, 2H), 3.67 (s, 3H), 3.01 (t, J=7.7 Hz, 2H), 2.65 (t, J=7.7 Hz, 2H); MS (ES) m/z: 255 (M+Na+).

To a solution of R2 (1.10 g, 4.74 mmol) in CH$_2$Cl$_2$ (20 mL) at −78° C. was added 1.0 M diisobutylaluminum hydride (4.74 mL, 4.74 mmol). The mixture was stirred at −78° C. for 10 min and quenched with 10% HCl in MeOH (5 mL). After warming to room temperature, the mixture was filtered and the filtrate was concentrated and column chromatographed to provide 796 mg (83%) of R3; 1H NMR (400 MHz, CDCl$_3$) δ 9.82 (d, J=1.0 Hz, 1H), 7.54 (d, J=8.1 Hz, 2H), 7.31 (d, J=8.0 Hz, 2H), 3.01 (t, J=7.4 Hz, 2H), 2.82 (t, J=7.3 Hz, 2H).

A mixture of NaH (52 mg, 1.3 mmol; 60% in mineral oil) in DMSO (15 mL) was heated at 70° C. for 30 min and allowed to cool to room temperature. After diluting with THF (10 mL), to the mixture at 0° C. was slowly added a solution of trimethylsulfonium iodide (306 mg, 1.50 mmol) in DMSO (10 mL). After stirring for 10 min at 0° C., a solution of R3 (202 mg, 1.00 mmol) in THF (10 mL) was introduced. Stirring was continued for 1 h at 0° C. and the mixture was diluted with water and extracted with Et$_2$O. The extracts were dried, concentrated, and column chromatographed (EtOAc/hexane: 1/7) to provide 147 mg (68%) of R4; 1H NMR (300 MHz, CDCl$_3$) δ 7.54 (d, J=8.1 Hz, 2H), 7.31 (d, J=8.0 Hz, 2H), 2.97-2.90 (m, 1H), 2.88-2.78 (m, 2H), 2.75 (m, 1H), 2.47 (dd, J=4.9, 2.7 Hz, 1H), 1.98-1.73 (m, 2H).

A mixture of R4 (251 mg, 1.16 mmol), (4-mercapto-2-methylphenoxy)acetic acid ethyl ester A1c (394 mg, 1.74 mmol), and tetrabutylammonium fluoride (0.12 mL, 0.12 mmol; 1.0 M in THF) in THF (5 mL) was stirred at room temperature overnight and concentrated. The residue was purified by column chromatography (EtOAc/hexane: 1/5) to give 250 mg (49%) of R5; 1H NMR (300 MHz, CDCl$_3$) δ 7.51 (d, J=8.0 Hz, 2H), 7.26 (d, J=8.0 Hz, 2H), 7.23 (d, J=2.1 Hz, 1H), 7.18 (dd, J=8.4, 2.3 Hz, 1H), 6.61 (d, J=8.4 Hz, 1H), 4.62 (s, 2H), 4.26 (q, J=7.1 Hz, 2H), 3.63-3.55 (m, 1H), 3.01 (dd, J=13.6, 3.4 Hz, 1H), 2.91-2.81 (m, 1H), 2.79-2.66 (m, 2H), 2.56 (brs, 1H), 2.25 (s, 3H), 1.84-1.76 (m, 2H), 1.30 (t, J=7.1 Hz, 3H); MS (ES) m/z: 465 (M+Na+).

A solution of R5 (44 mg, 0.10 mmol) in THF (0.5 mL) was treated with NaH (4.4 mg, 0.11 mmol; 60% in mineral oil) for 30 min and EtI (86 mg, 0.55 mmol) was introduced. After stirring overnight, the mixture was diluted with water and extracted with Et$_2$O. The extracts were dried, concentrated, and purified by column chromatography (EtOAc/hexane) to give 18 mg (38%) of R6; 1H NMR (300 MHz, CDCl$_3$) δ 7.52 (d, J=8.1 Hz, 2H), 7.27 (d, J=8.1 Hz, 2H), 7.19 (d, J=1.8 Hz, 1H), 7.11 (dd, J=8.4, 2.2 Hz, 1H), 6.59 (d, J=8.4 Hz, 1H), 4.61 (s, 2H), 4.26 (q, J=7.1 Hz, 2H), 3.58-3.50 (m, 1H), 3.40-3.31 (m, 2H), 3.06 (dd, J=13.3, 4.8 Hz, 1H), 2.85 (dd, J=13.3, 7.3 Hz, 1H), 2.79-2.64 (m, 2H), 2.25 (s, 3H), 2.06-1.96 (m, 1H), 1.92-1.79 (m, 1H), 1.29 (t, J=7.1 Hz, 3H), 1.17 (t, J=7.0 Hz, 3H); MS (ES) m/z: 493 (M+Na+).

Compound 38

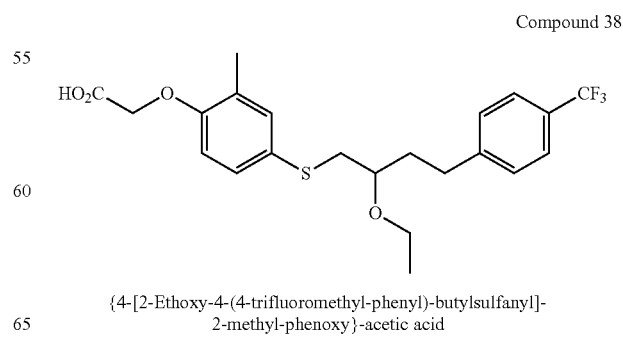

{4-[2-Ethoxy-4-(4-trifluoromethyl-phenyl)-butylsulfanyl]-2-methyl-phenoxy}-acetic acid Following general procedure 2 in Example A gave Compound 38 (93%); 1H NMR (300 MHz, CDCl₃) δ 9.25 (brs, 1H), 7.51 (d, J=8.0 Hz, 2H), 7.25 (d, J=8.0 Hz, 2H), 7.17 (d, J=1.5 Hz, 1H), 7.09 (dd, J=8.4, 2.0 Hz, 1H), 6.58 (d, J=8.5 Hz, 1H), 4.56 (s, 2H), 3.61-3.51 (m, 1H), 3.42-3.31 (m, 2H), 3.05 (dd, J=13.2, 4.9 Hz, 1H), 2.84 (dd, J=13.2, 7.1 Hz, 1H), 2.80-2.63 (m, 2H), 2.20 (s, 3H), 2.05-1.94 (m, 1H), 1.92-1.81 (m, 1H), 1.16 (t, J=7.0 Hz, 3H); MS (ES) m/z: 441 (M−H+).

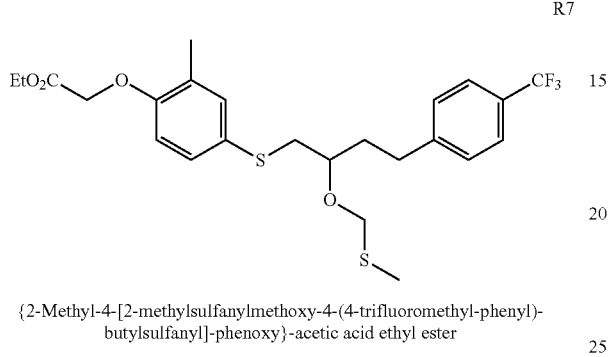

R7

{2-Methyl-4-[2-methylsulfanylmethoxy-4-(4-trifluoromethyl-phenyl)-butylsulfanyl]-phenoxy}-acetic acid ethyl ester A mixture of R5 (370 mg, 0.837 mmol) in Ac₂O (2.5 mL) and DMSO (4 mL) was stirred at room temperature for 24 h, diluted with water, and extracted with Et₂O. The extracts were dried, concentrated, and purified by column chromatography to give 51 mg (12%) of the title compound R7; 1H NMR (300 MHz, CDCl₃) δ 7.52 (d, J=8.1 Hz, 2H), 7.27 (d, J=8.2 Hz, 2H), 7.22 (d, J=1.6 Hz, 1H), 7.14 (dd, J=8.4, 2.1 Hz, 1H), 6.61 (d, J=8.5 Hz, 1H), 4.67-4.58 (m, 2H), 4.61 (s, 2H), 4.25 (q, J=7.1 Hz, 2H), 3.78 (m, 1H), 3.10 (dd, J=13.4, 4.9 Hz, 1H), 2.91 (dd, J=13.4, 6.9 Hz, 1H), 2.84-2.64 (m, 2H), 2.26 (s, 3H), 2.17 (s, 3H), 2.09-1.86 (m, 2H), 1.29 (t, J=7.1 Hz, 3H); MS (ES) m/z: 525 (M+Na+).

Compound 39

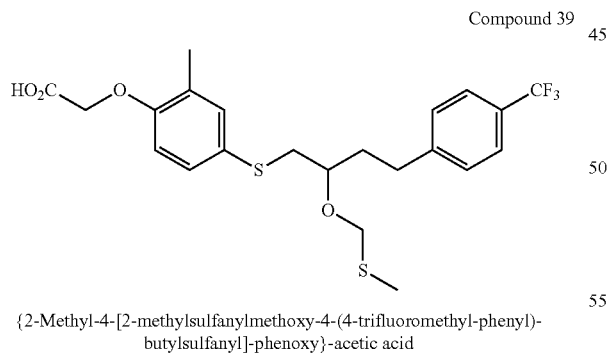

{2-Methyl-4-[2-methylsulfanylmethoxy-4-(4-trifluoromethyl-phenyl)-butylsulfanyl]-phenoxy}-acetic acid Following general procedure 2 in Example A gave Compound 39 (90%); 1H NMR (300 MHz, CDCl₃) δ 7.48 (d, J=7.9 Hz, 2H), 7.23 (d, J=7.8 Hz, 2H), 7.04 (m, 2H), 6.46 (m, 1H), 4.57 (s, 2H), 4.53 (s, 2H), 3.76 (m, 1H), 2.98 (m, 1H), 2.88 (m, 1H), 2.80-2.63 (m, 2H), 2.11 (s, 3H), 2.06 (s, 3H), 1.89 (m, 2H); MS (ES) m/z: 473 (M−H+).

Example S

Compound 42

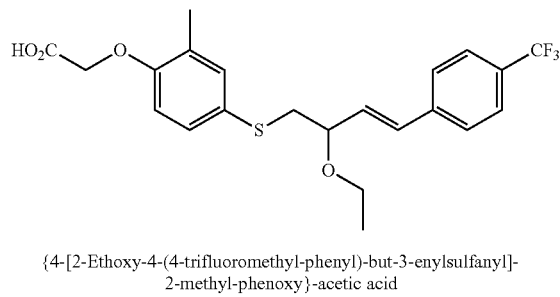

{4-[2-Ethoxy-4-(4-trifluoromethyl-phenyl)-but-3-enylsulfanyl]-2-methyl-phenoxy}-acetic acid Scheme S1

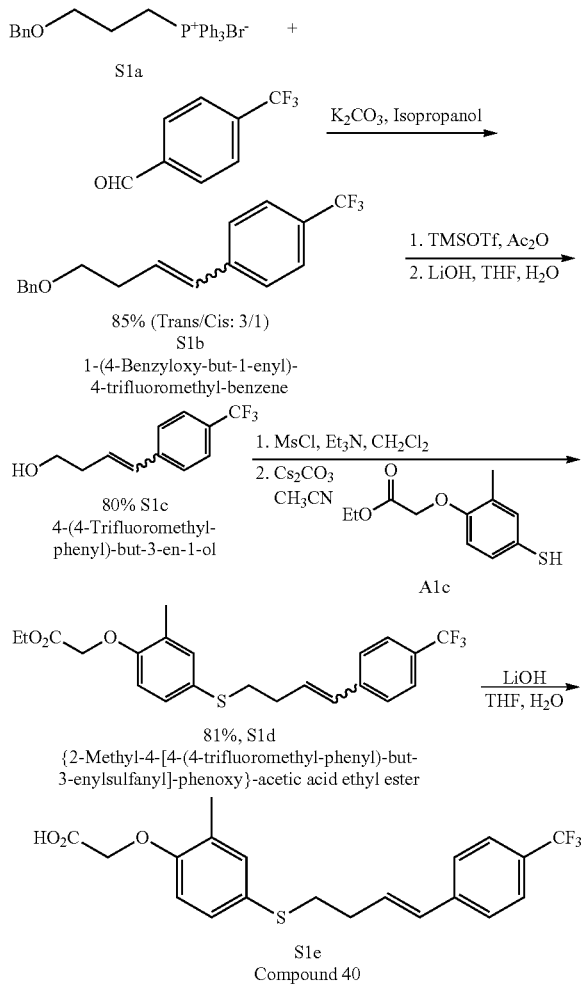

A mixture of (3-benzyloxypropyl)triphenyl-phosphonium bromide S1a (614 mg, 1.25 mmol), 4-trifluoromethylbenzaldehyde (174 mg, 1.00 mmol), and K₂CO₃ (173 mg, 1.25 mmol) in isopropanol (1 mL) was refluxed for 5 h and concentrated. The residue was partitioned between water and Et₂O. The organic phase was dried, concentrated, and column chromatographed (1% EtOAc in hexane) to give 260 mg (85%) of S1b as a mixture of trans and cis in the ratio of 3:1. Trans: 1H NMR (300 MHz, CDCl$_3$) δ 7.53 (d, J=8.2 Hz, 2H), 7.42 (d, J=8.2 Hz, 2H), 7.35-7.27 (m, 5H), 6.49 (d, J=16.0 Hz, 1H), 6.35 (dt, J=15.9, 6.7 Hz, 1H), 4.55 (s, 2H), 3.61 (t, J=6.5 Hz, 2H), 2.55 (m, 2H).

A solution of S1b (50 mg, 0.16 mmol) in Ac$_2$O (0.8 mL) at 0° C. was treated with trimethylsilyl trifluoromethanesulfonate (142 mg, 0.640 mmol) for 15 min, and quenched with saturated NaHCO$_3$. The mixture was extracted with Et$_2$O, and the extracts were dried, concentrated, and column chromatographed to give acetates as a mixture of trans and cis products.

A solution of the trans and cis acetates (390 mg, 1.51 mmol) in THF (10 mL) was treated with 1.0 M LiOH (3 mL, 3.0 mmol) at room temperature overnight and extracted with Et$_2$O. The extracts were dried, concentrated, and column chromatographed to give S1c as a mixture of trans and cis alcohols. Trans: 1H NMR (300 MHz, CDCl$_3$) δ 7.55 (d, J=8.2 Hz, 2H), 7.44 (d, J=8.2 Hz, 2H), 6.53 (d, J=15.9 Hz, 1H), 6.33 (dt, J=15.9, 7.1 Hz, 1H), 3.79 (t, J=6.3 Hz, 2H), 2.54-2.49 (m, 2H); MS (ES) m/z: 239 (M+Na+).

Following general procedure 1 in Example A gave S1d (81%) as pure compound and a mixture of trans and cis. Trans: 1H NMR (300 MHz, CDCl$_3$) δ 7.53 (d, J=8.2 Hz, 2H), 7.39 (d, J=8.2 Hz, 2H), 7.24 (s, 1H), 7.20 (dd, J=8.4, 2.0 Hz, 1H), 6.63 (d, J=8.4 Hz, 1H), 6.43 (d, J=16.0 Hz, 1H), 6.35-6.25 (m, 1H), 4.61 (s, 2H), 4.26 (q, J=7.1 Hz, 2H), 2.96 (t, J=7.3 Hz, 2H), 2.51 (q, J=7.0 Hz, 2H), 2.26 (s, 3H), 1.29 (t, J=7.1 Hz, 3H); MS (ES) m/z: 447 (M+Na+). Anal. Calcd for C$_{22}$H$_{23}$F$_3$O$_3$S: C, 62.26; H, 5.46. Found: C, 62.43; H, 5.33.

Following general procedure 2 in Example A gave S1e Compound 40 (92%); 1H NMR (300 MHz, CDCl$_3$) δ 10.78 (brs, 1H), 7.53 (d, J=8.2 Hz, 2H), 7.39 (d, J=8.1 Hz, 2H), 7.25 (d, J=2.5 Hz, 1H), 7.21 (dd, J=8.4, 2.0 Hz, 1H), 6.66 (d, J=8.4 Hz, 1H), 6.43 (d, J=16.0 Hz, 1H), 6.35-6.25 (m, 1H), 4.67 (s, 2H), 2.97 (m, 2H), 2.52 (q, J=6.9 Hz, 2H), 2.25 (s, 3H); MS (ES) m/z: 419 (M+Na+).

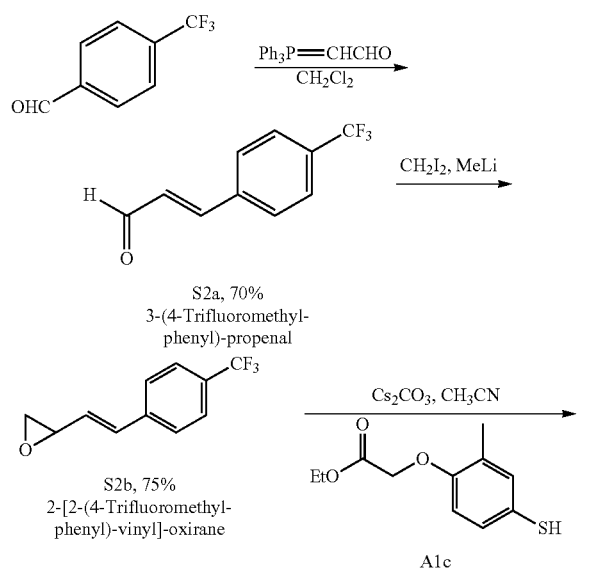

Scheme S2

S2a, 70%
3-(4-Trifluoromethyl-phenyl)-propenal

S2b, 75%
2-[2-(4-Trifluoromethyl-phenyl)-vinyl]-oxirane

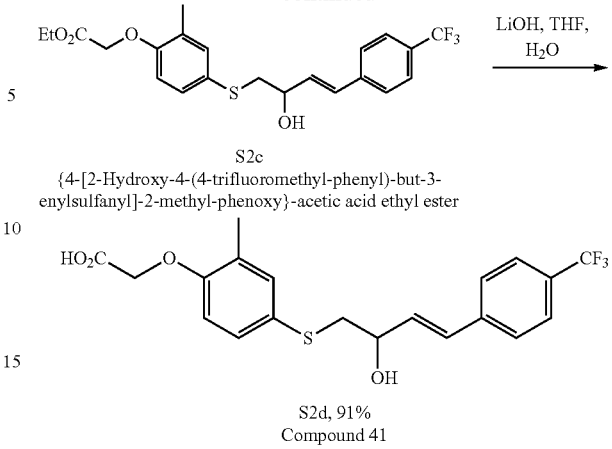

S2c
{4-[2-Hydroxy-4-(4-trifluoromethyl-phenyl)-but-3-enylsulfanyl]-2-methyl-phenoxy}-acetic acid ethyl ester S2d, 91%
Compound 41

A mixture of 4-trifluoromethylbenzaldehyde (174 mg, 1.00 mmol) and (triphenylphosphoranylidene)acetaldehyde (396 mg, 1.30 mmol) in CH$_2$Cl$_2$ (6 mL) was stirred at room temperature for 20 h, concentrated, and column chromatographed (EtOAc/hexane: ⅛) to give 182 mg (70%) of S2a; 1H NMR (400 MHz, CDCl$_3$) δ 9.76 (d, J=7.5 Hz, 1H), 7.69 (m, 4H), 7.51 (d, J=16.0 Hz, 1H), 6.78 (dd, J=16.0, 7.5 Hz, 1H); MS (ES) m/z: 223 (M+Na+).

To a solution of S2a (425 mg, 2.13 mmol) in THF (6 mL) at −78° C. was added CH$_2$I$_2$ (627 mg, 2.34 mmol) followed by 1.5 M MeLi (1.56 mL, 2.34 mmol; complexed with LiBr in Et$_2$O). The mixture was allowed to gradually warm up to room temperature, quenched with saturated NH$_4$Cl, and extracted with Et$_2$O. The extracts were dried, concentrated, and column chromatographed (CH2Cl2/hexane: ⅔) to provide 341 mg (75%) of S2b; 1H NMR (400 MHz, CDCl$_3$) δ 7.58 (d, J=8.2 Hz, 2H), 7.47 (d, J=8.2 Hz, 2H), 6.84 (d, J=16.0 Hz, 1H), 5.99 (dd, J=16.0, 7.8 Hz, 1H), 3.55-3.52 (m, 1H), 3.08 (dd, J=5.1, 4.3 Hz, 1H), 2.79 (dd, J=5.2, 2.6 Hz, 1H); MS (ES) m/z: 213 (M−H+).

Following general procedure 3 in Example E gave S2c; 1H NMR (400 MHz, CDCl$_3$) δ 7.55 (d, J=8.2 Hz, 2H), 7.41 (d, J=8.1 Hz, 2H), 7.29 (s, 1H), 7.26-7.24 (m, 1H), 6.68-6.62 (m, 2H), 6.24 (dd, J=16.0, 5.8 Hz, 1H), 4.62 (s, 2H), 4.32 (m, 1H), 4.27 (q, J=7.1 Hz, 2H), 3.13 (dd, J=13.7, 3.9 Hz, 1H), 2.92 (dd, J=13.7, 8.5 Hz, 1H), 2.75 (brs, 1H), 2.26 (s, 3H), 1.30 (t, J=7.1 Hz, 3H); MS (ES) m/z: 463 (M+Na+).

Following general procedure 2 in Example A gave S2d Compound 41 (91%); 1H NMR (300 MHz, CDCl$_3$) δ 7.54 (d, J=8.2 Hz, 2H), 7.40 (d, J=8.2 Hz, 2H), 7.28-7.25 (m, 2H), 6.68-6.63 (m, 2H), 6.24 (dd, J=16.0, 5.7 Hz, 1H), 4.67 (s, 2H), 4.34 (m, 1H), 3.14 (m, 1H), 2.99-2.95 (m, 1H), 2.24 (s, 3H); MS (ES) m/z: 411 (M−H+).

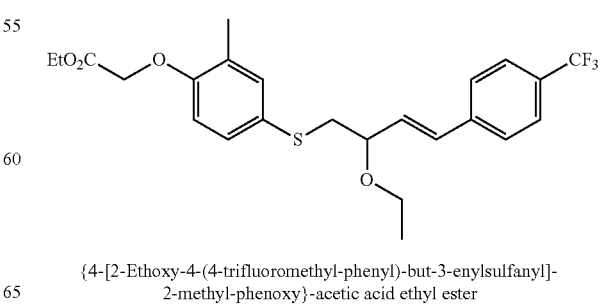

S3

{4-[2-Ethoxy-4-(4-trifluoromethyl-phenyl)-but-3-enylsulfanyl]-2-methyl-phenoxy}-acetic acid ethyl ester Following general procedure 4 in Example L gave S3 (35%); 1H NMR (300 MHz, CDCl$_3$) δ 7.56 (d, J=8.2 Hz, 2H), 7.42 (d, J=8.2 Hz, 2H), 7.23 (s, 1H), 7.19 (dd, J=8.4, 2.1 Hz, 1H), 6.61 (s, 1H), 6.57 (d, J=8.9 Hz, 1H), 6.17 (dd, J=16.0, 7.3 Hz, 1H), 4.60 (s, 2H), 4.26 (q, J=7.1 Hz, 2H), 3.99 (q, J=6.7 Hz, 1H), 3.60-3.52 (m, 1H), 3.48-3.38 (m, 1H), 3.16 (dd, J=13.3, 6.3 Hz, 1H), 2.99 (dd, J=13.3, 6.5 Hz, 1H), 2.23 (s, 3H), 1.30 (t, J=7.1 Hz, 3H), 1.21 (t, J=7.0 Hz, 3H); MS (ES) m/z: 491 (M+Na+).

Compound 42

{4-[2-Ethoxy-4-(4-trifluoromethyl-phenyl)-but-3-enylsulfanyl]-2-methyl-phenoxy}-acetic acid Following general procedure 2 in Example A gave Compound 42 (93%); 1H NMR (300 MHz, CDCl$_3$) δ 7.56 (d, J=8.1 Hz, 2H), 7.42 (d, J=8.1 Hz, 2H), 7.24 (s, 1H), 7.21 (d, J=8.5 Hz, 1H), 6.64-6.56 (m, 2H), 6.21-6.09 (dd, J=16.0, 7.3 Hz, 1H), 4.65 (s, 2H), 4.00 (q, J=6.6 Hz, 1H), 3.61-3.53 (m, 1H), 3.49-3.39 (m, 1H), 3.16-2.97 (m, 2H), 2.22 (s, 3H), 1.21 (t, J=7.0 Hz, 3H); MS (ES) m/z: 463 (M+Na+).

Example T

Scheme T

Compound 43

Following general procedure 2 in Example A and using M2 gave Compound 43 (90%); [α]$_D$ +54.5° (c 1.0, MeOH); $^1$H NMR (300 MHz, CD$_3$OD) δ 7.54 (d, J=8.6 Hz, 2H), 7.23 (m, 2H), 6.99 (d, J=8.6 Hz, 2H), 6.69 (d, J=8.2 Hz, 1H), 4.62 (s, 2H), 3.96-4.12 (m, 3H), 3.13 (dd, J=6.5, 13.8 Hz, 1H), 3.02 (dd, J=5.8, 13.8 Hz, 1H), 2.18 (s, 3H); MS (ES) m/z: 439 (M+Na$^+$). Anal. Calcd for C$_{19}$H$_{19}$F$_3$O$_5$S: C, 54.80; H, 4.60. Found: C, 54.94; H, 4.51.

Example U

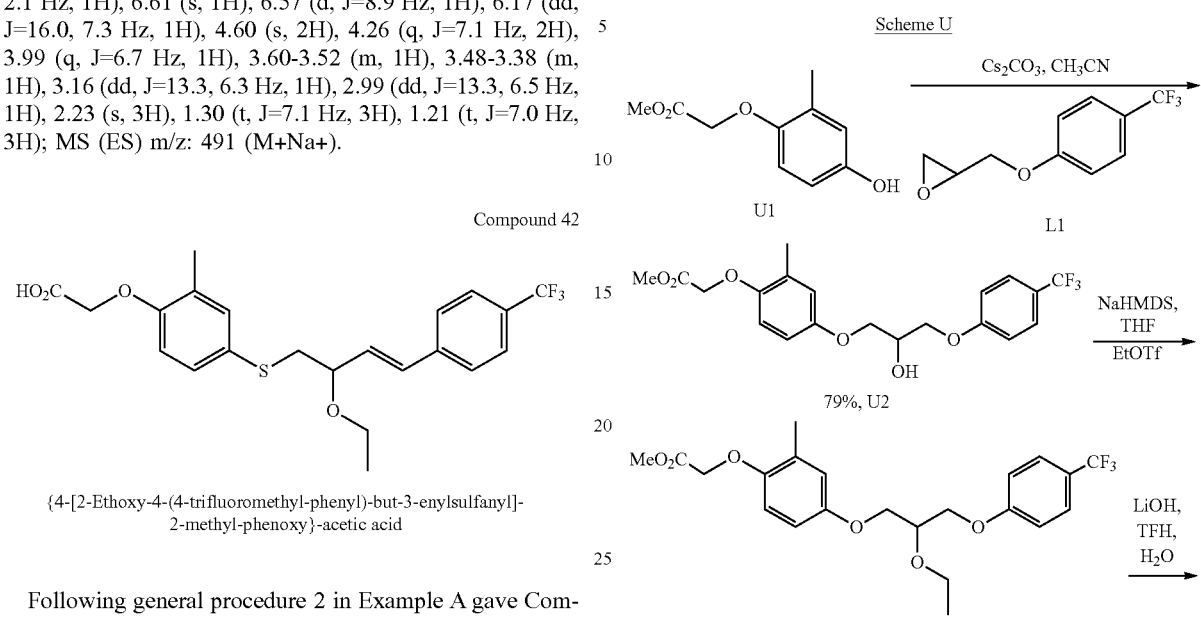

A mixture of (4-hydroxy-2-methyl-phenoxy)-acetic acid methyl ester U1 (196.2 mg, 1.0 mmol), which can be readily made according to, for example, Sznaidman et al., Bioorganic & Medicinal Chemistry Letters 13 (2003) 1517-1521, L1 (327.3 mg, 1.5 mmol), and Cs$_2$CO$_3$ (488.8 mg, 1.5 mmol) in actonitrile (4 mL) was refluxed for 4 h. Water and ether were added, the organic layer was separated, and the aqueous layer was extracted with ether. The combined organic extracts were combined, dried, concentrated, and column chromatographed (EtOAc/hexane: ½) to give 327.4 mg (79%) of U2; $^1$H NMR (300 MHz, CDCl$_3$) δ 7.55 (d, J=8.8 Hz, 2H), 6.99 (d, J=8.8 Hz, 2H), 6.77 (s, 1H), 6.67 (m, 2H), 4.60 (s, 2H), 4.37 (m, 1H), 4.18 (m, 2H), 4.10 (m, 2H), 3.79 (s, 3H), 2.56 (br. s, 1H), 2.27 (s, 3H); MS (ES) m/z: 437 (M+Na$^+$).

U3

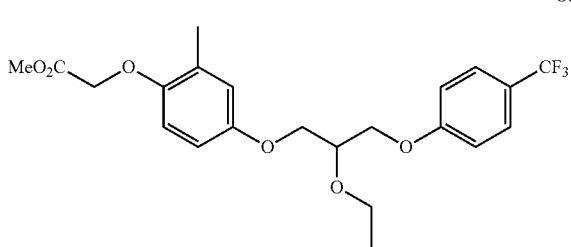

Replacing O1 with U2 and following the procedure for preparation of O2 in Example O gave U3 (51%); $^1$H NMR (300 MHz, CDCl$_3$) δ 7.54 (d, J=8.7 Hz, 2H), 6.99 (d, J=8.7 Hz, 2H), 6.76 (s, 1H), 6.66 (m, 2H), 4.59 (s, 2H), 4.23 (m, 1H), 4.15 (m, 1H), 4.09 (m, 2H), 4.01 (m, 1H), 3.79 (s, 3H), 3.75 (q, J=6.9 Hz, 2H), 2.26 (s, 3H), 1.25 (t, J=7.0 Hz, 3H); MS (ES) m/z: 465 (M+Na$^+$).

Compound 44

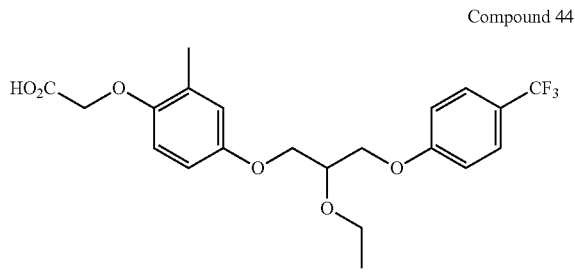 [SMILES: CCOC(COc1ccc(C(F)(F)F)cc1)COc1ccc(OCC(=O)O)c(C)c1]

Following the general procedure 2 in Example A gave Compound 44 (92%); $^1$H NMR (300 MHz, CDCl$_3$) δ 7.54 (d, J=8.7 Hz, 2H), 6.98 (d, J=8.7 Hz, 2H), 6.77 (s, 1H), 6.68 (m, 2H), 4.61 (s, 2H), 4.23 (m, 1H), 4.17 (m, 1H), 4.09 (m, 2H), 4.01 (m, 1H), 3.79 (s, 3H), 3.76 (q, J=7.0 Hz, 2H), 2.26 (s, 3H), 1.25 (t, J=7.0 Hz, 3H); MS (ES) m/z: 427 (M−H$^+$).

Compound 45

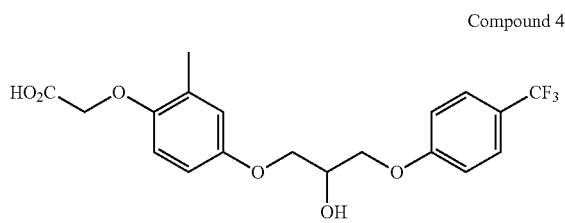

Following the general procedure 2 in Example A, hydrolysis of U2 gave Compound 45 (93%); $^1$H NMR (300 MHz, CD$_3$OD) δ 7.57 (d, J=8.7 Hz, 2H), 7.10 (d, J=8.6 Hz, 2H), 6.79 (s, 1H), 6.72 (m, 2H), 4.59 (s, 2H), 4.26 (m, 1H), 4.11-4.21 (m, 2H), 4.06 (m, 2H), 2.22 (s, 3H); MS (ES) m/z: 423 (M+Na$^+$).

D. FORMULATION AND ADMINISTRATION

The present compounds are PPAR delta agonists and are therefore useful in treating or inhibiting the progression of PPAR delta mediated conditions, such as diabetes, cardiovascular diseases, Metabolic X Syndrome, hypercholesterolemia, hypo-HDL-cholesterolemia, hyper-LDL-cholesterolemia, dyslipidemia, atherosclerosis, obesity, and complications thereof. For instance, complications of diabetes include such conditions as neuropathy, nephropathy, and retinopathy.

The invention features a method for treating a subject with a PPAR delta mediated disease, said method comprising administering to the subject a therapeutically effective amount of a pharmaceutical composition comprising a compound of the invention. The invention also provides a method for treating or inhibiting the progression of diabetes or impaired glucose tolerance in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the PPAR delta could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg or 750 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of Formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the use of the disclosed compounds and compositions.

E. USE

The compounds of the present invention are pharmaceutically active, for example, as PPAR delta agonists. According to one aspect of the invention, the compounds are preferably selective PPAR delta agonists, having an activity index (e.g., PPAR delta potency over PPAR alpha/gamma potency) of 10 or more, and preferably 15, 25, 30, 50 or 100 or more.

According to the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypertension, CAD (coronary artery disease), coronary heart disease, and hypertriglyceridemia. Preferred compounds of the invention are useful in lowering serum levels of low-density lipoproteins (LDL), intermediate density lipoprotein (IDL), and/or small-density LDL and other atherogenic molecules, or molecules that cause atherosclerotic complications, thereby reducing cardiovascular complications. Preferred compounds also are useful in elevating serum levels of high-density lipoproteins (HDL), in lowering serum levels of triglycerides, LDL, and/or free fatty acids. It is also desirable to lower fasting plasma glucose (FPG)/HbA1c.

The invention also features pharmaceutical compositions which include, without limitation, one or more of the disclosed compounds, and pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Combination Therapy

The compounds of the present invention may be used in combination with other pharmaceutically active agents. These agents include lipid lowering agents, and blood pressure lowering agents such as statin drugs and the fibrates.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term ""jointly effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

Anti-diabetic agents include thiazolidinedione and non-thiazolidinedione insulin sensitizers, which decrease peripheral insulin resistance by enhancing the effects of insulin at target organs and tissues.

Some of the following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+ −)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI 991, CS 045, GR 92132, GR 92132X);
(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2, 4-thiazolidinedione or 5-(6-(2-fluorobenzyloxy) naphthalen-2-ylmethyl)thiazolidine-2,4-dione, also known as MCC-555 or neoglitazone); and
(5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4)methyl-);
(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and
(3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl)ethyl)-L-tyrosine, or GW2570 or GI-262570).

Other agents have also been shown to have PPAR modulator activity such as PPAR gamma, SPPAR gamma, and/or PPAR delta/gamma agonist activity. Examples are listed below:

(1) AD 5075;
(2) R 119702 ((+ −)-5-(4-(5-Methoxy-1H-benzimidazol-2-ylmethoxy)benzyl)thiazolin-2, 4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris (4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);

(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzenepropanoic acid or 3-(4-(2-(N-(2-benzoxazolyl)-N-methylamino)ethoxy)phenyl)-2(S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

(B) Other insulin sensitizing agents include, but are not limited to:
(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl)ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis (1,4-phenylene)bismethylenebis(thiazolidine-2,4-dione);
(12) TS 971;
(13) T 174 ((+ −)-5-(2,4-dioxothiazolidin-5-ylmethyl)-2-(2-naphthylmethyl)benzoxazole);
(14) SDZ PGU 693 ((+)-trans-2(S-((4-chlorophenoxy) methyl)-7alpha-(3,4-dichlorophenyl)tetrahydropyrrolo (2,1-b)oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl) methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2(S)-(propylamino)propionic acid);
(33) DRF 2189 (5-((4-(2-(1-Indolyl)ethoxy)phenyl) methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

(C) Biguanides, which decrease liver glucose production and increases the uptake of glucose. Examples include metformin such as:
(1) 1,1-dimethylbiguanide (e.g., Metformin-DepoMed, Metformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

(D) Alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples include, but are not limited to:

(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);

(2) Miglitol (3,4,5-piperidinetriol, 1-(2-hydroxyethyl)-2-(hydroxymethyl)-, (2R(2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);

(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);

(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);

(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and (6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

(E) Insulins include regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:

(1) Biota;
(2) LP 100;
(3) (SP-5-21)-oxobis (1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

(F) Insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
    (4a) DPP-728 or LAF 237 (2-pyrrolidinecarbonitrile, 1-(((2-((5-cyano-2-pyridinyl)amino)ethyl)amino) acetyl), known as NVP-DPP-728, DPP-728A, LAF-237);
    (4b) P 3298 or P32/98 (di-(3N-((2S,3S)-2-amino-3-methyl-pentanoyl)-1,3-thiazolidine)fumarate);
    (4c) TSL 225 (tryptophyl-1,2,3,4-tetrahydroisoquinoline-3-carboxylic acid);
    (4d) Valine pyrrolidide (valpyr);
    (4e) 1-aminoalkylisoquinolinone-4-carboxylates and analogues thereof;
    (4f) SDZ 272-070 (1-(L-Valyl)pyrrolidine);
    (4g) TMC-2A, TMC-2B, or TMC-2C;
    (4h) Dipeptide nitriles (2-cyanopyrrolodides);
    (4i) CD26 inhibitors; and
    (4j) SDZ 274-444;
(5) glucagon antagonists such as AY-279955; and
(6) amylin agonists which include, but are not limited to, pramlintide (AC-137, Symlin, tripro-amylin or pramlintide acetate).

The present compounds may also increase insulin sensitivity with little or no increase in body weight than that found with the use of existing PPAR gamma agonists. Oral anti-diabetic agents may include insulin, sulfonylureas, biguanides, meglitinides, AGI's, PPAR alpha agonists, and PPAR gamma agonists, and dual PPAR alpha/gamma agonists.

The present compounds also may increase fat and/or lipid metabolism, providing a method for losing weight, losing fat weight, lowering body mass index, lowering lipids (such as lowering triglycerides), or treating obesity or the condition of being overweight. Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include anti-hypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F. BIOLOGICAL EXAMPLES

Transfection Assay Method for PPAR Receptors

HEK293 cells were grown in DMEM/F-12 Media supplemented with 10% FBS and glutamine (GIBCOBRL). The cells were co-transfected with DNA for PPAR-Gal4 (PPARα, γ or δ) receptor and Gal4-Luciferase Reporter using the DMRIE-C Reagent. On the following day, the medium was replaced with 5% Charcoal treated FBS growth medium. After six hours, cells were trypsinized and seeded at a density of 50,000 cell/well into 96 well plates and incubated overnight at 37° C. in a 5% $CO_2$ incubator. Cells were then treated with test compounds or vehicle and incubated for 24 hours at 37° C. in a 5% $CO_2$ incubator. Luciferase activity was assayed using the Steady-Glo Luciferase Assay Kit from Promega. DMRIE-C Reagent was purchased from GIBCO Cat. No. 10459-014. OPTI-MEM I Reduced Serum Medium was purchased from GIBCO Cat. No. 31985. Steady-Glo Luciferase Assay Kit was purchased from Promega Part# E254B.

A variety of example compounds have been made and tested, with a range of in vitro results. Below are representative compounds and data; in some cases, where multiple $EC_{50}$'s are shown, multiple measurements were taken. Naturally, different compounds in Formula (I) may have not have activities identical to any one compound below.

TABLE 2

| In Vitro Data | |
|---|---|
| Compound Number | $EC_{50}$ (PPAR delta) nM |
| 1 | 9.2, 5.6 |
| 2 | 0.02, 0.33, 0.03, 0.47, 1.5 |
| 3 | 0.08, 0.04 |
| 4 | 29.6 |
| 5 | 0.02, 0.08, 0.04 0.01, 0.36, 0.36 |
| 6 | 3.3, 3.7, 3.3 |
| 7 | 211 |
| 8 | 215 |
| 9 | 16.6, 18.5 |
| 10 | 29, 56 |
| 11 | 5.7 |
| 12 | 19.9 |
| 13 | 79 |
| 14 | 16.2, 21.5 |
| 15 | 0.76, 0.56, 0.88, 3.4, 5.0, 1.1 |
| 16 | 22.4, 27.5 |
| 17 | 4.2, 3.2, 1.5, 4.5, 0.69, 2.7 |
| 18 | 4.3, 4.3 |
| 19 | 7.5, 6.5 |
| 20 | 3.4, 14.6, 1.4 |
| 21 | 3.7, 4.2 |
| 22 | 1.3, 2.6, 1.4, 2.1, 4.2, 2.3 |
| 23 | 70 |
| 24 | 6.3, 6.6, 5.1, 6.6, 6.4, 3.7 |
| 25 | 25.2, 8.9, 8.8 |
| 26 | 126 |
| 27 | 11.9, 18.5 |
| 28 | 57.3, 67.8 |
| 29 | 62.1 |
| 30 | 23.9 |
| 31 | >1000 |
| 32 | 11.2, 11.2 |
| 33 | 4.7, 4.6 |
| 34 | 16.3, 17.7 |
| 35 | 2.3, 4.1 |
| 36 | 52.9 |
| 37 | 1.9, 2.9 |
| 38 | 6.9, 7.7, 19.7, 6.5, 4.6 |
| 39 | 12.5, 17.9 |
| 40 | 39.3, 43.7 |
| 41 | 144 |
| 42 | 8.0, 7.9 |
| 43 | 43.2 |
| 44 | 24.3 |
| 45 | 618.3 |

The compounds in Table 3 are also of interest, which have been made and tested likewise:

TABLE 3

Compounds of Interest

| Structure | Physical Data | $EC_{50}$ (PPAR delta) nM |
|---|---|---|
| 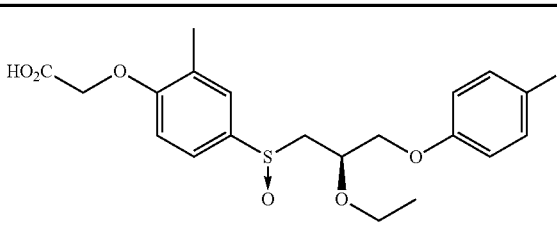 | $^1$H NMR (400 MHz, $CD_3OD$) δ 7.50-7.58 (m, 8 H), 6.98-7.08 (m, 6 H), 4.74 (s, 2 H), 4.73 (s, 2 H), 4.06-4.22 (m, 4 H), 3.84 (m, 2 H), 3.73 (m, 1 H), 3.58 (m, 1 H), 3.46 (m, 1 H), 3.23-3.36 (m, 3 H), 3.13 (m, 2 H), 2.33 (s, 3 H), 2.31 (s, 3H), 1.24 (t, J = 7.0 Hz, 3 H), 1.12 (t, J = 7.0 Hz, 3H); MS (ES) m/z: 459 (M − H$^+$). | >3000 |

TABLE 3-continued

Compounds of Interest

| Structure | Physical Data | EC$_{50}$ (PPAR delta) nM |
|---|---|---|
| HO$_2$C–O–(aryl)–S–(CH$_2$)$_3$–O–(aryl)–CF$_3$ (2-methyl) | $^1$H NMR (300 MHz, CDCl$_3$) δ 7.51 (d, J = 8.7 Hz, 2 H), 7.19 (m, 2 H), 6.91 (d, J = 8.5 Hz, 2 H), 6.62 (d, J = 8.4 Hz, 1H), 4.56 (s, 2 H), 4.07 (t, J = 5.3 Hz, 2 H), 3.01 ( t, J = 7.0 Hz, 2 H), 2.21 (s, 3 H), 2.06 (m, 2 H); MS (ES) m/z: 423 (M + Na$^+$). | 17.6 |

G. OTHER EMBODIMENTS

The features and principles of the invention are illustrated in the discussion, examples, and claims herein. Various adaptations and modifications of the invention will be apparent to a person of ordinary skill in the art and such other embodiments are also within the scope of the invention. Publications cited herein are incorporated in their entirety by reference.

The invention claimed is:

1. A method for treating or inhibiting the progression of a PPAR-delta mediated condition, said method comprising administering to a patient in need of treatment a pharmaceutically effective amount of Formula (II):

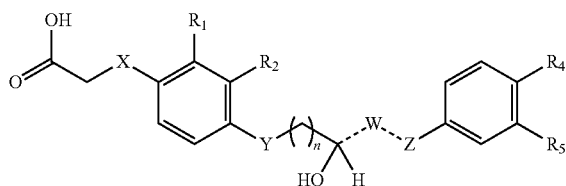

wherein
X is selected from a covalent bond, S or O;
Y is S or O;
- - - - - W - - - - - represents a group selected from —CH═, —CH$_2$—, —CH$_2$—CH$_2$—, —CH$_2$—CH═, and —CH═CH—;
Z is selected from O, CH, and CH$_2$, provided when Y is O, Z is O;

R$_1$ and R$_2$ are independently selected from H, C$_{1-3}$ alkyl, C$_{1-3}$ alkoxy, halo, and NR$_a$R$_b$ wherein R$_a$ and R$_b$ are independently H or C$_{1-3}$ alkyl;

R$_3$ and R$_4$ are independently selected from H, halo, cyano, hydroxy, acetyl, C$_{1-5}$ alkyl, C$_{1-4}$ alkoxy, and NR$_c$R$_d$ wherein R$_c$ and R$_d$ are independently H or C$_{1-3}$ alkyl, provided that R$_3$ and R$_4$ are not both H;

n is 1 or 2;

or a pharmaceutically acceptable salt thereof.

2. The method of claim 1 wherein the compound is selected from the group consisting of
acetic acid, {4-[(2R)-2-hydroxy-3-(4-trifluoromethyl-phenoxy)-propylsulfanyl]-2-methyl-phenoxy}-; and
acetic acid, {4-[(2S)-2-hydroxy-3-(4-trifluoromethyl-phenoxy)-propylsulfanyl]-2-methyl-phenoxy}.

3. The method of claim 1, wherein the compound is acetic acid, {4-[(2R)-2-hydroxy-3-(4-trifluoromethyl-phenoxy)-propylsulfanyl]-2-methyl-phenoxy}-.

4. The method of claim 1, wherein the compound is acetic acid, {4-[(2S)-2-hydroxy-3-(4-trifluoromethyl-phenoxy)-propylsulfanyl]-2-methyl-phenoxy}-.

5. The method of claim 1, wherein the PPAR-delta mediated condition is selected from the group consisting of diabetes, cardiovascular diseases, Metabolic X Syndrome, hypercholesterolemia, hypo-HDL-cholesterolemia, hyper-LDL-cholesterolemia, dyslipidemia, artherosclerosis, and obesity.

6. The method of claim 5, wherein the compound is selected from the group consisting of acetic acid, {4-[(2R)-2-hydroxy-3-(4-trifluoromethyl-phenoxy)-propylsulfanyl]-2-methyl-phenoxy}-; and
acetic acid, {4-[(2S)-2-hydroxy-3-(4-trifluoromethyl-phenoxy)-propylsulfanyl]-2-methyl-phenoxy}.

* * * * *